United States Patent
Sielecki-Dzurdz

(10) Patent No.: US 7,291,647 B2
(45) Date of Patent: Nov. 6, 2007

(54) GUANYLHYDRAZONE COMPOUNDS, COMPOSITIONS, METHODS OF MAKING AND USING

(75) Inventor: Thais Sielecki-Dzurdz, Kennett Square, PA (US)

(73) Assignee: Cytokine Pharmasciences, Inc., King of Prussia, PA (US)

( * ) Notice: Subject to any disclaimer, the term of this patent is extended or adjusted under 35 U.S.C. 154(b) by 0 days.

(21) Appl. No.: 11/205,187

(22) Filed: Aug. 17, 2005

(65) Prior Publication Data
US 2006/0041002 A1     Feb. 23, 2006

Related U.S. Application Data

(60) Provisional application No. 60/601,992, filed on Aug. 17, 2004.

(51) Int. Cl.
*A61K 31/155* (2006.01)
*C07C 281/18* (2006.01)

(52) U.S. Cl. ............... 514/632; 514/378; 514/403; 514/448; 548/247; 548/374.1; 549/72; 564/227

(58) Field of Classification Search ............ 564/227; 514/378, 403, 448, 632; 548/247, 374.1; 549/72
See application file for complete search history.

(56) References Cited

U.S. PATENT DOCUMENTS

| | | | |
|---|---|---|---|
| 5,599,984 A * | 2/1997 | Bianchi et al. ............ 564/157 |
| 5,750,573 A | 5/1998 | Bianchi et al. |
| 5,753,684 A | 5/1998 | Bianchi et al. |
| 5,849,794 A | 12/1998 | Bianchi et al. |
| 5,854,289 A | 12/1998 | Bianchi et al. |
| 5,859,062 A | 1/1999 | Bianchi et al. |
| 6,008,255 A | 12/1999 | Bianchi et al. |
| 6,022,900 A | 2/2000 | Bianchi et al. |
| 6,180,676 B1 | 1/2001 | Bianchi et al. |
| 6,248,787 B1 | 6/2001 | Bianchi et al. |
| 6,319,894 B1 | 11/2001 | Tracey et al. |
| 6,673,777 B1 | 1/2004 | Tracey et al. |
| 2002/0028851 A1 | 3/2002 | Bianchi et al. |
| 2003/0134904 A1 | 7/2003 | Giordano et al. |
| 2003/0203969 A1 | 10/2003 | Bevec et al. |
| 2004/0043079 A1 | 3/2004 | D'Souza |
| 2006/0014833 A1 * | 1/2006 | Sielecki-Dzurdz .......... 514/554 |

FOREIGN PATENT DOCUMENTS

| EP | 1 389 480 A1 | 2/2004 |
|---|---|---|
| WO | 03/072135 A2 | 9/2003 |

OTHER PUBLICATIONS

Kerwin, James F., Jr., et al., "Nitric Oxide: A New Paradigm for Second Messengers," Journal of Medicinal Chemistry, 38(22):4343-4362 (1995).

* cited by examiner

*Primary Examiner*—Rebecca Anderson
*Assistant Examiner*—Joseph R. Kosack
(74) *Attorney, Agent, or Firm*—Law Office of John K Pinke PLLC

(57) ABSTRACT

The present invention relates to compounds having the formula:

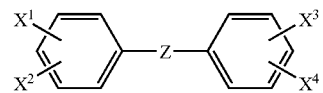

salts thereof; compositions comprising one or more of the compounds and/or salts thereof; methods of using; and methods of making.

20 Claims, 12 Drawing Sheets

Figure 1

| Drug | IC$_{50}$ (μg/mL) |
|---|---|
| Analog 5 | 27.71 |
| Analog 6 | 99.64 |
| Analog 7 | 75.79 |
| Analog 9 | 78.08 |
| Analog 10 | 8.75 |
| Analog 11 | 47.55 |
| Analog 12 | 26.71 |
| Analog 13 | >100 |
| CNI-1493 | 7.71 |
| CNI-1493 | 8.67 |

Figure 2

| Drug | IC$_{50}$ (μg/mL) |
|---|---|
| Analog 5 | 0.11 |
| Analog 6 | 1.57 |
| Analog 7 | 0.63 |
| Analog 7 | 0.58 |
| Analog 9 | 6.52 |
| Analog 9 | 9.93 |
| Analog 10 | 5.79 |
| Analog 10 | 6.67 |
| Analog 11 | 27.94 |
| Analog 12 | 0.36 |
| Analog 13 | 50.14 |
| CNI-1493 | 5.86 |
| CNI-1493 | 5.36 |

Figure 3

| Drug | IC$_{50}$ (µg/mL) TNFα | IC$_{50}$ (µg/mL) Nitric Oxide |
|---|---|---|
| Analog 5 | 27.71 | 0.11 |
| Analog 6 | 99.64 | 1.57 |
| Analog 7 | 75.79 | 0.63 |
| Analog 9 | 78.08 | 6.52 |
| Analog 10 | 8.75 | 5.79 |
| Analog 11 | 47.55 | 27.94 |
| Analog 12 | 26.71 | 0.36 |
| Analog 13 | >100 | 50.14 |
| CNI-1493 | 7.71 | 5.86 |
| CNI-1493 | 8.67 | 5.36 |

| Cpd ID | Structure | MF | MW | TNF µg/ml (µmol) | NO µg/ml (µmol) |
|---|---|---|---|---|---|
| Analog 3 | 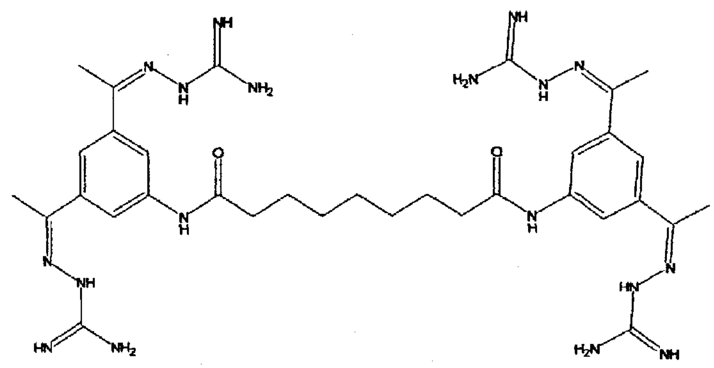 | C33H50N18O2 | 730.9 | 44.54 (60.9)* | 0.69 (0.94)* |

Figure 5 B

| Analog | | | | |
|---|---|---|---|---|
| Analog 4 | (structure) | C30H36N2O6 | 520.6 | >100 (>192) | 75.41 (145) |
| Analog 5 | (structure) | C31H41ClN6O5 | 613.2 | 27.71 (45) | 0.11 (0.179) |

| Analog | | | | | |
|---|---|---|---|---|---|
| 6 | | C32H46Cl2N10O4 | 705.2 | 99.64 (141) | 1.57 (2.23) |
| 1 | | C34H44N18O2* 4HCl | 882.7 | | |

Figure 5 D

| Analog | | | | |
|---|---|---|---|---|
| Analog 2 | (structure) | C36H48N18O2*<br>4HCl | 765 | 75.79 (91) | 0.63 (.757) |
| Analog 7 | (structure) | C30H49Cl4N18O2 | 832.3 | | |

Figure 5 E

| Analog | Structure | Formula | MW | | |
|---|---|---|---|---|---|
| Analog 8 | 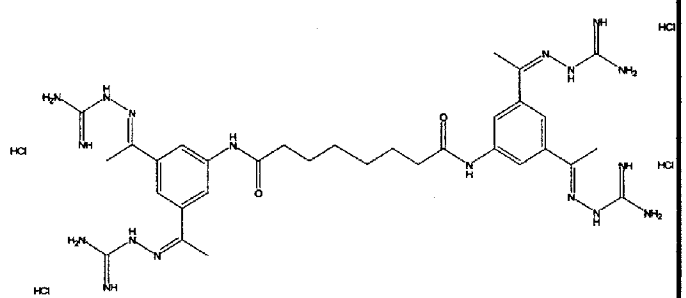 | C32H52Cl4N18O2 | 860.3 | | 6.52 (7.57) |
| Analog 9 | 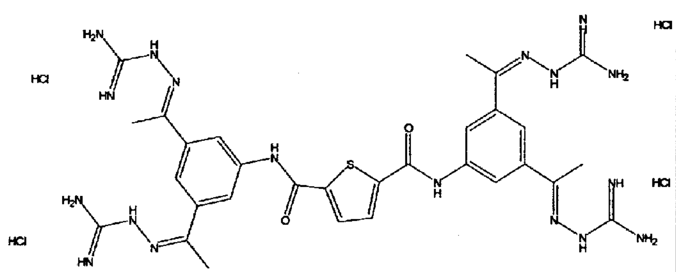 | C30H42Cl4N18O2 S | 860.7 | 78.08 (90.7) | |

Figure 5 F

| Analog | | | | | |
|---|---|---|---|---|---|
| 10 | [structure] | C29H42Cl2N10O2 | 621.6 | 8.75 (14.08) | 5.79 (9.3) |
| 11 | [structure] | C29H42Cl2N10O2 | 621.6 | 47.55 (76.5) | 27.94 (44.9) |

| Analog | | | | | |
|---|---|---|---|---|---|
| 12 |  | C33H49Cl4N19O3 | 901.7 | 26.71 (29.6) | 0.36 (.399) |
| 13 |  | C33H48N14O3 | 688.8 | >100 (>145) | 50.14 (72.8) |

Figure 5 H

| | | |
|---|---|---|
| Analog 14 | | C33H54Cl4N19O2 | 876.7 |
| Analog 15 | | C30H44N18O2(4H Cl) | 832.3 |

Figure 5 I

| Analog | | | |
|---|---|---|---|
| Analog 16 | (structure) | C32H44Cl4N18O2 | 852.3 |
| Analog 17 | (structure) | C28H44Cl4N18O3 | 820.3 |

GUANYLHYDRAZONE COMPOUNDS, COMPOSITIONS, METHODS OF MAKING AND USING

CROSS-REFERENCE TO RELATED APPLICATIONS

This application claims priority to U.S. Provisional Application Ser. No. 60/601,992, filed Aug. 17, 2004, the entire contents of which are hereby incorporated by reference.

BACKGROUND OF THE INVENTION

1. Field of the Invention

The present invention is directed to the field of pharmacology. In one aspect, the invention is directed to guanylhydrazone compounds. The guanylhydrazone compounds or salts thereof may be used for therapeutic regimens or for the identification of candidate compounds for producing effective drugs having increased efficacy or bioavailability.

2. Related Art

United States Patent Application Publication No. 2004/0043079 to D'Souza relates to microencapsulation as a delivery vehicle for a drug. The guanylhydrazone compound CNI-1493 is disclosed in one embodiment.

United States Patent Application Publication No. 2003/0134904 to Giordano et al. relates to guanylhydrazone compounds for inhibiting RNase P activity.

United States Patent Application Publication No. 2003/0203969 to Bevec et al. relates to pharmaceutically active aromatic guanylhydrazone compounds.

United States Patent Application Publication No. 2002/0028851 to Bianchi et al. relates to guanylhydrazone compounds and their uses to treat inflammatory conditions.

U.S. Pat. Nos. 6,673,777 and 6,143,728 to Tracey et al. relate to guanylhydrazone compounds and their uses for treating diseases associated with T cell activation.

U.S. Pat. No. 6,319,894 to Tracey et al. relates to complexes and combinations of fetuin with therapeutic agents to enhance the activity of the therapeutic agents. Guanylhydrazone compounds are disclosed.

U.S. Pat. Nos. 6,248,787; 6,180,676; 6,022,900; 6,008,255; 5,859,062; 5,854,289; 5,849,794; 5,753,684; 5,750,573; and 5,599,984 all to Bianchi et al. relate to guanylhydrazone compounds and their uses to treat inflammatory conditions.

The article, "Nitric Oxide: A New Paradigm for Second Messengers" in *Journal of Medicinal Chemistry*, 1995, Vol. 38, No. 22, pp 4343-4362 relates to nitric oxide and its importance as a second messenger in biological environments.

The entire contents of every reference cited herein is independently incorporated by reference for all purposes.

SUMMARY OF THE INVENTION

One embodiment provides a compound, having the formula:

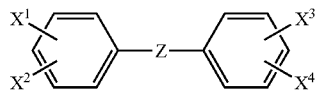

or a salt thereof;
wherein $X^1$, $X^2$, $X^3$, and $X^4$ each independently represent H, GhyCH—, GhyCCH$_3$—, or CH$_3$CO—, with the provisos that $X^1$, $X^2$, $X^3$ and $X^4$ are not simultaneously H;

wherein Z is one or more selected from the group consisting of:

; and

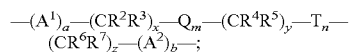

and combinations thereof;
wherein a is selected from the group consisting of 0, 1, 2, 3, 4, 5, 6, 7, 8, and 9;
wherein b is selected from the group consisting of 0, 1, 2, 3, 4, 5, 6, 7, 8, and 9;
wherein x is selected from the group consisting of 0, 1, 2, 3, 4, 5, 6, 7, 8, and 9;
wherein y is selected from the group consisting of 0, 1, 2, 3, 4, 5, 6, 7, 8, and 9;
wherein z is selected from the group consisting of 0, 1, 2, 3, 4, 5, 6, 7, 8, and 9;
wherein m is selected from the group consisting of 0, 1, 2, 3, 4, 5, 6, 7, 8, and 9;
wherein n is selected from the group consisting of 0, 1, 2, 3, 4, 5, 6, 7, 8, and 9;
wherein $A^1$ and $A^2$ are each independently selected from the group consisting of —NR$^8$(CO)NR$^9$—, —(CO)NR$^8$—, NR$^8$(CO)—, NR$^8$—, —O—, —S—, —S(=O)—, —SO$_2$—, —SO$_2$NR$^8$—, —NR$^8$SO$_2$—, and salts thereof;
wherein Q and T are each independently selected from the group consisting of —NR$^{10}$(CO)NR$^{11}$—, —(CO)NR$^{10}$—, —NR$^{10}$(CO)—, —NR$^{10}$—, —O—, —S—, —S(=O)—, —SO$_2$—, —SO$_2$NR$^{10}$—, —NR$^{10}$SO$_2$—, salts thereof, branched or unbranched, saturated or unsaturated, substituted or unsubstituted C$_1$-C$_{20}$ alkylene, saturated or unsaturated, substituted or unsubstituted C$_3$-C$_{20}$ cycloalkylene, substituted or unsubstituted C$_5$-C$_{25}$ arylene, and combinations thereof;
wherein one or more carbon atoms in any of said alkylene, cycloalkylene or arylene in said Q and/or T may each be independently replaced with one or more heteroatoms selected from the group consisting of nitrogen, oxygen, sulfur, and a combination thereof;
and wherein when substituted, said alkylene, cycloalkylene or arylene in said Q and/or T are each independently substituted with one or more substituent groups selected from the group consisting of hydroxy, halo, bromo, chloro, iodo, fluoro, —N$_3$, —CN, —NC, —SH, —NO$_2$, —NH$_2$, (C$_1$-C$_{20}$)alkyl, phenyl, (C$_3$-C$_{20}$)cycloalkyl, (C$_1$-C$_{20}$)alkoxy, (C$_3$-C$_{25}$)heteroaryl, (C$_3$-C$_{25}$)heterocyclic, (C$_2$-C$_{20}$)alkenyl, (C$_3$-C$_{20}$)cycloalkenyl, (C$_2$-C$_{20}$)alkynyl, (C$_5$-C$_{20}$)cycloalkynyl, (C$_5$-C$_{25}$)aryl, perhalo(C$_1$-C$_{20}$)alkyl, (C$_1$-C$_{20}$)alkyl-O—, phenyl-O—, (C$_3$-C$_{20}$)cycloalkyl-O—, (C$_3$-C$_{25}$)heteroaryl-O—, (C$_3$-C$_{25}$)heterocyclic-O—, (C$_2$-C$_{20}$)alkenyl-O—, (C$_3$-C$_{20}$)cycloalkenyl-O—, (C$_2$-C$_{20}$)alkynyl-O—, (C$_5$-C$_{20}$)cycloalkynyl-O—, (C$_5$-C$_{25}$)aryl-O—, perhalo(C$_1$-C$_{20}$)alkyl-O—, (C$_1$-C$_{20}$)alkyl-S—, phenyl-S—, (C$_3$-C$_{20}$)cycloalkyl-S—, (C$_3$-C$_{25}$)heteroaryl-S—, (C$_3$-C$_{25}$)heterocyclic-S—, (C$_2$-C$_{20}$)alkenyl-S—, (C$_3$-C$_{20}$)cycloalkenyl-S—, (C$_2$-C$_{20}$)alkynyl-S—, (C$_5$-C$_{20}$)cycloalkynyl-S—, (C$_5$-C$_{25}$)aryl-S—, perhalo(C$_1$-C$_{20}$)alkyl-S—, (C$_1$-C$_{20}$)alkyl-SO$_2$—, phenyl-SO$_2$—, (C$_3$-C$_{20}$)cycloalkyl-SO$_2$—, (C$_1$-C$_{20}$)alkoxy-SO$_2$—, (C$_3$-C$_{25}$)heteroaryl-SO$_2$—, (C$_3$-C$_{25}$)heterocyclic-SO$_2$—, (C$_2$-C$_{20}$)alkenyl-SO$_2$—, (C$_3$-C$_{20}$)cycloalkenyl-SO$_2$—, (C$_2$-C$_{20}$)alkynyl-SO$_2$—, (C$_5$-C$_{20}$)cycloalkynyl-SO$_2$—, (C$_5$-C$_{25}$)aryl-SO$_2$—, perhalo(C$_1$-C$_{20}$)alkyl-SO$_2$—, H$_2$N—SO$_2$—, (C$_1$-C$_{20}$)alkyl-NH—SO$_2$—, phenyl-NH—SO$_2$—, (C$_3$-C$_{20}$)cycloalkyl-NH—SO$_2$—, (C$_1$-C$_{20}$)alkoxy-NH—SO$_2$—, (C$_3$-

$C_{25}$)heteroaryl-NH—$SO_2$—, ($C_3$-$C_{25}$)heterocyclic-NH—$SO_2$—, ($C_2$-$C_{20}$)alkenyl-NH—$SO_2$—, ($C_3$-$C_{20}$)cycloalkenyl-NH—$SO_2$—, ($C_2$-$C_{20}$)alkynyl-NH—$SO_2$—, ($C_5$-$C_{20}$)cycloalkynyl-NH—$SO_2$—, ($C_5$-$C_{25}$)aryl-NH—$SO_2$—, perhalo($C_1$-$C_{20}$)alkyl-NH—$SO_2$—, {($C_1$-$C_{20}$)alkyl}$_2$N—$SO_2$—, {phenyl}$_2$N—$SO_2$—, {($C_3$-$C_{20}$)cycloalkyl}$_2$N—$SO_2$—, {($C_1$-$C_{20}$)alkoxy}$_2$N—$SO_2$—, {($C_3$-$C_{25}$)heteroaryl}$_2$N—$SO_2$—, {($C_3$-$C_{25}$)heterocyclic}$_2$N—$SO_2$—, {($C_2$-$C_{20}$)alkenyl}$_2$N—$SO_2$—, {($C_2$-$C_{20}$)alkynyl}$_2$N—$SO_2$—, {($C_5$-$C_{20}$)cycloalkynyl}$_2$N—$SO_2$—, {($C_5$-$C_{25}$)aryl}$_2$N—$SO_2$—, {perhalo($C_1$-$C_{20}$)alkyl}$_2$N—$SO_2$—, ($C_1$-$C_{20}$)alkyl-$SO_2$—NH—, phenyl-$SO_2$—NH—, ($C_3$-$C_{20}$)cycloalkyl-$SO_2$—NH—, ($C_1$-$C_{20}$)alkoxy-$SO_2$—NH—, ($C_3$-$C_{25}$)heteroaryl-$SO_2$—NH—, ($C_3$-$C_{25}$)heterocyclic-$SO_2$—NH—, ($C_2$-$C_{20}$)alkenyl-$SO_2$—NH—, ($C_3$-$C_{20}$)cycloalkenyl-$SO_2$—NH—, ($C_2$-$C_{20}$)alkynyl-$SO_2$—NH—, ($C_5$-$C_{20}$)cycloalkynyl-$SO_2$—NH—, ($C_5$-$C_{25}$)aryl-$SO_2$—NH—, perhalo($C_1$-$C_{20}$)alkyl-$SO_2$—NH—, ($C_1$-$C_{20}$)alkyl-NH—, phenyl-NH—, ($C_3$-$C_{20}$)cycloalkyl-NH—, ($C_1$-$C_{20}$)alkoxy-NH—, ($C_3$-$C_{25}$)heteroaryl-NH—, ($C_3$-$C_{25}$)heterocyclic-NH—, ($C_2$-$C_{20}$)alkenyl-NH—, ($C_3$-$C_{20}$)cycloalkenyl-NH—, ($C_2$-$C_{20}$)alkynyl-NH—, ($C_5$-$C_{20}$)cycloalkynyl-NH—, ($C_5$-$C_{25}$)aryl-NH—, perhalo($C_1$-$C_{20}$)alkyl-NH—, {($C_1$-$C_{20}$)alkyl}$_2$N—, {phenyl}$_2$N—, {($C_3$-$C_{20}$)cycloalkyl}$_2$N—, {($C_1$-$C_{20}$)alkoxy}$_2$N—, {($C_3$-$C_{25}$)heteroaryl}$_2$N—, {($C_3$-$C_{25}$)heterocyclic}$_2$N—, {($C_2$-$C_{20}$)alkenyl}$_2$N—, {($C_3$-$C_{20}$)cycloalkenyl}$_2$N—, {($C_2$-$C_{20}$)alkynyl}$_2$N—, {($C_5$-$C_{20}$)cycloalkynyl}$_2$N—, {($C_5$-$C_{25}$)aryl}$_2$N—, {perhalo($C_1$-$C_{20}$)alkyl}$_2$N—, ($C_1$-$C_{20}$)alkyl-(C=O)—NH—, phenyl-(C=O)—NH—, ($C_3$-$C_{20}$)cycloalkyl-(C=O)—NH—, ($C_1$-$C_{20}$)alkoxy-(C=O)—NH—, ($C_3$-$C_{25}$)heteroaryl-(C=O)—NH—, ($C_3$-$C_{25}$)heterocyclic-(C=O)—NH—, ($C_2$-$C_{20}$)alkenyl-(C=O)—NH—, ($C_3$-$C_{20}$)cycloalkenyl-(C=O)—NH—, ($C_2$-$C_{20}$)alkynyl-(C=O)—NH—, ($C_5$-$C_{20}$)cycloalkynyl-(C=O)—NH—, ($C_5$-$C_{25}$)aryl-(C=O)—NH—, perhalo($C_1$-$C_{20}$)alkyl-(C=O)—NH—, ($C_1$-$C_{20}$)alkyl-(C=O)—{(($C_1$-$C_{20}$)alkyl)N}—, phenyl-(C=O)—{(($C_1$-$C_{20}$)alkyl)N}—, ($C_3$-$C_{20}$)cycloalkyl-(C=O)—{(($C_1$-$C_{20}$)alkyl)N}—, ($C_1$-$C_{20}$)alkoxy-(C=O)—{(($C_1$-$C_{20}$)alkyl)N}—, ($C_3$-$C_{25}$)heteroaryl-(C=O)—{(($C_1$-$C_{20}$)alkyl)N}—, ($C_3$-$C_{25}$)heterocyclic-(C=O)—{(($C_1$-$C_{20}$)alkyl)N}—, ($C_2$-$C_{20}$)alkenyl-(C=O)—{(($C_1$-$C_{20}$)alkyl)N}—, ($C_3$-$C_{20}$)cycloalkenyl-(C=O)—{(($C_1$-$C_{20}$)alkyl)N}—, ($C_2$-$C_{20}$)alkynyl-(C=O)—{(($C_1$-$C_{20}$)alkyl)N}—, ($C_5$-$C_{20}$)cycloalkynyl-(C=O)—{(($C_1$-$C_{20}$)alkyl)N}—, ($C_5$-$C_{25}$)aryl-(C=O)—{(($C_1$-$C_{20}$)alkyl)N}—, perhalo($C_1$-$C_{20}$)alkyl-(C=O)—{(($C_1$-$C_{20}$)alkyl)N}—, phenyl-(C=O)—NH—, phenyl-(C=O)-{(phenyl)N}—, ($C_1$-$C_{20}$)alkyl-(C=O)-{(phenyl)N}—, ($C_3$-$C_{20}$)cycloalkyl-(C=O)-{(phenyl)N}—, ($C_1$-$C_{20}$)alkoxy-(C=O)-{(phenyl)N}—, ($C_3$-$C_{25}$)heteroaryl-(C=O)-{(phenyl)N}—, ($C_3$-$C_{25}$)heterocyclic-(C=O)-{(phenyl)N}—, ($C_2$-$C_{20}$)alkenyl-(C=O)-{(phenyl)N}—, ($C_3$-$C_{20}$)cycloalkenyl-(C=O)-{(phenyl)N}—, ($C_2$-$C_{20}$)alkynyl-(C=O)-{(phenyl)N}—, ($C_5$-$C_{20}$)cycloalkynyl-(C=O)-{(phenyl)N}—, ($C_5$-$C_{25}$)aryl-(C=O)-{(phenyl)N}—, perhalo($C_1$-$C_{20}$)alkyl-(C=O)-{(phenyl)N}—, $H_2$N(C=O)—, ($C_1$-$C_{20}$)alkyl-NH—(C=O)—, phenyl-NH—(C=O)—, ($C_3$-$C_{20}$)cycloalkyl-NH—(C=O)—, ($C_1$-$C_{20}$)alkoxy-NH—(C=O)—, ($C_3$-$C_{25}$)heteroaryl-NH—(C=O)—, ($C_3$-$C_{25}$)heterocyclic-NH—(C=O)—, ($C_2$-$C_{20}$)alkenyl-NH—(C=O)—, ($C_3$-$C_{20}$)cycloalkenyl-NH—(C=O)—, ($C_2$-$C_{20}$)alkynyl-NH—(C=O)—, ($C_5$-$C_{20}$)cycloalkynyl-NH—(C=O)—, ($C_5$-$C_{25}$)aryl-NH—(C=O)—, perhalo($C_1$-$C_{20}$)alkyl-NH—(C=O)—, {($C_1$-$C_{20}$)alkyl}$_2$N—(C=O)—, {phenyl}{($C_1$-$C_{20}$)alkyl}NH—(C=O)—, {($C_3$-$C_{20}$)cycloalkyl}{($C_1$-$C_{20}$)alkyl}N—(C=O)—, {($C_1$-$C_{20}$)alkoxy}{($C_1$-$C_{20}$)alkyl}N—(C=O)—, {($C_3$-$C_{25}$)heteroaryl}{($C_1$-$C_{20}$)alkyl}N—(C=O)—, {($C_3$-$C_{25}$)heterocyclic}{($C_1$-$C_{20}$)alkyl}N—(C=O)—, {($C_2$-$C_{20}$)alkenyl}{($C_1$-$C_{20}$)alkyl}N—(C=O)—, {($C_3$-$C_{20}$)cycloalkenyl}{($C_1$-$C_{20}$)alkyl}N—(C=O)—, {($C_2$-$C_{20}$)alkynyl}{($C_1$-$C_{20}$)alkyl}N—(C=O)—, {($C_5$-$C_{20}$)cycloalkynyl}{($C_1$-$C_{20}$)alkyl}N—(C=O)—, {($C_5$-$C_{25}$)aryl}{($C_1$-$C_{20}$)alkyl}N—(C=O)—, {perhalo($C_1$-$C_{20}$)alkyl}{($C_1$-$C_{20}$)alkyl}N—(C=O)—, {phenyl}$_2$N—(C=O)—, {($C_3$-$C_{20}$)cycloalkyl}{phenyl}N—(C=O)—, {($C_1$-$C_{20}$)alkoxy}{phenyl}N—(C=O)—, {($C_3$-$C_{25}$)heteroaryl}{phenyl}N—(C=O)—, {($C_3$-$C_{25}$)heterocyclic}{phenyl}N—(C=O)—, {($C_2$-$C_{20}$)alkenyl}{phenyl}N—(C=O)—, {($C_3$-$C_{20}$)cycloalkenyl}{phenyl}N—(C=O)—, {($C_2$-$C_{20}$)alkynyl}{phenyl}N—(C=O)—, {($C_5$-$C_{20}$)cycloalkynyl}{phenyl}N—(C=O)—, {($C_5$-$C_{25}$)aryl}{phenyl}N—(C=O)—, {perhalo($C_1$-$C_{20}$)alkyl}{phenyl}N—(C=O)—, HO—(C=O)—, ($C_1$-$C_{20}$)alkyl-(C=O)—, ($C_3$-$C_{25}$)heteroaryl-(C=O)—, ($C_3$-$C_{25}$)heterocyclic-(C=O)—, ($C_2$-$C_{20}$)alkenyl-(C=O)—, ($C_3$-$C_{20}$)cycloalkenyl-(C=O)—, ($C_2$-$C_{20}$)alkynyl-(C=O)—, ($C_5$-$C_{25}$)aryl-(C=O)—, perhalo($C_1$-$C_{20}$)alkyl-(C=O)—, phenyl-(C=O)—, ($C_1$-$C_{20}$)alkyl-O—(C=O)—, ($C_3$-$C_{25}$)heteroaryl-O—(C=O)—, ($C_3$-$C_{25}$)heterocyclic-O—(C=O)—, ($C_2$-$C_{20}$)alkenyl-O—(C=O)—, ($C_3$-$C_{20}$)cycloalkenyl-O—(C=O)—, ($C_2$-$C_{20}$)alkynyl-O—(C=O)—, ($C_5$-$C_{25}$)aryl-O—(C=O)—, perhalo($C_1$-$C_{20}$)alkyl-O—(C=O)—, phenyl-O—(C=O)—, ($C_1$-$C_{20}$)alkyl-(C=O)—O—, ($C_3$-$C_{25}$)heteroaryl-(C=O)—O—, ($C_3$-$C_{25}$)heterocyclic-(C=O)—O—, ($C_2$-$C_{20}$)alkenyl-(C=O)—O—, ($C_3$-$C_{20}$)cycloalkenyl-(C=O)—O—, ($C_2$-$C_{20}$)alkynyl-(C=O)—O—, ($C_5$-$C_{25}$)aryl-(C=O)—O—, phenyl-(C=O)—O—, perhalo($C_1$-$C_{20}$)alkyl-(C=O)—O—, and salts thereof;

wherein each of the aforesaid ($C_1$-$C_{20}$)alkyl, phenyl, ($C_3$-$C_{20}$)cycloalkyl, ($C_1$-$C_{20}$)alkoxy, ($C_3$-$C_{25}$)heteroaryl, ($C_3$-$C_{25}$)heterocyclic, ($C_2$-$C_{20}$)alkenyl, ($C_3$-$C_{20}$) cycloalkenyl, ($C_2$-$C_{20}$)alkynyl, ($C_5$-$C_{20}$)cycloalkynyl, and ($C_5$-$C_{25}$) aryl groups (as substituents on said alkylene, cycloalkylene or arylene of said Q and T) may be optionally and independently substituted by one to four moieties selected from the group consisting of hydroxy, halo, bromo, chloro, iodo, fluoro, —$N_3$, —CN, —NC, —SH, —$NO_2$, —$NH_2$, ($C_1$-$C_{20}$) alkyl, phenyl, ($C_3$-$C_{20}$)cycloalkyl, ($C_1$-$C_{20}$)alkoxy, ($C_3$-$C_{25}$) heteroaryl, ($C_3$-$C_{25}$)heterocyclic, ($C_2$-$C_{20}$)alkenyl, ($C_3$-$C_{20}$) cycloalkenyl, ($C_2$-$C_{20}$)alkynyl, ($C_5$-$C_{20}$)cycloalkynyl, ($C_5$-$C_{25}$)aryl, perhalo($C_1$-$C_{20}$)alkyl, ($C_1$-$C_{20}$)alkyl-O—, phenyl-O—, ($C_3$-$C_{20}$)cycloalkyl-O—, ($C_3$-$C_{25}$)heteroaryl-O—, ($C_3$-$C_{25}$)heterocyclic-O—, ($C_2$-$C_{20}$)alkenyl-O—, ($C_3$-$C_{20}$) cycloalkenyl-O—, ($C_2$-$C_{20}$)alkynyl-O—, ($C_5$-$C_{20}$)cycloalkynyl-O—, ($C_5$-$C_{25}$)aryl-O—, perhalo($C_1$-$C_{20}$)alkyl-O—, ($C_1$-$C_{20}$)alkyl-S—, phenyl-S—, ($C_3$-$C_{20}$)cycloalkyl-S—, ($C_3$-$C_{25}$)heteroaryl-S—, ($C_3$-$C_{25}$)heterocyclic-S—, ($C_2$-$C_{20}$)alkenyl-S—, ($C_3$-$C_{20}$)cycloalkenyl-S—, ($C_2$-$C_{20}$)alkynyl-S—, ($C_5$-$C_{20}$)cycloalkynyl-S—, ($C_5$-$C_{25}$)aryl-S—, perhalo($C_1$-$C_{20}$)alkyl-S—, ($C_1$-$C_{20}$)alkyl-$SO_2$—, phenyl-$SO_2$—, ($C_3$-$C_{20}$)cycloalkyl-$SO_2$—, ($C_1$-$C_{20}$)alkoxy-$SO_2$—, ($C_3$-$C_{25}$)heteroaryl-$SO_2$—, ($C_3$-$C_{25}$)heterocyclic-$SO_2$—, ($C_2$-$C_{20}$)alkenyl-$SO_2$—, ($C_3$-$C_{20}$)cycloalkenyl-$SO_2$—, ($C_2$-$C_{20}$)alkynyl-$SO_2$—, ($C_5$-$C_{20}$)cycloalkynyl-$SO_2$—, ($C_5$-$C_{25}$)aryl-$SO_2$—, perhalo($C_1$-$C_{20}$)alkyl-$SO_2$—, $H_2$N—$SO_2$—, ($C_1$-$C_{20}$)alkyl-NH—$SO_2$—, phenyl-NH—$SO_2$—, ($C_3$-$C_{20}$)cycloalkyl-NH—$SO_2$—, ($C_1$-$C_{20}$)alkoxy-NH—$SO_2$—, ($C_3$-$C_{25}$)heteroaryl-NH—$SO_2$—, ($C_3$-$C_{25}$)heterocyclic-NH—$SO_2$—, ($C_2$-$C_{20}$)alkenyl-NH—$SO_2$—, ($C_3$-$C_{20}$ cycloalkenyl-NH—SO$_2$—, (C$_2$-C$_{20}$)alkynyl-NH—SO$_2$—, (C$_5$-C$_{20}$)cycloalkynyl-NH—SO$_2$—, (C$_5$-C$_{25}$)aryl-NH—SO$_2$—, perhalo(C$_1$-C$_{20}$)alkyl-NH—SO$_2$—, {(C$_1$-C$_{20}$)alkyl}$_2$N—SO$_2$—, {phenyl}$_2$N—SO$_2$—, {(C$_3$-C$_{20}$)cycloalkyl}$_2$N—SO$_2$—, {(C$_1$-C$_{20}$)alkoxy}$_2$N—SO$_2$—, {(C$_3$-C$_{25}$)heteroaryl}$_2$N—SO$_2$—, {(C$_3$-C$_{25}$)heterocyclic}$_2$N—SO$_2$—, {(C$_2$-C$_{20}$)alkenyl}$_2$N—SO$_2$—, {(C$_2$-C$_{20}$)alkynyl}$_2$N—SO$_2$—, {(C$_5$-C$_{20}$)cycloalkynyl}$_2$N—SO$_2$—, {(C$_5$-C$_{25}$)aryl}$_2$N—SO$_2$—, {perhalo(C$_1$-C$_{20}$)alkyl}$_2$N—SO$_2$—, (C$_1$-C$_{20}$)alkyl-SO$_2$—NH—, phenyl-SO$_2$—NH—, (C$_3$-C$_{20}$)cycloalkyl-SO$_2$—NH—, (C$_1$-C$_{20}$)alkoxy-SO$_2$—NH—, (C$_3$-C$_{25}$)heteroaryl-SO$_2$—NH—, (C$_3$-C$_{25}$)heterocyclic-SO$_2$—NH—, (C$_2$-C$_{20}$)alkenyl-SO$_2$—NH—, (C$_3$-C$_{20}$)cycloalkenyl-SO$_2$—NH—, (C$_2$-C$_{20}$)alkynyl-SO$_2$—NH—, (C$_5$-C$_{20}$)cycloalkynyl-SO$_2$—NH—, (C$_5$-C$_{25}$)aryl-SO$_2$—NH—, perhalo(C$_1$-C$_{20}$)alkyl-SO$_2$—NH—, (C$_1$-C$_{20}$)alkyl-NH—, phenyl-NH—, (C$_3$-C$_{20}$)cycloalkyl-NH—, (C$_1$-C$_{20}$)alkoxy-NH—, (C$_3$-C$_{25}$)heteroaryl-NH—, (C$_3$-C$_{25}$)heterocyclic-NH—, (C$_2$-C$_{20}$)alkenyl-NH—, (C$_3$-C$_{20}$)cycloalkenyl-NH—, (C$_2$-C$_{20}$)alkynyl-NH—, (C$_5$-C$_{20}$)cycloalkynyl-NH—, (C$_5$-C$_{25}$)aryl-NH—, perhalo(C$_1$-C$_{20}$)alkyl-NH—, {(C$_1$-C$_{20}$)alkyl}$_2$N—, {phenyl}$_2$N—, {(C$_3$-C$_{20}$)cycloalkyl}$_2$N—, {(C$_1$-C$_{20}$)alkoxy}$_2$N—, {(C$_3$-C$_{25}$)heteroaryl}$_2$N—, {(C$_3$-C$_{25}$)heterocyclic}$_2$N—, {(C$_2$-C$_{20}$)alkenyl}$_2$N—, {(C$_3$-C$_{20}$)cycloalkenyl}$_2$N—, {(C$_2$-C$_{20}$)alkynyl}$_2$N—, {(C$_5$-C$_{20}$)cycloalkynyl}$_2$N—, {(C$_5$-C$_{25}$)aryl}$_2$N—, {perhalo(C$_1$-C$_{20}$)alkyl}$_2$N—, (C$_1$-C$_{20}$)alkyl-(C=O)—NH—, phenyl-(C=O)—NH—, (C$_3$-C$_{20}$)cycloalkyl-(C=O)—NH—, (C$_1$-C$_{20}$)alkoxy-(C=O)—NH—, (C$_3$-C$_{25}$)heteroaryl-(C=O)—NH—, (C$_3$-C$_{25}$)heterocyclic-(C=O)—NH—, (C$_2$-C$_{20}$)alkenyl-(C=O)—NH—, (C$_3$-C$_{20}$)cycloalkenyl-(C=O)—NH—, (C$_2$-C$_{20}$)alkynyl-(C=O)—NH—, (C$_5$-C$_{20}$)cycloalkynyl-(C=O)—NH—, (C$_5$-C$_{25}$)aryl-(C=O)—NH—, perhalo(C$_1$-C$_{20}$)alkyl-(C=O)—NH—, (C$_1$-C$_{20}$)alkyl-(C=O)-{((C$_1$-C$_{20}$)alkyl)N}—, phenyl-(C=O)-{((C$_1$-C$_{20}$)alkyl)N}—, (C$_3$-C$_{20}$)cycloalkyl-(C=O)-{((C$_1$-C$_{20}$)alkyl)N}—, (C$_1$-C$_{20}$)alkoxy-(C=O)-{((C$_1$-C$_{20}$)alkyl)N}—, (C$_3$-C$_{25}$)heteroaryl-(C=O)-{((C$_1$-C$_{20}$)alkyl)N}—, (C$_3$-C$_{25}$)heterocyclic-(C=O)-{((C$_1$-C$_{20}$)alkyl)N}—, (C$_2$-C$_{20}$)alkenyl-(C=O)-{((C$_1$-C$_{20}$)alkyl)N}—, (C$_3$-C$_{20}$)cycloalkenyl-(C=O)-{((C$_1$-C$_{20}$)alkyl)N}—, (C$_2$-C$_{20}$)alkynyl-(C=O)-{((C$_1$-C$_{20}$)alkyl)N}—, (C$_5$-C$_{20}$)cycloalkynyl-(C=O)-{((C$_1$-C$_{20}$)alkyl)N}—, (C$_5$-C$_{25}$)aryl-(C=O){((C$_1$-C$_{20}$)alkyl)N}—, perhalo(C$_1$-C$_{20}$)alkyl-(C=O)-{((C$_1$-C$_{20}$)alkyl)N}—, phenyl-(C=O)—NH—, phenyl-(C=O)-{(phenyl)N}—, (C$_1$-C$_{20}$)alkyl-(C=O)-{(phenyl)N}—, (C$_3$-C$_{20}$)cycloalkyl-(C=O)-{(phenyl)N}—, (C$_1$-C$_{20}$)alkoxy-(C=O)-{(phenyl)N}—, (C$_3$-C$_{25}$)heteroaryl-(C=O)-{(phenyl)N}—, (C$_3$-C$_{25}$)heterocyclic-(C=O)-{(phenyl)N}—, (C$_2$-C$_{20}$)alkenyl-(C=O)-{(phenyl)N}—, (C$_3$-C$_{20}$)cycloalkenyl-(C=O)-{(phenyl)N}—, (C$_2$-C$_{20}$)alkynyl-(C=O)-{(phenyl)N}—, (C$_5$-C$_{20}$)cycloalkynyl-(C=O)-{(phenyl)N}—, (C$_5$-C$_{25}$)aryl-(C=O)-{(phenyl)N}—, perhalo(C$_1$-C$_{20}$)alkyl-(C=O)-{(phenyl)N}—, H$_2$N(C=O)—, (C$_1$-C$_{20}$)alkyl-NH—(C=O)—, phenyl-NH—(C=O)—, (C$_3$-C$_{20}$)cycloalkyl-NH—(C=O)—, (C$_1$-C$_{20}$)alkoxy-NH—(C=O)—, (C$_3$-C$_{25}$)heteroaryl-NH—(C=O)—, (C$_3$-C$_{25}$)heterocyclic-NH—(C=O)—, (C$_2$-C$_{20}$)alkenyl-NH—(C=O)—, (C$_3$-C$_{20}$)cycloalkenyl-NH—(C=O)—, (C$_2$-C$_{20}$)alkynyl-NH—(C=O)—, (C$_5$-C$_{20}$)cycloalkynyl-NH—(C=O)—, (C$_5$-C$_{25}$)aryl-NH—(C=O)—, perhalo(C$_1$-C$_{20}$)alkyl-NH—(C=O)—, {(C$_1$-C$_{20}$)alkyl}$_2$N—(C=O)—, {phenyl}{(C$_1$-C$_{20}$)alkyl}N—(C=O)—, {(C$_3$-C$_{20}$)cycloalkyl}{(C$_1$-C$_{20}$)alkyl}N—(C=O)—, {(C$_1$-C$_{20}$)alkoxy}{(C$_1$-C$_{20}$)alkyl}N—(C=O)—, {(C$_3$-C$_{25}$)heteroaryl}{(C$_1$-C$_{20}$)alkyl}N—(C=O)—, {(C$_3$-C$_{25}$)heterocyclic}{(C$_1$-C$_{20}$)alkyl}N—(C=O)—, {(C$_2$-C$_{20}$)alkenyl}{(C$_1$-C$_{20}$)alkyl}N—(C=O)—, {(C$_3$-C$_{20}$)cycloalkenyl}{(C$_1$-C$_{20}$)alkyl}N—(C=O)—, {(C$_2$-C$_{20}$)alkynyl}{(C$_1$-C$_{20}$)alkyl}N—(C=O)—, {(C$_5$-C$_{20}$)cycloalkynyl}{(C$_1$-C$_{20}$)alkyl}N—(C=O)—, {(C$_5$-C$_{25}$)aryl}{(C$_1$-C$_{20}$)alkyl}N—(C=O)—, {perhalo(C$_1$-C$_{20}$)alkyl}{(C$_1$-C$_{20}$)alkyl}N—(C=O)—, {phenyl}$_2$N—(C=O)—, {(C$_3$-C$_{20}$)cycloalkyl}{phenyl}N—(C=O)—, {(C$_1$-C$_{20}$)alkoxy}{phenyl}N—(C=O)—, {(C$_3$-C$_{25}$)heteroaryl}{phenyl}N—(C=O)—, {(C$_3$-C$_{25}$)heterocyclic}{phenyl}N—(C=O)—, {(C$_2$-C$_{20}$)alkenyl}{phenyl}N—(C=O)—, {(C$_3$-C$_{20}$)cycloalkenyl}{phenyl}N—(C=O)—, {(C$_2$-C$_{20}$)alkynyl}{phenyl}N—(C=O)—, {(C$_5$-C$_{20}$)cycloalkynyl}{phenyl}N—(C=O)—, {(C$_5$-C$_{25}$)aryl}{phenyl}N—(C=O)—, {perhalo(C$_1$-C$_{20}$)alkyl}{phenyl}N—(C=O)—, HO—(C=O)—, (C$_1$-C$_{20}$)alkyl-(C=O)—, (C$_3$-C$_{25}$)heteroaryl-(C=O)—, (C$_3$-C$_{25}$)heterocyclic-(C=O)—, (C$_2$-C$_{20}$)alkenyl-(C=O)—, (C$_3$-C$_{20}$)cycloalkenyl-(C=O)—, (C$_2$-C$_{20}$)alkynyl-(C=O)—, (C$_5$-C$_{25}$)aryl-(C=O)—, perhalo(C$_1$-C$_{20}$)alkyl-(C=O)—, phenyl-(C=O)—, (C$_1$-C$_{20}$)alkyl-O—(C=O)—, (C$_3$-C$_{25}$)heteroaryl-O—(C=O)—, (C$_3$-C$_{25}$)heterocyclic-O—(C=O)—, (C$_2$-C$_{20}$)alkenyl-O—(C=O)—, (C$_3$-C$_{20}$)cycloalkenyl-O—(C=O)—, (C$_2$-C$_{20}$)alkynyl-O—(C=O)—, (C$_5$-C$_{25}$)aryl-O—(C=O)—, perhalo(C$_1$-C$_{20}$)alkyl-O—(C=O)—, phenyl-O—(C=O)—, (C$_1$-C$_{20}$)alkyl-(C=O)—O—, (C$_3$-C$_{25}$)heteroaryl-(C=O)—O—, (C$_3$-C$_{25}$)heterocyclic-(C=O)—O—, (C$_2$-C$_{20}$)alkenyl-(C=O)—O—, (C$_3$-C$_{20}$)cycloalkenyl-(C=O)—O—, (C$_2$-C$_{20}$)alkynyl-(C=O)—O—, (C$_5$-C$_{25}$)aryl-(C=O)—O—, phenyl-(C=O)—O—, perhalo(C$_1$-C$_{20}$)alkyl-(C=O)—O—, and salts thereof; and wherein R$^2$, R$^3$, R$^4$, R$^5$, R$^6$, R$^7$, R$^8$, R$^9$, R$^{10}$, and R$^{11}$ are each independently selected from the group consisting of hydrogen, hydroxy, halo, bromo, chloro, iodo, fluoro, —N$_3$, —CN, —NC, —SH, —NO$_2$, —NH$_2$, (C$_1$-C$_{20}$)alkyl, phenyl, (C$_3$-C$_{20}$)cycloalkyl, (C$_1$-C$_{20}$)alkoxy, (C$_3$-C$_{25}$)heteroaryl, (C$_3$-C$_{25}$)heterocyclic, (C$_2$-C$_{20}$)alkenyl, (C$_3$-C$_{20}$)cycloalkenyl, (C$_2$-C$_{20}$)alkynyl, (C$_5$-C$_{20}$)cycloalkynyl, (C$_5$-C$_{25}$)aryl, perhalo(C$_1$-C$_{20}$)alkyl, (C$_1$-C$_{20}$)alkyl-O—, phenyl-O—, (C$_3$-C$_{20}$)cycloalkyl-O—, (C$_3$-C$_{25}$)heteroaryl-O—, (C$_3$-C$_{25}$)heterocyclic-O—, (C$_2$-C$_{20}$)alkenyl-O—, (C$_3$-C$_{20}$)cycloalkenyl-O—, (C$_2$-C$_{20}$)alkynyl-O—, (C$_5$-C$_{20}$)cycloalkynyl-O—, (C$_5$-C$_{25}$)aryl-O—, perhalo(C$_1$-C$_{20}$)alkyl-O—, (C$_1$-C$_{20}$)alkyl-S—, phenyl-S—, (C$_3$-C$_{20}$)cycloalkyl-S—, (C$_3$-C$_2$)heteroaryl-S—, (C$_3$-C$_{25}$)heterocyclic-S—, (C$_2$-C$_{20}$)alkenyl-S—, (C$_3$-C$_{20}$)cycloalkenyl-S—, (C$_2$-C$_{20}$)alkynyl-S—, (C$_5$-C$_{20}$)cycloalkynyl-S—, (C$_5$-C$_{25}$)aryl-S—, perhalo(C$_1$-C$_{20}$)alkyl-S—, (C$_1$-C$_{20}$)alkyl-SO$_2$—, phenyl-SO$_2$—, (C$_3$-C$_{20}$)cycloalkyl-SO$_2$—, (C$_1$-C$_{20}$)alkoxy-SO$_2$—, (C$_3$-C$_{25}$)heteroaryl-SO$_2$—, (C$_3$-C$_{25}$)heterocyclic-SO$_2$—, (C$_2$-C$_{20}$)alkenyl-SO$_2$—, (C$_3$-C$_{20}$)cycloalkenyl-SO$_2$—, (C$_2$-C$_{20}$)alkynyl-SO$_2$—, (C$_5$-C$_{20}$)cycloalkynyl-SO$_2$—, (C$_5$-C$_{25}$)aryl-SO$_2$—, perhalo(C$_1$-C$_{20}$)alkyl-SO$_2$—, H$_2$N—SO$_2$—, (C$_1$-C$_{20}$)alkyl-NH—SO$_2$—, phenyl-NH—SO$_2$—, (C$_3$-C$_{20}$)cycloalkyl-NH—SO$_2$—, (C$_1$-C$_{20}$)alkoxy-NH—SO$_2$—, (C$_3$-C$_{25}$)heteroaryl-NH—SO$_2$—, (C$_3$-C$_{25}$)heterocyclic-NH—SO$_2$—, (C$_2$-C$_{20}$)alkenyl-NH—SO$_2$—, (C$_3$-C$_{20}$)cycloalkenyl-NH—SO$_2$—, (C$_2$-C$_{20}$)alkynyl-NH—SO$_2$—, (C$_5$-C$_{20}$)cycloalkynyl-NH—SO$_2$—, (C$_5$-C$_{25}$)aryl-NH—SO$_2$—, perhalo(C$_1$-C$_{20}$)alkyl-NH—SO$_2$—, {(C$_1$-C$_{20}$)alkyl}$_2$N—SO$_2$—, {phenyl}$_2$N—SO$_2$—, {(C$_3$-C$_{20}$)cycloalkyl}$_2$N—SO$_2$—, {(C$_1$-C$_{20}$)alkoxy}$_2$N—SO$_2$—, {(C$_3$-C$_{25}$)heteroaryl}$_2$N—SO$_2$—, {(C$_3$-C$_{25}$)heterocyclic}$_2$N—SO$_2$—, {(C$_2$-C$_{20}$)alkenyl}$_2$N—SO$_2$—, {($C_2$-$C_{20}$)alkynyl}$_2$N—$SO_2$—, {($C_5$-$C_{20}$)cycloalkynyl}$_2$N—$SO_2$—, {($C_5$-$C_{25}$)aryl}$_2$N—$SO_2$—, {perhalo($C_1$-$C_{20}$)alkyl}$_2$N—$SO_2$—, ($C_1$-$C_{20}$)alkyl-$SO_2$—NH—, phenyl-$SO_2$—NH—, ($C_3$-$C_{20}$)cycloalkyl-$SO_2$—NH—, ($C_1$-$C_{20}$)alkoxy-$SO_2$—NH—, ($C_3$-$C_{25}$)heteroaryl-$SO_2$—NH—, ($C_3$-$C_{25}$)heterocyclic-$SO_2$—NH—, ($C_2$-$C_{20}$)alkenyl-$SO_2$—NH—, ($C_3$-$C_{20}$)cycloalkenyl-$SO_2$—NH—, ($C_2$-$C_{20}$)alkynyl-$SO_2$—NH—, ($C_5$-$C_{20}$)cycloalkynyl-$SO_2$—NH—, ($C_5$-$C_{25}$)aryl-$SO_2$—NH—, perhalo($C_1$-$C_{20}$)alkyl-$SO_2$—NH—, ($C_1$-$C_{20}$)alkyl-NH—, phenyl-NH—, ($C_3$-$C_{20}$)cycloalkyl-NH—, ($C_1$-$C_{20}$)alkoxy-NH—, ($C_3$-$C_{25}$)heteroaryl-NH—, ($C_3$-$C_{25}$)heterocyclic-NH—, ($C_2$-$C_{20}$)alkenyl-NH—, ($C_3$-$C_{20}$)cycloalkenyl-NH—, ($C_2$-$C_{20}$)alkynyl-NH—, ($C_5$-$C_{20}$)cycloalkynyl-NH—, ($C_5$-$C_{25}$)aryl-NH—, perhalo($C_1$-$C_{20}$)alkyl-NH—, {($C_1$-$C_{20}$)alkyl}$_2$N—, {phenyl}$_2$N—, {($C_3$-$C_{20}$)cycloalkyl}$_2$N—, {($C_1$-$C_{20}$)alkoxy}$_2$N—, {($C_3$-$C_{25}$)heteroaryl}$_2$N—, {($C_3$-$C_{25}$)heterocyclic}$_2$N—, {($C_2$-$C_{20}$)alkenyl}$_2$N—, {($C_3$-$C_{20}$)cycloalkenyl}$_2$N—, {($C_2$-$C_{20}$)alkynyl}$_2$N—, {($C_5$-$C_{20}$)cycloalkynyl}$_2$N—, {($C_5$-$C_{25}$)aryl}$_2$N—, {perhalo($C_1$-$C_{20}$)alkyl}$_2$N—, ($C_1$-$C_{20}$)alkyl-(C=O)—NH—, phenyl-(C=O)—NH—, ($C_3$-$C_{20}$)cycloalkyl-(C=O)—NH—, ($C_1$-$C_{20}$)alkoxy-(C=O)—NH—, ($C_3$-$C_{25}$)heteroaryl-(C=O)—NH—, ($C_3$-$C_{25}$)heterocyclic-(C=O)—NH—, ($C_2$-$C_{20}$)alkenyl-(C=O)—NH—, ($C_3$-$C_{20}$)cycloalkenyl-(C=O)—NH—, ($C_2$-$C_{20}$)alkynyl-(C=O)—NH—, ($C_5$-$C_{20}$)cycloalkynyl-(C=O)—NH—, ($C_5$-$C_{25}$)aryl-(C=O)—NH—, perhalo($C_1$-$C_{20}$)alkyl-(C=O)—NH—, ($C_1$-$C_{20}$)alkyl-(C=O)—{(($C_1$-$C_{20}$)alkyl)N}—, phenyl-(C=O)—{(($C_1$-$C_{20}$)alkyl)N}—, ($C_3$-$C_{20}$)cycloalkyl-(C=O)—{(($C_1$-$C_{20}$)alkyl)N}—, ($C_1$-$C_{20}$)alkoxy-(C=O)—{(($C_1$-$C_{20}$)alkyl)N}—, ($C_3$-$C_{25}$)heteroaryl-(C=O)—{(($C_1$-$C_{20}$)alkyl)N}—, ($C_3$-$C_{25}$)heterocyclic-(C=O)—{(($C_1$-$C_{20}$)alkyl)N}—, ($C_2$-$C_{20}$)alkenyl-(C=O)—{(($C_1$-$C_{20}$)alkyl)N}—, ($C_3$-$C_{20}$)cycloalkenyl-(C=O)—{(($C_1$-$C_{20}$)alkyl)N}—, ($C_2$-$C_{20}$)alkynyl-(C=O)—{(($C_1$-$C_{20}$)alkyl)N}—, ($C_5$-$C_{20}$)cycloalkynyl-(C=O)—{(($C_1$-$C_{20}$)alkyl)N}—, ($C_5$-$C_{25}$)aryl-(C=O)—{(($C_1$-$C_{20}$)alkyl)N}—, perhalo($C_1$-$C_{20}$)alkyl-(C=O)—{(($C_1$-$C_{20}$)alkyl)N}—, phenyl-(C=O)—NH—, phenyl-(C=O)-{(phenyl)N}—, ($C_1$-$C_{20}$)alkyl-(C=O)-{(phenyl)N}—, ($C_3$-$C_{20}$)cycloalkyl-(C=O)-{(phenyl)N}—, ($C_1$-$C_{20}$)alkoxy-(C=O)-{(phenyl)N}—, ($C_3$-$C_{25}$)heteroaryl-(C=O)-{(phenyl)N}—, ($C_3$-$C_{25}$)heterocyclic-(C=O)-{(phenyl)N}—, ($C_2$-$C_{20}$)alkenyl-(C=O)-{(phenyl)N}—, ($C_3$-$C_{20}$)cycloalkenyl-(C=O)-{(phenyl)N}—, ($C_2$-$C_{20}$)alkynyl-(C=O)-{(phenyl)N}—, ($C_5$-$C_{20}$)cycloalkynyl-(C=O)-{(phenyl)N}—, ($C_5$-$C_{25}$)aryl-(C=O)-{(phenyl)N}—, perhalo($C_1$-$C_{20}$)alkyl-(C=O)-{(phenyl)N}—, $H_2$N(C=O)—, ($C_1$-$C_{20}$)alkyl-NH—(C=O)—, phenyl-NH—(C=O)—, ($C_3$-$C_{20}$)cycloalkyl-NH—(C=O)—, ($C_1$-$C_{20}$)alkoxy-NH—(C=O)—, ($C_3$-$C_{25}$)heteroaryl-NH—(C=O)—, ($C_3$-$C_{25}$)heterocyclic-NH—(C=O)—, ($C_2$-$C_{20}$)alkenyl-NH—(C=O)—, ($C_3$-$C_{20}$)cycloalkenyl-NH—(C=O)—, ($C_2$-$C_{20}$)alkynyl-NH—(C=O)—, ($C_5$-$C_{20}$)cycloalkynyl-NH—(C=O)—, ($C_5$-$C_{25}$)aryl-NH—(C=O)—, perhalo($C_1$-$C_{20}$)alkyl-NH—(C=O)—, {($C_1$-$C_{20}$)alkyl}$_2$N—(C=O)—, {phenyl}{($C_1$-$C_{20}$)alkyl}N—(C=O)—, {($C_3$-$C_{20}$)cycloalkyl}{($C_1$-$C_{20}$)alkyl}N—(C=O)—, {($C_1$-$C_{20}$)alkoxy}{($C_1$-$C_{20}$)alkyl}N—(C=O)—, {($C_3$-$C_{25}$)heteroaryl}{($C_1$-$C_{20}$)alkyl}N—(C=O)—, {($C_3$-$C_{25}$)heterocyclic}{($C_1$-$C_{20}$)alkyl}N—(C=O)—, {($C_2$-$C_{20}$)alkenyl}{($C_1$-$C_{20}$)alkyl}N—(C=O)—, {($C_3$-$C_{20}$)cycloalkenyl}{($C_1$-$C_{20}$)alkyl}N—(C=O)—, {($C_2$-$C_{20}$)alkynyl}{($C_1$-$C_{20}$)alkyl}N—(C=O)—, {($C_5$-$C_{20}$)cycloalkynyl}{($C_1$-$C_{20}$)alkyl}N—(C=O)—, {($C_5$-$C_{25}$)aryl}{($C_1$-$C_{20}$)alkyl}N—(C=O)—, {perhalo($C_1$-$C_{20}$)alkyl}{($C_1$-$C_{20}$)alkyl}N—(C=O)—, {phenyl}$_2$N—(C=O)—, {($C_3$-$C_{20}$)cycloalkyl}{phenyl}N—(C=O)—, {($C_1$-$C_{20}$)alkoxy}{phenyl}N—(C=O)—, {($C_3$-$C_{25}$)heteroaryl}{phenyl}N—(C=O)—, {($C_3$-$C_{25}$)heterocyclic}{phenyl}N—(C=O)—, {($C_2$-$C_{20}$)alkenyl}{phenyl}N—(C=O)—, {($C_3$-$C_{20}$)cycloalkenyl}{phenyl}N—(C=O)—, {($C_2$-$C_{20}$)alkynyl}{phenyl}N—(C=O)—, {($C_5$-$C_{20}$)cycloalkynyl}{phenyl}N—(C=O)—, {($C_5$-$C_{25}$)aryl}{phenyl}N—(C=O)—, {perhalo($C_1$-$C_{20}$)alkyl}{phenyl}N—(C=O)—, HO—(C=O)—, ($C_1$-$C_{20}$)alkyl-(C=O)—, ($C_3$-$C_{25}$)heteroaryl-(C=O)—, ($C_3$-$C_{25}$)heterocyclic-(C=O)—, ($C_2$-$C_{20}$)alkenyl-(C=O)—, ($C_3$-$C_{20}$)cycloalkenyl-(C=O)—, ($C_2$-$C_{20}$)alkynyl-(C=O)—, ($C_5$-$C_{25}$)aryl-(C=O)—, perhalo($C_1$-$C_{20}$)alkyl-(C=O)—, phenyl-(C=O)—, ($C_1$-$C_{20}$)alkyl-O—(C=O)—, ($C_3$-$C_{25}$)heteroaryl-O—(C=O)—, ($C_3$-$C_{25}$)heterocyclic-O—(C=O)—, ($C_2$-$C_{20}$)alkenyl-O—(C=O)—, ($C_3$-$C_{20}$)cycloalkenyl-O—(C=O)—, ($C_2$-$C_{20}$)alkynyl-O—(C=O)—, ($C_5$-$C_{25}$)aryl-O—(C=O)—, perhalo($C_1$-$C_{20}$)alkyl-O—(C=O)—, phenyl-O—(C=O)—, ($C_1$-$C_{20}$)alkyl-(C=O)—O—, ($C_3$-$C_{25}$)heteroaryl-(C=O)—O—, ($C_3$-$C_{25}$)heterocyclic-(C=O)—O—, ($C_2$-$C_{20}$)alkenyl-(C=O)—O—, ($C_3$-$C_{20}$)cycloalkenyl-(C=O)—O—, ($C_2$-$C_{20}$)alkynyl-(C=O)—O—, ($C_5$-$C_{25}$)aryl-(C=O)—O—, phenyl-(C=O)—O—, perhalo($C_1$-$C_{20}$)alkyl-(C=O)—O—, and salts thereof;

wherein each of the aforesaid ($C_1$-$C_{20}$)alkyl, phenyl, ($C_3$-$C_{20}$)cycloalkyl, ($C_1$-$C_{20}$)alkoxy, ($C_3$-$C_{25}$)heteroaryl, ($C_3$-$C_{25}$)heterocyclic, ($C_2$-$C_{20}$)alkenyl, ($C_3$-$C_{20}$) cycloalkenyl, ($C_2$-$C_{20}$)alkynyl, ($C_5$-$C_{20}$)cycloalkynyl, and ($C_5$-$C_{25}$) aryl groups (for said $R^2$, $R^3$, $R^4$, $R^5$, $R^6$, $R^7$, $R^8$, $R^9$, $R^{10}$, and $R^{11}$ groups) may be optionally and independently substituted by one to four moieties selected from the group consisting of hydroxy, halo, bromo, chloro, iodo, fluoro, —$N_3$, —CN, —NC, —SH, —$NO_2$, —$NH_2$, ($C_1$-$C_{20}$)alkyl, phenyl, ($C_3$-$C_{20}$)cycloalkyl, ($C_1$-$C_{20}$)alkoxy, ($C_3$-$C_{25}$)heteroaryl, ($C_3$-$C_{25}$)heterocyclic, ($C_2$-$C_{20}$)alkenyl, ($C_3$-$C_{20}$)cycloalkenyl, ($C_2$-$C_{20}$)alkynyl, ($C_5$-$C_{20}$)cycloalkynyl, ($C_5$-$C_{25}$)aryl, perhalo($C_1$-$C_{20}$)alkyl, ($C_1$-$C_{20}$)alkyl-O—, phenyl-O—, ($C_3$-$C_{20}$)cycloalkyl-O—, ($C_3$-$C_{25}$)heteroaryl-O—, ($C_3$-$C_{25}$)heterocyclic-O—, ($C_2$-$C_{20}$)alkenyl-O—, ($C_3$-$C_{20}$)cycloalkenyl-O—, ($C_2$-$C_{20}$)alkynyl-O—, ($C_5$-$C_{20}$)cycloalkynyl-O—, ($C_5$-$C_{25}$)aryl-O—, perhalo($C_1$-$C_{20}$)alkyl-O—, ($C_1$-$C_{20}$)alkyl-S—, phenyl-S—, ($C_3$-$C_{20}$)cycloalkyl-S—, ($C_3$-$C_{25}$)heteroaryl-S—, ($C_3$-$C_{25}$)heterocyclic-S—, ($C_2$-$C_{20}$)alkenyl-S—, ($C_3$-$C_{20}$)cycloalkenyl-S—, alkynyl-S—, ($C_5$-$C_{20}$)cycloalkynyl-S—, ($C_5$-$C_{25}$)aryl-S—, perhalo($C_1$-$C_{20}$)alkyl-S—, ($C_1$-$C_{20}$)alkyl-$SO_2$—, phenyl-$SO_2$—, ($C_3$-$C_{20}$)cycloalkyl-$SO_2$—, ($C_1$-$C_{20}$)alkoxy-$SO_2$—, ($C_3$-$C_{25}$)heteroaryl-$SO_2$—, ($C_3$-$C_{25}$)heterocyclic-$SO_2$—, ($C_2$-$C_{20}$)alkenyl-$SO_2$—, ($C_3$-$C_{20}$)cycloalkenyl-$SO_2$—, ($C_2$-$C_{20}$)alkynyl-$SO_2$—, ($C_5$-$C_{20}$)cycloalkynyl-$SO_2$—, ($C_5$-$C_{25}$)aryl-$SO_2$—, perhalo($C_1$-$C_{20}$)alkyl-$SO_2$—, $H_2$N—$SO_2$—, ($C_1$-$C_{20}$)alkyl-NH—$SO_2$—, phenyl-NH—$SO_2$—, ($C_3$-$C_{20}$)cycloalkyl-NH—$SO_2$—, ($C_1$-$C_{20}$)alkoxy-NH—$SO_2$—, ($C_3$-$C_{25}$)heteroaryl-NH—$SO_2$—, ($C_3$-$C_{25}$)heterocyclic-NH—$SO_2$—, ($C_2$-$C_{20}$)alkenyl-NH—$SO_2$—, ($C_3$-$C_{20}$)cycloalkenyl-NH—$SO_2$—, ($C_2$-$C_{20}$)alkynyl-NH—$SO_2$—, ($C_5$-$C_{20}$)cycloalkynyl-NH—$SO_2$—, ($C_5$-$C_{25}$)aryl-NH—$SO_2$—, perhalo($C_1$-$C_{20}$)alkyl-NH—$SO_2$—, {($C_1$-$C_{20}$)alkyl}$_2$N—$SO_2$—, {phenyl}$_2$N—$SO_2$—, {($C_3$-$C_{20}$)cycloalkyl}$_2$N—$SO_2$—, {($C_1$-$C_{20}$)alkoxy}$_2$N—$SO_2$—, {($C_3$-$C_{25}$)heteroaryl}$_2$N—$SO_2$—, {($C_3$-$C_{25}$)heterocyclic}$_2$N—$SO_2$—, {($C_2$-$C_{20}$)alkenyl}$_2$N—$SO_2$—, {($C_2$-$C_{20}$)alkynyl}$_2$N—$SO_2$—, {($C_5$-$C_{20}$)cycloalkynyl}$_2$N—$SO_2$—, {($C_5$-$C_{25}$)aryl}$_2$N—$SO_2$—, {perhalo(C$_1$-C$_{20}$)alkyl}$_2$N—SO$_2$—, (C$_1$-C$_{20}$)alkyl-SO$_2$—NH—, phenyl-SO$_2$—NH—, (C$_3$-C$_{20}$)cycloalkyl-SO$_2$—NH—, (C$_1$-C$_{20}$)alkoxy-SO$_2$—NH—, (C$_3$-C$_{25}$)heteroaryl-SO$_2$—NH—, (C$_3$-C$_{25}$)heterocyclic-SO$_2$—NH—, (C$_2$-C$_{20}$)alkenyl-SO$_2$—NH—, (C$_3$-C$_{20}$)cycloalkenyl-SO$_2$—NH—, (C$_2$-C$_{20}$)alkynyl-SO$_2$—NH—, (C$_5$-C$_{20}$)cycloalkynyl-SO$_2$—NH—, (C$_5$-C$_{25}$)aryl-SO$_2$—NH—, perhalo(C$_1$-C$_{20}$)alkyl-SO$_2$—NH—, (C$_1$-C$_{20}$)alkyl-NH—, phenyl-NH—, (C$_3$-C$_{20}$)cycloalkyl-NH—, (C$_1$-C$_{20}$)alkoxy-NH—, (C$_3$-C$_{25}$)heteroaryl-NH—, (C$_3$-C$_{25}$)heterocyclic-NH—, (C$_2$-C$_{20}$)alkenyl-NH—, (C$_3$-C$_{20}$)cycloalkenyl-NH—, (C$_2$-C$_{20}$)alkynyl-NH—, (C$_5$-C$_{20}$)cycloalkynyl-NH—, (C$_5$-C$_{25}$)aryl-NH—, perhalo(C$_1$-C$_{20}$)alkyl-NH—, {(C$_1$-C$_{20}$)alkyl}$_2$N—, {phenyl}$_2$N—, {(C$_3$-C$_{20}$)cycloalkyl}$_2$N—, {(C$_1$-C$_{20}$)alkoxy}$_2$N—, {(C$_3$-C$_2$)heteroaryl}$_2$N—, {(C$_3$-C$_{25}$)heterocyclic}$_2$N—, {(C$_2$-C$_{20}$)alkenyl}$_2$N—, {(C$_3$-C$_{20}$)cycloalkenyl}$_2$N—, {(C$_2$-C$_{20}$)alkynyl}$_2$N—, {(C$_5$-C$_{20}$)cycloalkynyl}$_2$N—, {(C$_5$-C$_{25}$)aryl}$_2$N—, {perhalo(C$_1$-C$_{20}$)alkyl}$_2$N—, (C$_1$-C$_{20}$)alkyl-(C=O)—NH—, phenyl-(C=O)—NH—, (C$_3$-C$_{20}$)cycloalkyl-(C=O)—NH—, (C$_1$-C$_{20}$)alkoxy-(C=O)—NH—, (C$_3$-C$_{25}$)heteroaryl-(C=O)—NH—, (C$_3$-C$_{25}$)heterocyclic-(C=O)—NH—, (C$_2$-C$_{20}$)alkenyl-(C=O)—NH—, (C$_3$-C$_{20}$)cycloalkenyl-(C=O)—NH—, (C$_2$-C$_{20}$)alkynyl-(C=O)—NH—, (C$_5$-C$_{20}$)cycloalkynyl-(C=O)—NH—, (C$_5$-C$_{25}$)aryl-(C=O)—NH—, perhalo(C$_1$-C$_{20}$)alkyl-(C=O)—NH—, (C$_1$-C$_{20}$)alkyl-(C=O)—{((C$_1$-C$_{20}$)alkyl)N}—, phenyl-(C=O)—{((C$_1$-C$_{20}$)alkyl)N}—, (C$_3$-C$_{20}$)cycloalkyl-(C=O)—{((C$_1$-C$_{20}$)alkyl)N}—, (C$_1$-C$_{20}$)alkoxy-(C=O)—{((C$_1$-C$_{20}$)alkyl)N}—, (C$_3$-C$_{25}$)heteroaryl-(C=O)—{((C$_1$-C$_{20}$)alkyl)N}—, (C$_3$-C$_{25}$)heterocyclic-(C=O)—{((C$_1$-C$_{20}$)alkyl)N}—, (C$_2$-C$_{20}$)alkenyl-(C=O)—{((C$_1$-C$_{20}$)alkyl)N}—, (C$_3$-C$_{20}$)cycloalkenyl-(C=O)—{((C$_1$-C$_{20}$)alkyl)N}—, (C$_2$-C$_{20}$)alkynyl-(C=O)—{((C$_1$-C$_{20}$)alkyl)N}—, (C$_5$-C$_{20}$)cycloalkynyl-(C=O)—{((C$_1$-C$_{20}$)alkyl)N}—, (C$_5$-C$_{25}$)aryl-(C=O)—{((C$_1$-C$_{20}$)alkyl)N}—, perhalo(C$_1$-C$_{20}$)alkyl-(C=O)—{((C$_1$-C$_{20}$)alkyl)N}—, phenyl-(C=O)—NH—, phenyl-(C=O)-{(phenyl)N}—, (C$_1$-C$_{20}$)alkyl-(C=O)-{(phenyl)N}—, (C$_3$-C$_{20}$)cycloalkyl-(C=O)-{(phenyl)N}—, (C$_1$-C$_{20}$)alkoxy-(C=O)-{(phenyl)N}—, (C$_3$-C$_{25}$)heteroaryl-(C=O)-{(phenyl)N}—, (C$_3$-C$_{25}$)heterocyclic-(C=O)-{(phenyl)N}—, (C$_2$-C$_{20}$)alkenyl-(C=O)-{(phenyl)N}—, (C$_3$-C$_{20}$)cycloalkenyl-(C=O)-{(phenyl)N}—, (C$_2$-C$_{20}$)alkynyl-(C=O)-{(phenyl)N}—, (C$_5$-C$_{20}$)cycloalkynyl-(C=O)-{(phenyl)N}—, (C$_5$-C$_{25}$)aryl-(C=O)-{(phenyl)N}—, perhalo(C$_1$-C$_{20}$)alkyl-(C=O)-{(phenyl)N}—, H$_2$N(C=O)—, (C$_1$-C$_{20}$)alkyl-NH—(C=O)—, phenyl-NH—(C=O)—, (C$_3$-C$_{20}$)cycloalkyl-NH—(C=O)—, (C$_1$-C$_{20}$)alkoxy-NH—(C=O)—, (C$_3$-C$_{25}$)heteroaryl-NH—(C=O)—, (C$_3$-C$_{25}$)heterocyclic-NH—(C=O)—, (C$_2$-C$_{20}$)alkenyl-NH—(C=O)—, (C$_3$-C$_{20}$)cycloalkenyl-NH—(C=O)—, (C$_2$-C$_{20}$)alkynyl-NH—(C=O)—, (C$_5$-C$_{20}$)cycloalkynyl-NH—(C=O)—, (C$_5$-C$_{25}$)aryl-NH—(C=O)—, perhalo(C$_1$-C$_{20}$)alkyl-NH—(C=O)—, {C$_1$-C$_{20}$)alkyl}$_2$N —(C=O)—, {phenyl}{(C$_1$-C$_{20}$)alkyl}N—(C=O)—, {(C$_3$-C$_{20}$)cycloalkyl}{(C$_1$-C$_{20}$)alkyl}N—(C=O)—, {(C$_1$-C$_{20}$)alkoxy}{(C$_1$-C$_{20}$)alkyl}N—(C=O)—, {(C$_3$-C$_{25}$)heteroaryl}{(C$_1$-C$_{20}$)alkyl}N—(C=O)—, {(C$_3$-C$_{25}$)heterocyclic}{(C$_1$-C$_{20}$)alkyl}N—(C=O)—, {(C$_2$-C$_{20}$)alkenyl}{(C$_1$-C$_{20}$)alkyl}N—(C=O)—, {(C$_3$-C$_{20}$)cycloalkenyl}{(C$_1$-C$_{20}$)alkyl}N—(C=O)—, {(C$_2$-C$_{20}$)alkynyl}{(C$_1$-C$_{20}$)alkyl}N—(C=O)—, {(C$_5$-C$_{20}$)cycloalkynyl}{(C$_1$-C$_{20}$)alkyl}N—(C=O)—, {(C$_5$-C$_{25}$)aryl}{(C$_1$-C$_{20}$)alkyl}N—(C=O)—, {perhalo(C$_1$-C$_{20}$)alkyl}{(C$_1$-C$_{20}$)alkyl}N—(C=O)—, {phenyl}$_2$N—(C=O)—, {(C$_3$-C$_{20}$)cycloalkyl}{phenyl}N—(C=O)—, {(C$_1$-C$_{20}$)alkoxy}{phenyl}N—(C=O)—, {(C$_3$-C$_{25}$)heteroaryl}{phenyl}N—(C=O)—, {(C$_3$-C$_{25}$)heterocyclic}{phenyl}N—(C=O)—, {(C$_2$-C$_{20}$)alkenyl}{phenyl}N—(C=O)—, {(C$_3$-C$_{20}$)cycloalkenyl}{phenyl}N—(C=O)—, {(C$_2$-C$_{20}$)alkynyl}{phenyl}N—(C=O)—, {(C$_5$-C$_{20}$)cycloalkynyl}{phenyl}N—(C=O)—, {(C$_5$-C$_{25}$)aryl}{phenyl}N—(C=O)—, {perhalo(C$_1$-C$_{20}$)alkyl}{phenyl}N—(C=O)—, HO—(C=O)—, (C$_1$-C$_{20}$)alkyl-(C=O)—, (C$_3$-C$_{25}$)heteroaryl-(C=O)—, (C$_3$-C$_{25}$)heterocyclic-(C=O)—, (C$_2$-C$_{20}$)alkenyl-(C=O)—, (C$_3$-C$_{20}$) cycloalkenyl-(C=O)—, (C$_2$-C$_{20}$)alkynyl-(C=O)—, (C$_5$-C$_{25}$)aryl-(C=O)—, perhalo(C$_1$-C$_{20}$)alkyl-(C=O)—, phenyl-(C=O)—, (C$_1$-C$_{20}$)alkyl-O—(C=O)—, (C$_3$-C$_{25}$)heteroaryl-O—(C=O)—, (C$_3$-C$_{25}$)heterocyclic-O—(C=O)—, (C$_2$-C$_{20}$)alkenyl-O—(C=O)—, (C$_3$-C$_{20}$)cycloalkenyl-O—(C=O)—, (C$_2$-C$_{20}$)alkynyl-O—(C=O)—, (C$_5$-C$_{25}$)aryl-O—(C=O)—, perhalo(C$_1$-C$_{20}$)alkyl-O—(C=O)—, phenyl-O—(C=O)—, (C$_1$-C$_{20}$)alkyl-(C=O)—O—, (C$_3$-C$_{25}$)heteroaryl-(C=O)—O—, (C$_3$-C$_{25}$)heterocyclic-(C=O)—O—, (C$_2$-C$_{20}$)alkenyl-(C=O)—O—, (C$_3$-C$_{20}$)cycloalkenyl-(C=O)—O—, (C$_2$-C$_{20}$)alkynyl-(C=O)—O—, (C$_5$-C$_{25}$)aryl-(C=O)—O—, phenyl-(C=O)—O—, perhalo(C$_1$-C$_{20}$)alkyl-(C=O)—O—, and salts thereof;

and wherein two independently chosen R$^2$, R$^3$, R$^4$, R$^5$, R$^6$, R$^7$, R$^8$, R$^9$, R$^{10}$, and R$^{11}$ alkyl-containing groups may be taken together with any atom to which they are attached to form a three to forty membered cyclic, heterocyclic or heteroaryl ring.

One embodiment provides a composition, which includes the above compound or salt thereof, and at least one pharmaceutically acceptable carrier, excipient, adjuvant or diluent One embodiment provides a method, which includes administering the above compound or salt thereof to a human.

BRIEF DESCRIPTION OF THE FIGURES

FIG. 1 is a chart showing the inhibition of TNFα release.
FIG. 2 is a chart showing the inhibition of NO release.
FIG. 3 shows the combined results for inhibition of nitric oxide and TNFα release.

DETAILED DESCRIPTION OF THE INVENTION

Figure 4:
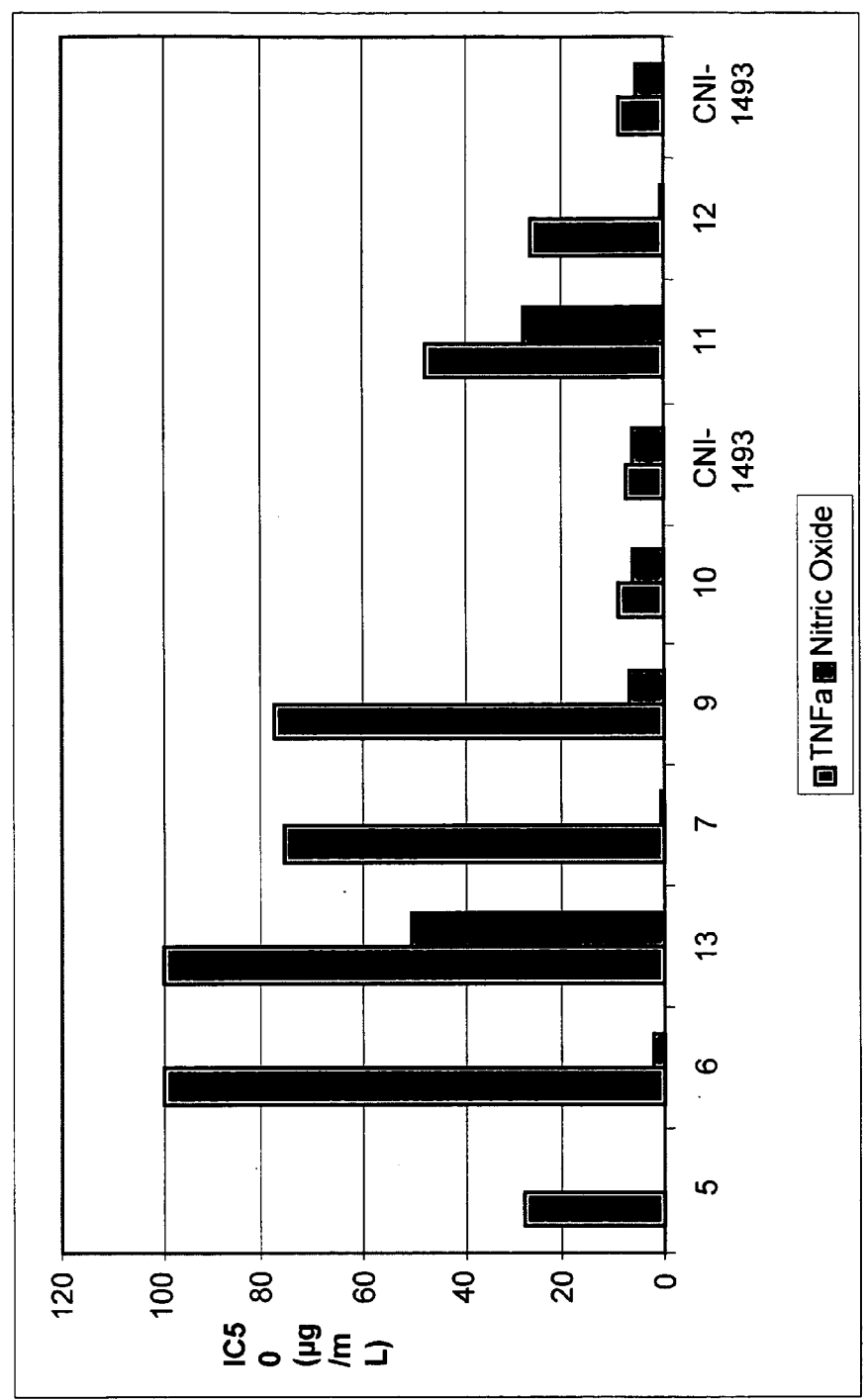
FIG. 4 shows the combined results for inhibition of nitric oxide and TNFα release.

The present invention relates to compounds having the formula:

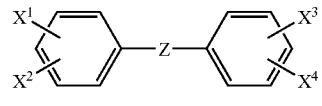

salts thereof; compositions comprising one or more of the compounds and/or salts thereof; methods of using; and methods of making;

wherein X$^1$, X$^2$, X$^3$, and X$^4$ each independently represent H, GhyCH—, GhyCCH$_3$—, or CH$_3$CO—, with the provisos that X$^1$, X$^2$, X$^3$ and X$^4$ are not simultaneously H;

wherein Z is one or more selected from the group consisting of:

—(A$^1$)$_a$—(CR$^2$R$^3$)$_x$—(A$^2$)$_b$—;

—(A$^1$)$_a$—(CR$^2$R$^3$)$_x$—Q$_m$—(CR$^4$R$^5$)$_y$—(A$^2$)$_b$—; and

—(A$^1$)$_a$—(CR$^2$R$^3$)$_x$—Q$_m$—(CR$^4$R$^5$)$_y$—T$_n$—(CR$^6$R$^7$)$_z$—(A$^2$)$_b$—;

and combinations thereof;

wherein a is selected from the group consisting of 0, 1, 2, 3, 4, 5, 6, 7, 8, and 9;

wherein b is selected from the group consisting of 0, 1, 2, 3, 4, 5, 6, 7, 8, and 9;

wherein x is selected from the group consisting of 0, 1, 2, 3, 4, 5, 6, 7, 8, and 9;

wherein y is selected from the group consisting of 0, 1, 2, 3, 4, 5, 6, 7, 8, and 9;

wherein z is selected from the group consisting of 0, 1, 2, 3, 4, 5, 6, 7, 8, and 9;

wherein m is selected from the group consisting of 0, 1, 2, 3, 4, 5, 6, 7, 8, and 9;

wherein n is selected from the group consisting of 0, 1, 2, 3, 4, 5, 6, 7, 8, and 9;

wherein A$^1$ and A$^2$ are each independently selected from the group consisting of —NR$^8$(CO)NR$^9$—, —(CO)NR$^8$—, —NR$^8$(CO)—, —NR$^8$—, —O—, —S—, —S(=O)—, —SO$_2$—, —SO$_2$NR$^8$—, —NR$^8$SO$_2$—, and salts thereof;

wherein Q and T are each independently selected from the group consisting of —NR$^{10}$(CO)NR$^{11}$—, —(CO)NR$^{10}$—, —NR$^{10}$(CO)—, —NR$^{10}$—, —O—, —S—, —S(=O)—, —SO$_2$—, —SO$_2$NR$^{10}$—, —NR$^{10}$SO$_2$—, salts thereof, branched or unbranched, saturated or unsaturated, substituted or unsubstituted C$_1$-C$_{20}$ alkylene, saturated or unsaturated, substituted or unsubstituted C$_3$-C$_{20}$ cycloalkylene, substituted or unsubstituted C$_5$-C$_{25}$ arylene, and combinations thereof;

wherein one or more carbon atoms in any of said alkylene, cycloalkylene or arylene in said Q and/or T may each be independently replaced with one or more heteroatoms selected from the group consisting of nitrogen, oxygen, sulfur, and a combination thereof;

and wherein when substituted, said alkylene, cycloalkylene or arylene in said Q and/or T are each independently substituted with one or more substituent groups selected from the group consisting of hydroxy, halo, bromo, chloro, iodo, fluoro, —N$_3$, —CN, —NC, —SH, —NO$_2$, —NH$_2$, (C$_1$-C$_{20}$)alkyl, phenyl, (C$_3$-C$_{20}$)cycloalkyl, (C$_1$-C$_{20}$)alkoxy, (C$_3$-C$_{25}$)heteroaryl, (C$_3$-C$_{25}$)heterocyclic, (C$_2$-C$_{20}$)alkenyl, (C$_3$-C$_{20}$)cycloalkenyl, (C$_2$-C$_{20}$)alkynyl, (C$_5$-C$_{20}$)cycloalkynyl, (C$_5$-C$_{25}$)aryl, perhalo(C$_1$-C$_{20}$)alkyl, (C$_1$-C$_{20}$)alkyl-O—, phenyl-O—, (C$_3$-C$_{20}$)cycloalkyl-O—, (C$_3$-C$_{25}$)heteroaryl-O—, (C$_3$-C$_{25}$)heterocyclic-O—, (C$_2$-C$_{20}$)alkenyl-O—, (C$_3$-C$_{20}$)cycloalkenyl-O—, (C$_2$-C$_{20}$)alkynyl-O—, (C$_5$-C$_{20}$)cycloalkynyl-O—, (C$_5$-C$_{25}$)aryl-O—, perhalo(C$_1$-C$_{20}$)alkyl-O—, (C$_1$-C$_{20}$)alkyl-S—, phenyl-S—, (C$_3$-C$_{20}$)cycloalkyl-S—, (C$_3$-C$_{25}$)heteroaryl-S—, (C$_3$-C$_{25}$)heterocyclic-S—, (C$_2$-C$_{20}$)alkenyl-S—, (C$_3$-C$_{20}$)cycloalkenyl-S—, (C$_2$-C$_{20}$)alkynyl-S—, (C$_5$-C$_{20}$)cycloalkynyl-S—, (C$_5$-C$_{25}$)aryl-S—, perhalo(C$_1$-C$_{20}$)alkyl-S—, (C$_1$-C$_{20}$)alkyl-SO$_2$—, phenyl-SO$_2$—, (C$_3$-C$_{20}$)cycloalkyl-SO$_2$—, (C$_1$-C$_{20}$)alkoxy-SO$_2$—, (C$_3$-C$_{25}$)heteroaryl-SO$_2$—, (C$_3$-C$_{25}$)heterocyclic-SO$_2$—, (C$_2$-C$_{20}$)alkenyl-SO$_2$—, (C$_3$-C$_{20}$)cycloalkenyl-SO$_2$—, (C$_2$-C$_{20}$)alkynyl-SO$_2$—, (C$_5$-C$_{20}$)cycloalkynyl-SO$_2$—, (C$_5$-C$_{25}$)aryl-SO$_2$—, perhalo(C$_1$-C$_{20}$)alkyl-SO$_2$—, H$_2$N—SO$_2$—, (C$_1$-C$_{20}$)alkyl-NH—SO$_2$—, phenyl-NH—SO$_2$—, (C$_3$-C$_{20}$)cycloalkyl-NH—SO$_2$—, (C$_1$-C$_{20}$)alkoxy-NH—SO$_2$—, (C$_3$-C$_{25}$)heteroaryl-NH—SO$_2$—, (C$_3$-C$_{25}$)heterocyclic-NH—SO$_2$—, (C$_2$-C$_{20}$)alkenyl-NH—SO$_2$—, (C$_3$-C$_{20}$)cycloalkenyl-NH—SO$_2$—, (C$_2$-C$_{20}$)alkynyl-NH—SO$_2$—, (C$_5$-C$_{20}$)cycloalkynyl-NH—SO$_2$—, (C$_5$-C$_{25}$)aryl-NH—SO$_2$—, perhalo(C$_1$-C$_{20}$)alkyl-NH—SO$_2$—, {(C$_1$-C$_{20}$)alkyl}$_2$N—SO$_2$—, {phenyl}$_2$N—SO$_2$—, {(C$_3$-C$_{20}$)cycloalkyl}$_2$N—SO$_2$—, {(C$_1$-C$_{20}$)alkoxy}$_2$N—SO$_2$—, {(C$_3$-C$_{25}$)heteroaryl}$_2$N—SO$_2$—, {(C$_3$-C$_{25}$)heterocyclic}$_2$N—SO$_2$—, {(C$_2$-C$_{20}$)alkenyl}$_2$N—SO$_2$—, {(C$_2$-C$_{20}$)alkynyl}$_2$N—SO$_2$—, {(C$_5$-C$_{20}$)cycloalkynyl}$_2$N—SO$_2$—, {(C$_5$-C$_{25}$)aryl}$_2$N—SO$_2$—, {perhalo(C$_1$-C$_{20}$)alkyl}$_2$N—SO$_2$—, (C$_1$-C$_{20}$)alkyl-SO$_2$—NH—, phenyl-SO$_2$—NH—, (C$_3$-C$_{20}$)cycloalkyl-SO$_2$—NH—, (C$_1$-C$_{20}$)alkoxy-SO$_2$—NH—, (C$_3$-C$_{25}$)heteroaryl-SO$_2$—NH—, (C$_3$-C$_{25}$)heterocyclic-SO$_2$—NH—, (C$_2$-C$_{20}$)alkenyl-SO$_2$—NH—, (C$_3$-C$_{20}$)cycloalkenyl-SO$_2$—NH—, (C$_2$-C$_{20}$)alkynyl-SO$_2$—NH—, (C$_5$-C$_{20}$)cycloalkynyl-SO$_2$—NH—, (C$_5$-C$_{25}$)aryl-SO$_2$—NH—, perhalo(C$_1$-C$_{20}$)alkyl-SO$_2$—NH—, (C$_1$-C$_{20}$)alkyl-NH—, phenyl-NH—, (C$_3$-C$_{20}$)cycloalkyl-NH—, (C$_1$-C$_{20}$)alkoxy-NH—, (C$_3$-C$_{25}$)heteroaryl-NH—, (C$_3$-C$_{25}$)heterocyclic-NH—, (C$_2$-C$_{20}$)alkenyl-NH—, (C$_3$-C$_{20}$)cycloalkenyl-NH—, (C$_2$-C$_{20}$)alkynyl-NH—, (C$_5$-C$_{20}$)cycloalkynyl-NH—, (C$_5$-C$_{25}$)aryl-NH—, perhalo(C$_1$-C$_{20}$)alkyl-NH—, {(C$_1$-C$_{20}$)alkyl}$_2$N—, {phenyl}$_2$N—, {(C$_3$-C$_{20}$)cycloalkyl}$_2$N—, {(C$_1$-C$_{20}$)alkoxy}$_2$N—, {(C$_3$-C$_{25}$)heteroaryl}$_2$N—, {(C$_3$-C$_{25}$)heterocyclic}$_2$N—, {(C$_2$-C$_{20}$)alkenyl}$_2$N—, {(C$_3$-C$_{20}$)cycloalkenyl}$_2$N—, {(C$_2$-C$_{20}$)alkynyl}$_2$N—, {(C$_5$-C$_{20}$)cycloalkynyl}$_2$N—, {(C$_5$-C$_{25}$)aryl}$_2$N—, {perhalo(C$_1$-C$_{20}$)alkyl}$_2$N—, (C$_1$-C$_{20}$)alkyl-(C=O)—NH—, phenyl-(C=O)—NH—, (C$_3$-C$_{20}$)cycloalkyl-(C=O)—NH—, (C$_1$-C$_{20}$)alkoxy-(C=O)—NH—, (C$_3$-C$_{25}$)heteroaryl-(C=O)—NH—, (C$_3$-C$_{25}$)heterocyclic-(C=O)—NH—, (C$_2$-C$_{20}$)alkenyl-(C=O)—NH—, (C$_3$-C$_{20}$)cycloalkenyl-(C=O)—NH—, (C$_2$-C$_{20}$)alkynyl-(C=O)—NH—, (C$_5$-C$_{20}$)cycloalkynyl-(C=O)—NH—, (C$_5$-C$_{25}$)aryl-(C=O)—NH—, perhalo(C$_1$-C$_{20}$)alkyl-(C=O)—NH—, (C$_1$-C$_{20}$)alkyl-(C=O)—{((C$_1$-C$_{20}$)alkyl)N}—, phenyl-(C=O)—{((C$_1$-C$_{20}$)alkyl)N}—, (C$_3$-C$_{20}$)cycloalkyl-(C=O)—{((C$_1$-C$_{20}$)alkyl)N}—, (C$_1$-C$_{20}$)alkoxy-(C=O)—{((C$_1$-C$_{20}$)alkyl)N}—, (C$_3$-C$_{25}$)heteroaryl-(C=O)—{((C$_1$-C$_{20}$)alkyl)N}—, (C$_3$-C$_{25}$)heterocyclic-(C=O)—{((C$_1$-C$_{20}$)alkyl)N}—, (C$_2$-C$_{20}$)alkenyl-(C=O)—{((C$_1$-C$_{20}$)alkyl)N}—, (C$_3$-C$_{20}$)cycloalkenyl-(C=O)—{((C$_1$-C$_{20}$)alkyl)N}—, (C$_2$-C$_{20}$)alkynyl-(C=O)—{((C$_1$-C$_{20}$)alkyl)N}—, (C$_5$-C$_{25}$)aryl-(C=O)—{((C$_1$-C$_{20}$)alkyl)N}—, perhalo(C$_1$-C$_{20}$)alkyl-(C=O)—{((C$_1$-C$_{20}$)alkyl)N}—, phenyl-(C=O)—NH—, phenyl-(C=O)-{(phenyl)N}—, (C$_1$-C$_{20}$)alkyl-(C=O)-{(phenyl)N}—, (C$_3$-C$_{20}$)cycloalkyl-(C=O)-{(phenyl)N}—, (C$_1$-C$_{20}$)alkoxy-(C=O)-{(phenyl)N}—, (C$_3$-C$_{25}$)heteroaryl-(C=O)-{(phenyl)N}—, (C$_3$-C$_{25}$)heterocyclic-(C=O)-{(phenyl)N}—, (C$_2$-C$_{20}$)alkenyl-(C=O)-{(phenyl)N}—, (C$_3$-C$_{20}$)cycloalkenyl-(C=O)-{(phenyl)N}—, (C$_2$-C$_{20}$)alkynyl-(C=O)-{(phenyl)N}—, (C$_5$-C$_{20}$)cycloalkynyl-(C=O)-{(phenyl)N}—, (C$_5$-C$_{25}$)aryl-(C=O)-{(phenyl)N}—, perhalo(C$_1$-C$_{20}$)alkyl-(C=O)-{(phenyl)N}—, H$_2$N(C=O)—, (C$_1$-C$_{20}$)alkyl-NH—(C=O)—, phenyl-NH—(C=O)—, (C$_3$-C$_{20}$)cycloalkyl-NH—(C=O)—, (C$_1$-C$_{20}$)alkoxy-NH—(C=O)—, (C$_3$-C$_{25}$)heteroaryl-NH—(C=O)—, (C$_3$-C$_{25}$)heterocyclic-NH—(C=O)—, (C$_2$-C$_{20}$)alkenyl-NH—(C=O)—, (C$_3$-C$_{20}$)cycloalkenyl-NH—(C=O)—, (C$_2$-C$_{20}$)alkynyl-NH—(C=O)—, (C$_5$-C$_{20}$)cycloalkynyl-NH—(C=O)—, (C$_5$-C$_{25}$)aryl-NH—(C=O)—, perhalo(C$_1$-C$_{20}$)alkyl-NH—(C=O)—, {(C$_1$-C$_{20}$)alkyl}$_2$N—(C=O)—, {phenyl}{(C$_1$-C$_{20}$)alkyl}N—(C=O)—, {(C$_3$-C$_{20}$)cycloalkyl}{($C_1$-$C_{20}$)alkyl}N—(C=O)—, {($C_1$-$C_{20}$)alkoxy}{($C_1$-$C_{20}$)alkyl}N—(C=O)—, {($C_3$-$C_{25}$)heteroaryl}{($C_1$-$C_{20}$)alkyl}N—(C=O)—, {($C_3$-$C_{25}$)heterocyclic}{($C_1$-$C_{20}$)alkyl}N—(C=O)—, {($C_2$-$C_{20}$)alkenyl}{($C_1$-$C_{20}$)alkyl}N—(C=O)—, {($C_3$-$C_{20}$)cycloalkenyl}{($C_1$-$C_{20}$)alkyl}N—(C=O)—, {($C_2$-$C_{20}$)alkynyl}{($C_1$-$C_{20}$)alkyl}N—(C=O)—, {($C_5$-$C_{20}$)cycloalkynyl}{($C_1$-$C_{20}$)alkyl}N—(C=O)—, {($C_5$-$C_{25}$)aryl}{($C_1$-$C_{20}$)alkyl}N—(C=O)—, {perhalo($C_1$-$C_{20}$)alkyl}{($C_1$-$C_{20}$)alkyl}N—(C=O)—, {phenyl}$_2$N—(C=O)—, {($C_3$-$C_{20}$)cycloalkyl}{phenyl}N—(C=O)—, {($C_1$-$C_{20}$)alkoxy}{phenyl}N—(C=O)—, {($C_3$-$C_{25}$)heteroaryl}{phenyl}N—(C=O)—, {($C_3$-$C_{25}$)heterocyclic}{phenyl}N—(C=O)—, {($C_2$-$C_{20}$)alkenyl}{phenyl}N—(C=O)—, {($C_3$-$C_{20}$)cycloalkenyl}{phenyl}N—(C=O)—, {($C_2$-$C_{20}$)alkynyl}{phenyl}N—(C=O)—, {($C_5$-$C_{20}$)cycloalkynyl}{phenyl}N—(C=O)—, {($C_5$-$C_{25}$)aryl}{phenyl}N—(C=O)—, {perhalo($C_1$-$C_{20}$)alkyl}{phenyl}N—(C=O)—, HO—(C=O)—, ($C_1$-$C_{20}$)alkyl-(C=O)—, ($C_3$-$C_{25}$)heteroaryl-(C=O)—, ($C_3$-$C_{25}$)heterocyclic-(C=O)—, ($C_2$-$C_{20}$)alkenyl-(C=O)—, ($C_3$-$C_{20}$) cycloalkenyl-(C=O)—, ($C_2$-$C_{20}$)alkynyl-(C=O)—, ($C_5$-$C_{25}$)aryl-(C=O)—, perhalo($C_1$-$C_{20}$)alkyl-(C=O)—, phenyl-(C=O)—, ($C_1$-$C_{20}$)alkyl-O—(C=O)—, ($C_3$-$C_{25}$)heteroaryl-O—(C=O)—, ($C_3$-$C_{25}$)heterocyclic-O—(C=O)—, ($C_2$-$C_{20}$)alkenyl-O—(C=O)—, ($C_3$-$C_{20}$)cycloalkenyl-O—(C=O)—, ($C_2$-$C_{20}$)alkynyl-O—(C=O)—, ($C_5$-$C_{25}$)aryl-O—(C=O)—, perhalo($C_1$-$C_{20}$)alkyl-O—(C=O)—, phenyl-O—(C=O)—, ($C_1$-$C_{20}$)alkyl-(C=O)—O—, ($C_3$-$C_{25}$)heteroaryl-(C=O)—O—, ($C_3$-$C_{25}$)heterocyclic-(C=O)—O—, ($C_2$-$C_{20}$)alkenyl-(C=O)—O—, ($C_3$-$C_{20}$)cycloalkenyl-(C=O)—O—, ($C_2$-$C_{20}$)alkynyl-(C=O)—O—, ($C_5$-$C_{25}$)aryl-(C=O)—O—, phenyl-(C=O)—O—, perhalo($C_1$-$C_{20}$)alkyl-(C=O)—O—, and salts thereof;

wherein each of the aforesaid ($C_1$-$C_{20}$)alkyl, phenyl, ($C_3$-$C_{20}$)cycloalkyl, ($C_1$-$C_{20}$)alkoxy, ($C_3$-$C_{25}$)heteroaryl, ($C_3$-$C_{25}$)heterocyclic, ($C_2$-$C_{20}$)alkenyl, ($C_3$-$C_{20}$) cycloalkenyl, ($C_2$-$C_{20}$)alkynyl, ($C_5$-$C_{20}$)cycloalkynyl, and ($C_5$-$C_{25}$) aryl groups (as substituents on said alkylene, cycloalkylene or arylene of said Q and T) may be optionally and independently substituted by one to four moieties selected from the group consisting of hydroxy, halo, bromo, chloro, iodo, fluoro, —$N_3$, —CN, —NC, —SH, —$NO_2$, —$NH_2$, ($C_1$-$C_{20}$)alkyl, phenyl, ($C_3$-$C_{20}$)cycloalkyl, ($C_1$-$C_{20}$)alkoxy, ($C_3$-$C_{25}$)heteroaryl, ($C_3$-$C_{25}$)heterocyclic, ($C_2$-$C_{20}$)alkenyl, ($C_3$-$C_{20}$)cycloalkenyl, ($C_2$-$C_{20}$)alkynyl, ($C_5$-$C_{20}$)cycloalkynyl, ($C_5$-$C_{25}$)aryl, perhalo($C_1$-$C_{20}$)alkyl, ($C_1$-$C_{20}$)alkyl-O—, phenyl-O—, ($C_3$-$C_{20}$)cycloalkyl-O—, ($C_3$-$C_{25}$)heteroaryl-O—, ($C_3$-$C_{25}$)heterocyclic-O—, ($C_2$-$C_{20}$)alkenyl-O—, ($C_3$-$C_{20}$)cycloalkenyl-O—, ($C_2$-$C_{20}$)alkynyl-O—, ($C_5$-$C_{20}$)cycloalkynyl-O—, ($C_5$-$C_{25}$)aryl-O—, perhalo($C_1$-$C_{20}$)alkyl-O—, ($C_1$-$C_{20}$)alkyl-S—, phenyl-S—, ($C_3$-$C_{20}$)cycloalkyl-S—, ($C_3$-$C_{25}$)heteroaryl-S—, ($C_3$-$C_{25}$)heterocyclic-S—, ($C_2$-$C_{20}$)alkenyl-S—, ($C_3$-$C_{20}$)cycloalkenyl-S—, ($C_2$-$C_{20}$)alkynyl-S—, ($C_5$-$C_{20}$)cycloalkynyl-S—, ($C_5$-$C_{25}$)aryl-S—, perhalo($C_1$-$C_{20}$)alkyl-S—, ($C_1$-$C_{20}$)alkyl-$SO_2$—, phenyl-$SO_2$—, ($C_3$-$C_{20}$)cycloalkyl-$SO_2$—, ($C_1$-$C_{20}$)alkoxy-$SO_2$—, ($C_3$-$C_{25}$)heteroaryl-$SO_2$—, ($C_3$-$C_{25}$)heterocyclic-$SO_2$—, ($C_2$-$C_{20}$)alkenyl-$SO_2$—, ($C_3$-$C_{20}$)cycloalkenyl-$SO_2$—, ($C_2$-$C_{20}$)alkynyl-$SO_2$—, ($C_5$-$C_{20}$)cycloalkynyl-$SO_2$—, ($C_5$-$C_{25}$)aryl-$SO_2$—, perhalo($C_1$-$C_{20}$)alkyl-$SO_2$—, $H_2$N—$SO_2$—, ($C_1$-$C_{20}$)alkyl-NH—$SO_2$—, phenyl-NH—$SO_2$—, ($C_3$-$C_{20}$)cycloalkyl-NH—$SO_2$—, ($C_1$-$C_{20}$)alkoxy-NH—$SO_2$—, ($C_3$-$C_{25}$)heteroaryl-NH—$SO_2$—, ($C_3$-$C_{25}$)heterocyclic-NH—$SO_2$—, ($C_2$-$C_{20}$)alkenyl-NH—$SO_2$—, ($C_3$-$C_{20}$)cycloalkenyl-NH—$SO_2$—, ($C_2$-$C_{20}$)alkynyl-NH—$SO_2$—, ($C_5$-$C_{20}$)cycloalkynyl-NH—$SO_2$—, ($C_5$-$C_{25}$)aryl-NH—$SO_2$—, perhalo($C_1$-$C_{20}$)alkyl-NH—$SO_2$—, {($C_1$-$C_{20}$)alkyl}$_2$N—$SO_2$—, {phenyl}$_2$N—$SO_2$—, {($C_3$-$C_{20}$)cycloalkyl}$_2$N—$SO_2$—, {($C_1$-$C_{20}$)alkoxy}$_2$N—$SO_2$—, {($C_3$-$C_{25}$)heteroaryl}$_2$N—$SO_2$—, {($C_3$-$C_{25}$)heterocyclic}$_2$N—$SO_2$—, {($C_2$-$C_{20}$)alkenyl}$_2$N—$SO_2$—, {($C_2$-$C_{20}$)alkynyl}$_2$N—$SO_2$—, {($C_5$-$C_{20}$)cycloalkynyl}$_2$N—$SO_2$—, {($C_5$-$C_{25}$)aryl}$_2$N—$SO_2$—, {perhalo($C_1$-$C_{20}$)alkyl}$_2$N—$SO_2$—, ($C_1$-$C_{20}$)alkyl-$SO_2$—NH—, phenyl-$SO_2$—NH—, ($C_3$-$C_{20}$)cycloalkyl-$SO_2$—NH—, ($C_1$-$C_{20}$)alkoxy-$SO_2$—NH—, ($C_3$-$C_{25}$)heteroaryl-$SO_2$—NH—, ($C_3$-$C_{25}$)heterocyclic-$SO_2$—NH—, ($C_2$-$C_{20}$)alkenyl-$SO_2$—NH—, ($C_3$-$C_{20}$)cycloalkenyl-$SO_2$—NH—, ($C_2$-$C_{20}$)alkynyl-$SO_2$—NH—, ($C_5$-$C_{20}$)cycloalkynyl-$SO_2$—NH—, ($C_5$-$C_{25}$)aryl-$SO_2$—NH—, perhalo($C_1$-$C_{20}$)alkyl-$SO_2$—NH—, ($C_1$-$C_{20}$)alkyl-NH—, phenyl-NH—, ($C_3$-$C_{20}$)cycloalkyl-NH—, ($C_1$-$C_{20}$)alkoxy-NH—, ($C_3$-$C_{25}$)heteroaryl-NH—, ($C_3$-$C_{25}$)heterocyclic-NH—, ($C_2$-$C_{20}$)alkenyl-NH—, ($C_3$-$C_{20}$)cycloalkenyl-NH—, ($C_2$-$C_{20}$)alkynyl-NH—, ($C_5$-$C_{20}$)cycloalkynyl-NH—, ($C_5$-$C_{25}$)aryl-NH—, perhalo($C_1$-$C_{20}$)alkyl-NH—, {($C_1$-$C_{20}$)alkyl}$_2$N—, {phenyl}$_2$N—, {($C_3$-$C_{20}$)cycloalkyl}$_2$N—, {($C_1$-$C_{20}$)alkoxy}$_2$N—, {($C_3$-$C_{25}$)heteroaryl}$_2$N—, {($C_3$-$C_{25}$)heterocyclic}$_2$N—, {($C_2$-$C_{20}$)alkenyl}$_2$N—, {($C_3$-$C_{20}$)cycloalkenyl}$_2$N—, {($C_2$-$C_{20}$)alkynyl}$_2$N—, {($C_5$-$C_{20}$)cycloalkynyl}$_2$N—, {($C_5$-$C_{25}$)aryl}$_2$N—, {perhalo($C_1$-$C_{20}$)alkyl}$_2$N—, ($C_1$-$C_{20}$)alkyl-(C=O)—NH—, phenyl-(C=O)—NH—, ($C_3$-$C_{20}$)cycloalkyl-(C=O)—NH—, ($C_1$-$C_{20}$)alkoxy-(C=O)—NH—, ($C_3$-$C_{25}$)heteroaryl-(C=O)—NH—, ($C_3$-$C_{25}$)heterocyclic-(C=O)—NH—, ($C_2$-$C_{20}$)alkenyl-(C=O)—NH—, ($C_3$-$C_{20}$)cycloalkenyl-(C=O)—NH—, ($C_2$-$C_{20}$)alkynyl-(C=O)—NH—, ($C_5$-$C_{20}$)cycloalkynyl-(C=O)—NH—, ($C_5$-$C_{25}$)aryl-(C=O)—NH—, perhalo($C_1$-$C_{20}$)alkyl-(C=O)—NH—, ($C_1$-$C_{20}$)alkyl-(C=O)—{(($C_1$-$C_{20}$)alkyl)N}—, phenyl-(C=O)—{(($C_1$-$C_{20}$)alkyl)N}—, ($C_3$-$C_{20}$)cycloalkyl-(C=O)—{(($C_1$-$C_{20}$)alkyl)N}—, ($C_1$-$C_{20}$)alkoxy-(C=O)—{(($C_1$-$C_{20}$)alkyl)N}—, ($C_3$-$C_{25}$)heteroaryl-(C=O)—{(($C_1$-$C_{20}$)alkyl)N}—, ($C_3$-$C_{25}$)heterocyclic-(C=O)—{(($C_1$-$C_{20}$)alkyl)N}—, ($C_2$-$C_{20}$)alkenyl-(C=O)—{(($C_1$-$C_{20}$)alkyl)N}—, ($C_3$-$C_{20}$) cycloalkenyl-(C=O)—{(($C_1$-$C_{20}$)alkyl)N}—, ($C_2$-$C_{20}$)alkynyl-(C=O)—{(($C_1$-$C_{20}$)alkyl)N}—, ($C_5$-$C_{20}$)cycloalkynyl-(C=O)—{(($C_1$-$C_{20}$)alkyl)N}—, ($C_5$-$C_{25}$)aryl-(C=O)—{(($C_1$-$C_{20}$)alkyl)N}—, perhalo($C_1$-$C_{20}$)alkyl-(C=O)—{(($C_1$-$C_{20}$)alkyl)N}—, phenyl-(C=O)—NH—, phenyl-(C=O)-{(phenyl)N}—, ($C_1$-$C_{20}$)alkyl-(C=O)-{(phenyl)N}—, ($C_3$-$C_{20}$)cycloalkyl-(C=O)-{(phenyl)N}—, ($C_1$-$C_{20}$)alkoxy-(C=O)-{(phenyl)N}—, ($C_3$-$C_{25}$)heteroaryl-(C=O)-{(phenyl)N}—, ($C_3$-$C_{25}$)heterocyclic-(C=O)-{(phenyl)N}—, ($C_2$-$C_{20}$)alkenyl-(C=O)-{(phenyl)N}—, ($C_3$-$C_{20}$)cycloalkenyl-(C=O)-{(phenyl)N}—, ($C_2$-$C_{20}$)alkynyl-(C=O)-{(phenyl)N}—, ($C_5$-$C_{20}$)cycloalkynyl-(C=O)-{(phenyl)N}—, ($C_5$-$C_{25}$)aryl-(C=O)-{(phenyl)N}—, perhalo($C_1$-$C_{20}$)alkyl-(C=O)-{(phenyl)N}—, $H_2$N(C=O)—, ($C_1$-$C_{20}$)alkyl-NH—(C=O)—, phenyl-NH—(C=OH, ($C_3$-$C_{20}$)cycloalkyl-NH—(C=O)—, ($C_1$-$C_{20}$)alkoxy-NH—(C=O)—, ($C_3$-$C_{25}$)heteroaryl-NH—(C=O)—, ($C_3$-$C_{25}$)heterocyclic-NH—(C=O)—, ($C_2$-$C_{20}$)alkenyl-NH—(C=O)—, ($C_3$-$C_{20}$)cycloalkenyl-NH—(C=O)—, ($C_2$-$C_{20}$)alkynyl-NH—(C=O)—, ($C_5$-$C_{20}$)cycloalkynyl-NH—(C=O)—, ($C_5$-$C_{20}$)aryl-NH—(C=OH, perhalo($C_1$-$C_{20}$)alkyl-NH—(C=O)—, {($C_1$-$C_{20}$)alkyl}$_2$N—(C=O)—, {phenyl}{($C_1$-$C_{20}$)alkyl}N—(C=O)—, {($C_3$-$C_{20}$)cycloalkyl}{($C_1$-$C_{20}$)alkyl}N—(C=O)—, {($C_1$-$C_{20}$)alkoxy}{($C_1$-$C_{20}$)alkyl}N—(C=O)—, {($C_3$-$C_{25}$)heteroaryl}{($C_1$-$C_{20}$)alkyl-}N—(C=O)—, {($C_3$-$C_{25}$)heterocyclic}{($C_1$-$C_{20}$)alkyl}N—(C=O)—, {($C_2$-$C_{20}$)alkenyl}{($C_1$-$C_{20}$)alkyl}N—(C=O)—, {($C_3$-$C_{20}$)cycloalkenyl}{($C_1$-$C_{20}$)alkyl}N—(C=O)—, {($C_2$-$C_{20}$)alkynyl}{($C_1$-$C_{20}$)alkyl}N—(C=O)—, {($C_5$-$C_{20}$)cycloalkynyl}{($C_1$-$C_{20}$)alkyl}N—(C=O)—, {($C_5$-$C_{25}$)aryl}{($C_1$-$C_{20}$)alkyl}N—(C=O)—, {perhalo($C_1$-$C_{20}$)alkyl}{($C_1$-$C_{20}$)alkyl}N—(C=O)—, {phenyl}$_2$N—(C=O)—, {($C_3$-$C_{20}$)cycloalkyl}{phenyl}N—(C=O)—, {($C_1$-$C_{20}$)alkoxy}{phenyl}N—(C=O)—, {($C_3$-$C_{25}$)heteroaryl}{phenyl}N—(C=O)—, {($C_3$-$C_{25}$)heterocyclic}{phenyl}N—(C=O)—, {($C_2$-$C_{20}$)alkenyl}{phenyl}N—(C=O)—, {($C_3$-$C_{20}$)cycloalkenyl}{phenyl}N—(C=O)—, {($C_2$-$C_{20}$)alkynyl}{phenyl}N—(C=O)—, {($C_5$-$C_{20}$)cycloalkynyl}{phenyl}N—(C=O)—, {($C_5$-$C_{25}$)aryl}{phenyl}N—(C=O)—, {perhalo($C_1$-$C_{20}$)alkyl}{phenyl}N—(C=O)—, HO—(C=O)—, ($C_1$-$C_{20}$)alkyl-(C=O)—, ($C_3$-$C_{25}$)heteroaryl-(C=O)—, ($C_3$-$C_{25}$)heterocyclic-(C=O)—, ($C_2$-$C_{20}$)alkenyl-(C=O)—, ($C_3$-$C_{20}$)cycloalkenyl-(C=O)—, ($C_2$-$C_{20}$)alkynyl-(C=O)—, ($C_5$-$C_{25}$)aryl-(C=O)—, perhalo($C_1$-$C_{20}$)alkyl-(C=O)—, phenyl-(C=O)—, ($C_1$-$C_{20}$)alkyl-O—(C=O)—, ($C_3$-$C_{25}$)heteroaryl-O—(C=O)—, ($C_3$-$C_{25}$)heterocyclic-O—(C=O)—, ($C_2$-$C_{20}$)alkenyl-O—(C=O)—, ($C_3$-$C_{20}$)cycloalkenyl-O—(C=O)—, ($C_2$-$C_{20}$)alkynyl-O—(C=O)—, ($C_5$-$C_{25}$)aryl-O—(C=O), perhalo($C_1$-$C_{20}$)alkyl-O—(C=O)—, phenyl-O—(C=O)—, ($C_1$-$C_{20}$)alkyl-(C=O)—O—, ($C_3$-$C_{25}$)heteroaryl-(C=O)—O—, ($C_3$-$C_{25}$)heterocyclic-(C=O)—O—, ($C_2$-$C_{20}$)alkenyl-(C=O)—O—, ($C_3$-$C_{20}$)cycloalkenyl-(C=O)—O—, ($C_2$-$C_{20}$)alkynyl-(C=O)—O—, ($C_5$-$C_{25}$)aryl-(C=O)—O—, phenyl-(C=O)—O—, perhalo($C_1$-$C_{20}$)alkyl-(C=O)—O—, and salts thereof, and wherein $R^2$, $R^3$, $R^4$, $R^5$, $R^6$, $R^7$, $R^8$, $R^9$, $R^{10}$, and $R^{11}$ are each independently selected from the group consisting of hydrogen, hydroxy, halo, bromo, chloro, iodo, fluoro, —$N_3$, —CN, —NC, —SH, —$NO_2$, —$NH_2$, ($C_1$-$C_{20}$)alkyl, phenyl, ($C_3$-$C_{20}$)cycloalkyl, ($C_1$-$C_{20}$)alkoxy, ($C_3$-$C_{25}$)heteroaryl, ($C_3$-$C_{25}$)heterocyclic, ($C_2$-$C_{20}$)alkenyl, ($C_3$-$C_{20}$)cycloalkenyl, ($C_2$-$C_{20}$)alkynyl, ($C_5$-$C_{20}$)cycloalkynyl, ($C_5$-$C_{25}$)aryl, perhalo($C_1$-$C_{20}$)alkyl, ($C_1$-$C_{20}$)alkyl-O—, phenyl-O—, ($C_3$-$C_{20}$)cycloalkyl-O—, ($C_3$-$C_{25}$)heteroaryl-O—, ($C_3$-$C_{25}$)heterocyclic-O—, ($C_2$-$C_{20}$)alkenyl-O—, ($C_3$-$C_{20}$)cycloalkenyl-O—, ($C_2$-$C_{20}$)alkynyl-O—, ($C_5$-$C_{20}$)cycloalkynyl-O—, ($C_5$-$C_{25}$)aryl-O—, perhalo($C_1$-$C_{20}$)alkyl-O—, ($C_1$-$C_{20}$)alkyl-S—, phenyl-S—, ($C_3$-$C_{20}$)cycloalkyl-S—, ($C_3$-$C_{25}$)heteroaryl-S—, ($C_3$-$C_{25}$)heterocyclic-S—, ($C_2$-$C_{20}$)alkenyl-S—, ($C_3$-$C_{20}$)cycloalkenyl-S—, ($C_2$-$C_{20}$)alkynyl-S—, ($C_5$-$C_{20}$)cycloalkynyl-S—, ($C_5$-$C_{25}$)aryl-S—, perhalo($C_1$-$C_{20}$)alkyl-S—, ($C_1$-$C_{20}$)alkyl-$SO_2$—, phenyl-$SO_2$—, ($C_3$-$C_{20}$)cycloalkyl-$SO_2$—, ($C_1$-$C_{20}$)alkoxy-$SO_2$—, ($C_3$-$C_{25}$)heteroaryl-$SO_2$—, ($C_3$-$C_{25}$)heterocyclic-$SO_2$—, ($C_2$-$C_{20}$)alkenyl-$SO_2$—, ($C_3$-$C_{20}$)cycloalkenyl-$SO_2$—, ($C_2$-$C_{20}$)alkynyl-$SO_2$—, ($C_5$-$C_{20}$)cycloalkynyl-$SO_2$—, ($C_5$-$C_{25}$)aryl-$SO_2$—, perhalo($C_1$-$C_{20}$)alkyl-$SO_2$—, $H_2N$—$SO_2$—, ($C_1$-$C_{20}$)alkyl-NH—$SO_2$—, phenyl-NH—$SO_2$—, ($C_3$-$C_{20}$)cycloalkyl-NH—$SO_2$—, ($C_1$-$C_{20}$)alkoxy-NH—$SO_2$—, ($C_3$-$C_{25}$)heteroaryl-NH—$SO_2$—, ($C_3$-$C_{25}$)heterocyclic-NH—$SO_2$—, ($C_2$-$C_{20}$)alkenyl-NH—$SO_2$—, ($C_3$-$C_{20}$)cycloalkenyl-NH—$SO_2$—, ($C_2$-$C_{20}$)alkynyl-NH—$SO_2$—, ($C_5$-$C_{20}$)cycloalkynyl-NH—$SO_2$—, ($C_5$-$C_{25}$)aryl-NH—$SO_2$—, perhalo($C_1$-$C_{20}$)alkyl-NH—$SO_2$—, {($C_1$-$C_{20}$)alkyl}$_2$N—$SO_2$—, {phenyl}$_2$N—$SO_2$—, {($C_3$-$C_{20}$)cycloalkyl}$_2$N—$SO_2$—, {($C_1$-$C_{20}$)alkoxy}$_2$N—$SO_2$—, {($C_3$-$C_{25}$)heteroaryl}$_2$N—$SO_2$—, {($C_3$-$C_{25}$)heterocyclic}$_2$N—$SO_2$—, {($C_2$-$C_{20}$)alkenyl}$_2$N—$SO_2$—, {($C_2$-$C_{20}$)alkynyl}$_2$N—$SO_2$—, {($C_5$-$C_{20}$)cycloalkynyl}$_2$N—$SO_2$—, {($C_5$-$C_{25}$)aryl}$_2$N—$SO_2$—, {perhalo($C_1$-$C_{20}$)alkyl}$_2$N—$SO_2$—, ($C_1$-$C_{20}$)alkyl-$SO_2$—NH—, phenyl-$SO_2$—NH—, ($C_3$-$C_{20}$)cycloalkyl-$SO_2$—NH—, ($C_1$-$C_{20}$)alkoxy-$SO_2$—NH—, ($C_3$-$C_{25}$)heteroaryl-$SO_2$—NH—, ($C_3$-$C_{25}$)heterocyclic-$SO_2$—NH—, ($C_2$-$C_{20}$)alkenyl-$SO_2$—NH—, ($C_3$-$C_{20}$)cycloalkenyl-$SO_2$—NH—, ($C_2$-$C_{20}$)alkynyl-$SO_2$—NH—, ($C_5$-$C_{20}$)cycloalkynyl-$SO_2$—NH—, ($C_5$-$C_{25}$)aryl-$SO_2$—NH—, perhalo($C_1$-$C_{20}$)alkyl-$SO_2$—NH—, ($C_1$-$C_{20}$)alkyl-NH—, phenyl-NH—, ($C_3$-$C_{20}$)cycloalkyl-NH—, ($C_1$-$C_{20}$)alkoxy-NH—, ($C_3$-$C_{25}$)heteroaryl-NH—, ($C_3$-$C_{25}$)heterocyclic-NH—, ($C_2$-$C_{20}$)alkenyl-NH—, ($C_3$-$C_{20}$)cycloalkenyl-NH—, ($C_2$-$C_{20}$)alkynyl-NH—, ($C_5$-$C_{20}$)cycloalkynyl-NH—, ($C_5$-$C_{25}$)aryl-NH—, perhalo($C_1$-$C_{20}$)alkyl-NH—, {($C_1$-$C_{20}$)alkyl}$_2$N—, {phenyl}$_2$N—, {($C_3$-$C_{20}$)cycloalkyl}$_2$N—, {($C_1$-$C_{20}$)alkoxy}$_2$N—, {($C_3$-$C_{25}$)heteroaryl}$_2$N—, {($C_3$-$C_{25}$)heterocyclic}$_2$N—, {($C_2$-$C_{20}$)alkenyl}$_2$N—, {($C_3$-$C_{20}$)cycloalkenyl}$_2$N—, {($C_2$-$C_{20}$)alkynyl}$_2$N—, {($C_5$-$C_{20}$)cycloalkynyl}$_2$N—, {($C_5$-$C_{25}$)aryl}$_2$N—, {perhalo($C_1$-$C_{20}$)alkyl}$_2$N—, ($C_1$-$C_{20}$)alkyl-(C=O)—NH—, phenyl-(C=O)—NH—, ($C_3$-$C_{20}$)cycloalkyl-(C=O)—NH—, ($C_1$-$C_{20}$)alkoxy-(C=O)—NH—, ($C_3$-$C_{25}$)heteroaryl-(C=O)—NH—, ($C_3$-$C_{25}$)heterocyclic-(C=O)—NH—, ($C_2$-$C_{20}$)alkenyl-(C=O)—NH—, ($C_3$-$C_{20}$)cycloalkenyl-(C=O)—NH—, ($C_2$-$C_{20}$)alkynyl-(C=O)—NH—, ($C_5$-$C_{20}$)cycloalkynyl-(C=O)—NH—, ($C_5$-$C_{25}$)aryl-(C=O)—NH—, perhalo($C_1$-$C_{20}$)alkyl-(C=O)—NH—, ($C_1$-$C_{20}$)alkyl-(C=O)—{(($C_1$-$C_{20}$)alkyl)N}—, phenyl-(C=O)—{(($C_1$-$C_{20}$)alkyl)N}—, ($C_3$-$C_{20}$)cycloalkyl-(C=O)—{(($C_1$-$C_{20}$)alkyl)N}—, ($C_1$-$C_{20}$)alkoxy-(C=O){(($C_1$-$C_{20}$)alkyl)N}—, ($C_3$-$C_{25}$)heteroaryl-(C=O)—{(($C_1$-$C_{20}$)alkyl)N}—, ($C_3$-$C_{25}$)heterocyclic-(C=O)—{(($C_1$-$C_{20}$)alkyl)N}—, ($C_2$-$C_{20}$)alkenyl-(C=O)—{(($C_1$-$C_{20}$)alkyl)N}—, ($C_3$-$C_{20}$)cycloalkenyl-(C=O)—{(($C_1$-$C_{20}$)alkyl)N}—, ($C_2$-$C_{20}$)alkynyl-(C=O)—{(($C_1$-$C_{20}$)alkyl)N}—, ($C_5$-$C_{20}$)cycloalkynyl-(C=O)—{(($C_1$-$C_{20}$)alkyl)N}—, ($C_5$-$C_{25}$)aryl-(C=O)—{(($C_1$-$C_{20}$)alkyl)N}—, perhalo($C_1$-$C_{20}$)alkyl-(C=O)—{(($C_1$-$C_{20}$)alkyl)N}—, phenyl-(C=O)—NH—, phenyl-(C=O)—{(phenyl)N}—, ($C_1$-$C_{20}$)alkyl-(C=O)-{(phenyl)N}—, ($C_3$-$C_{20}$)cycloalkyl-(C=O)-{(phenyl)N}—, ($C_1$-$C_{20}$)alkoxy-(C=O)-{(phenyl)N}—, ($C_3$-$C_{25}$)heteroaryl-(C=O)-{(phenyl)N}—, ($C_3$-$C_{25}$)heterocyclic-(C=O)-{(phenyl)N}—, ($C_2$-$C_{20}$)alkenyl-(C=O)-{(phenyl)N}—, ($C_3$-$C_{20}$)cycloalkenyl-(C=O)-{(phenyl)N}—, ($C_2$-$C_{20}$)alkynyl-(C=O)-{(phenyl)N}—, ($C_5$-$C_{20}$)cycloalkynyl-(C=O)-{(phenyl)N}—, ($C_5$-$C_{25}$)aryl-(C=O)-{(phenyl)N}—, perhalo($C_1$-$C_{20}$)alkyl-(C=O)-{(phenyl)N}—, $H_2N$(C=O)—, ($C_1$-$C_{20}$)alkyl-NH—(C=O)—, phenyl-NH—(C=O), ($C_3$-$C_{20}$)cycloalkyl-NH—(C=O)—, ($C_1$-$C_{20}$)alkoxy-NH—(C=O)—, ($C_3$-$C_{25}$)heteroaryl-NH—(C=O)—, ($C_3$-$C_{25}$)heterocyclic-NH—(C=O)—, ($C_2$-$C_{20}$)alkenyl-NH—(C=O)—, ($C_3$-$C_{20}$)cycloalkenyl-NH—(C=O)—, ($C_2$-$C_{20}$)alkynyl-NH—(C=O)—, ($C_5$-$C_{20}$)cycloalkynyl-NH—(C=O)—, ($C_5$-$C_{25}$)aryl-NH—(C=O)—, perhalo($C_1$-$C_{20}$)alkyl-NH—(C=O)—, {$C_1$-$C_{20}$)alkyl}$_2$N—(C=O)—, {phenyl}{($C_1$-$C_{20}$)alkyl}N—(C=O)—, {($C_3$-$C_{20}$)cycloalkyl}{($C_1$-$C_{20}$)alkyl}N—(C=O)—, {($C_1$-$C_{20}$)alkoxy}{($C_1$-$C_{20}$)alkyl}N—(C=O)—, {($C_3$-$C_{25}$)heteroaryl}{($C_1$-$C_{20}$)alkyl}N—(C=O)—, {($C_3$-$C_{25}$)heterocyclic}{($C_1$-$C_{20}$)alkyl}N—(C=O)—, {($C_2$-$C_{20}$)alkenyl}{($C_1$-$C_{20}$)alkyl}N—(C=O)—, {($C_3$-$C_{20}$)cycloalkenyl}{($C_1$-$C_{20}$)alkyl}N—(C=O)—, {($C_2$-$C_{20}$)alkynyl}{($C_1$-$C_{20}$)alkyl}N—(C=O)—, {($C_5$-$C_{20}$)cycloalkynyl}{($C_1$-$C_{20}$)alkyl}N—(C=O)—, {($C_5$-$C_{25}$)aryl}{($C_1$-$C_{20}$)alkyl}N—(C=O)—, {perhalo($C_1$-$C_{20}$)alkyl}{($C_1$-$C_{20}$)alkyl}N—(C=O)—, (C=O)—, {phenyl}$_2$N—(C=O)—, {(C$_3$-C$_{20}$)cycloalkyl}{phenyl}N—(C=O)—, {(C$_1$-C$_{20}$)alkoxy}{phenyl}N—(C=O)—, {(C$_3$-C$_{25}$)heteroaryl}{phenyl}N—(C=O)—, {(C$_3$-C$_{25}$)heterocyclic}{phenyl}N—(C=O)—, {(C$_2$-C$_{20}$)alkenyl}{phenyl}N—(C=O)—, {(C$_3$-C$_{20}$)cycloalkenyl}{phenyl}N—(C=O)—, {(C$_2$-C$_{20}$)alkynyl}{phenyl}N—(C=O)—, {(C$_5$-C$_{20}$)cycloalkynyl}{phenyl}N—(C=O), {(C$_5$-C$_{25}$)aryl}{phenyl}N—(C=O)—, {perhalo(C$_1$-C$_{20}$)alkyl}{phenyl}N—(C=O)—, HO—(C=O)—, (C$_1$-C$_{20}$)alkyl-(C=O)—, (C$_3$-C$_{25}$)heteroaryl-(C=O)—, (C$_3$-C$_{25}$)heterocyclic-(C=O)—, (C$_2$-C$_{20}$)alkenyl-(C=O)—, (C$_3$-C$_{20}$)cycloalkenyl-(C=O)—, (C$_2$-C$_{20}$)alkynyl-(C=O)—, (C$_5$-C$_{25}$)aryl-(C=O)—, perhalo(C$_1$-C$_{20}$)alkyl-(C=O)—, phenyl-(C=O)—, (C$_1$-C$_{20}$)alkyl-O—(C=O)—, (C$_3$-C$_{25}$)heteroaryl-O—(C=O)—, (C$_3$-C$_{25}$)heterocyclic-O—(C=O)—, (C$_2$-C$_{20}$)alkenyl-O—(C=O)—, (C$_3$-C$_{20}$)cycloalkenyl-O—(C=O)—, (C$_2$-C$_{20}$)alkynyl-O—(C=O)—, (C$_5$-C$_{25}$)aryl-O—(C=O), perhalo(C$_1$-C$_{20}$)alkyl-O—(C=O)—, phenyl-O—(C=O)—, (C$_1$-C$_{20}$)alkyl-(C=O)—O—, (C$_3$-C$_{25}$)heteroaryl-(C=O)—O—, (C$_3$-C$_{25}$)heterocyclic-(C=O)—O—, (C$_2$-C$_{20}$)alkenyl-(C=O)—O—, (C$_3$-C$_{20}$)cycloalkenyl-(C=O)—O—, (C$_2$-C$_{20}$)alkynyl-(C=O)—O—, (C$_5$-C$_{25}$)aryl-(C=O)—O—, phenyl-(C=O)—O—, perhalo(C$_1$-C$_{20}$)alkyl-(C=O)—O—, and salts thereof;

wherein each of the aforesaid (C$_1$-C$_{20}$)alkyl, phenyl, (C$_3$-C$_{20}$)cycloalkyl, (C$_1$-C$_{20}$)alkoxy, (C$_3$-C$_{25}$)heteroaryl, (C$_3$-C$_{25}$)heterocyclic, (C$_2$-C$_{20}$)alkenyl, (C$_3$-C$_{20}$) cycloalkenyl, (C$_2$-C$_{20}$)alkynyl, (C$_5$-C$_{20}$)cycloalkynyl, and (C$_5$-C$_{25}$) aryl groups (for said R$^2$, R$^3$, R$^4$, R$^5$, R$^6$, R$^7$, R$^8$, R$^9$, R$^{10}$, and R$^{11}$ groups) may be optionally and independently substituted by one to four moieties selected from the group consisting of hydroxy, halo, bromo, chloro, iodo, fluoro, —N$_3$, —CN, —NC, —SH, —NO$_2$—, —NH$_2$, (C$_1$-C$_{20}$)alkyl, phenyl, (C$_3$-C$_{20}$)cycloalkyl, (C$_1$-C$_{20}$)alkoxy, (C$_3$-C$_{25}$)heteroaryl, (C$_3$-C$_{25}$)heterocyclic, (C$_2$-C$_{20}$)alkenyl, (C$_3$-C$_{20}$)cycloalkenyl, (C$_2$-C$_{20}$)alkynyl, (C$_5$-C$_{20}$)cycloalkynyl, (C$_5$-C$_{25}$)aryl, perhalo(C$_1$-C$_{20}$)alkyl, (C$_1$-C$_{20}$)alkyl-O—, phenyl-O—, (C$_3$-C$_{20}$)cycloalkyl-O—, (C$_3$-C$_{25}$)heteroaryl-O—, (C$_3$-C$_{25}$)heterocyclic-O—, (C$_2$-C$_{20}$)alkenyl-O—, (C$_3$-C$_{20}$) cycloalkenyl-O—, (C$_2$-C$_{20}$)alkynyl-O—, (C$_5$-C$_{20}$)cycloalkynyl-O—, (C$_5$-C$_{25}$)aryl-O—, perhalo(C$_1$-C$_{20}$)alkyl-O—, (C$_1$-C$_{20}$)alkyl-S—, phenyl-S—, (C$_3$-C$_{20}$)cycloalkyl-S—, (C$_3$-C$_{25}$)heteroaryl-S—, (C$_3$-C$_{25}$)heterocyclic-S—, (C$_2$-C$_{20}$)alkenyl-S—, (C$_3$-C$_{20}$)cycloalkenyl-S—, (C$_2$-C$_{20}$)alkynyl-S—, (C$_5$-C$_{20}$)cycloalkynyl-S—, (C$_5$-C$_{25}$)aryl-S—, perhalo(C$_1$-C$_{20}$)alkyl-S—, (C$_1$-C$_{20}$)alkyl-SO$_2$—, phenyl-SO$_2$—, (C$_3$-C$_{20}$)cycloalkyl-SO$_2$—, (C$_1$-C$_{20}$)alkoxy-SO$_2$—, (C$_3$-C$_{25}$)heteroaryl-SO$_2$—, (C$_3$-C$_{25}$)heterocyclic-SO$_2$—, (C$_2$-C$_{20}$)alkenyl-SO$_2$—, (C$_3$-C$_{20}$)cycloalkenyl-SO$_2$—, (C$_2$-C$_{20}$)alkynyl-SO$_2$—, (C$_5$-C$_{20}$)cycloalkynyl-SO$_2$—, (C$_5$-C$_{25}$)aryl-SO$_2$—, perhalo(C$_1$-C$_{20}$)alkyl-SO$_2$—, H$_2$N—SO$_2$—, (C$_1$-C$_{20}$)alkyl-NH—SO$_2$—, phenyl-NH—SO$_2$—, (C$_3$-C$_{20}$)cycloalkyl-NH—SO$_2$—, (C$_1$-C$_{20}$)alkoxy-NH—SO$_2$—, (C$_3$-C$_{25}$)heteroaryl-NH—SO$_2$—, (C$_3$-C$_{25}$)heterocyclic-NH—SO$_2$—, (C$_2$-C$_{20}$)alkenyl-NH—SO$_2$—, (C$_3$-C$_{20}$)cycloalkenyl-NH—SO$_2$—, (C$_2$-C$_{20}$)alkynyl-NH—SO$_2$—, (C$_5$-C$_{20}$)cycloalkynyl-NH—SO$_2$—, (C$_5$-C$_{25}$)aryl-NH—SO$_2$—, perhalo(C$_1$-C$_{20}$)alkyl-NH—SO$_2$—, {(C$_1$-C$_{20}$)alkyl}$_2$N—SO$_2$—, {phenyl}$_2$N—SO$_2$—, {(C$_3$-C$_{20}$)cycloalkyl}$_2$N—SO$_2$—, {(C$_1$-C$_{20}$)alkoxy}$_2$N—SO$_2$—, {(C$_3$-C$_{25}$)heteroaryl}$_2$N—SO$_2$—, {(C$_3$-C$_{25}$)heterocyclic}$_2$N—SO$_2$—, {(C$_2$-C$_{20}$)alkenyl}$_2$N—SO$_2$—, {(C$_2$-C$_{20}$)alkynyl}$_2$N—SO$_2$—, {(C$_5$-C$_{20}$)cycloalkynyl}$_2$N—SO$_2$—, {(C$_5$-C$_{25}$)aryl}$_2$N—SO$_2$—, {perhalo(C$_1$-C$_{20}$)alkyl}$_2$N—SO$_2$—, (C$_1$-C$_{20}$)alkyl-SO$_2$—NH—, phenyl-SO$_2$—NH—, (C$_3$-C$_{20}$)cycloalkyl-SO$_2$—NH—, (C$_1$-C$_{20}$)alkoxy-SO$_2$—NH—, (C$_3$-C$_{25}$)heteroaryl-SO$_2$—NH—, (C$_3$-C$_{25}$)heterocyclic-SO$_2$—NH—, (C$_2$-C$_{20}$)alkenyl-SO$_2$—NH—, (C$_3$-C$_{20}$)cycloalkenyl-SO$_2$—NH—, (C$_2$-C$_{20}$)alkynyl-SO$_2$—NH—, (C$_5$-C$_{20}$)cycloalkynyl-SO$_2$—NH—, (C$_5$-C$_{25}$)aryl-SO$_2$—NH—, perhalo(C$_1$-C$_{20}$)alkyl-SO$_2$—NH—, (C$_1$-C$_{20}$)alkyl-NH—, phenyl-NH—, (C$_3$-C$_{20}$)cycloalkyl-NH—, (C$_1$-C$_{20}$)alkoxy-NH—, (C$_3$-C$_{25}$)heteroaryl-NH—, (C$_3$-C$_{25}$)heterocyclic-NH—, (C$_2$-C$_{20}$)alkenyl-NH—, (C$_3$-C$_{20}$)cycloalkenyl-NH—, (C$_2$-C$_{20}$)alkynyl-NH—, (C$_5$-C$_{20}$)cycloalkynyl-NH—, (C$_5$-C$_{25}$)aryl-NH—, perhalo(C$_1$-C$_{20}$)alkyl-NH—, {(C$_1$-C$_{20}$)alkyl}$_2$N—, {phenyl}$_2$N—, {(C$_3$-C$_{20}$)cycloalkyl}$_2$N—, {(C$_1$-C$_{20}$)alkoxy}$_2$N—, {(C$_3$-C$_{25}$)heteroaryl}$_2$N—, {(C$_3$-C$_{25}$)heterocyclic}$_2$N—, {(C$_2$-C$_{20}$)alkenyl}$_2$N—, {(C$_3$-C$_{20}$)cycloalkenyl}$_2$N—, {(C$_2$-C$_{20}$)alkynyl}$_2$N—, {(C$_5$-C$_{20}$)cycloalkynyl}$_2$N—, {(C$_5$-C$_{25}$)aryl}$_2$N—, {perhalo(C$_1$-C$_{20}$)alkyl}$_2$N—, (C$_1$-C$_{20}$)alkyl-(C=O)—NH—, phenyl-(C=O)—NH—, (C$_3$-C$_{20}$)cycloalkyl-(C=O)—NH—, (C$_1$-C$_{20}$)alkoxy-(C=O)—NH—, (C$_3$-C$_{25}$)heteroaryl-(C=O)—NH—, (C$_3$-C$_{25}$)heterocyclic-(C=O)—NH—, (C$_2$-C$_{20}$)alkenyl-(C=O)—NH—, (C$_3$-C$_{20}$)cycloalkenyl-(C=O)—NH—, (C$_2$-C$_{20}$)alkynyl-(C=O)—NH—, (C$_5$-C$_{20}$)cycloalkynyl-(C=O)—NH—, (C$_5$-C$_{25}$)aryl-(C=O)—NH—, perhalo(C$_1$-C$_{20}$)alkyl-(C=O)—NH—, (C$_1$-C$_{20}$)alkyl-(C=O)—{((C$_1$-C$_{20}$)alkyl)N}—, phenyl-(C=O)—{((C$_1$-C$_{20}$)alkyl)N}—, (C$_3$-C$_{20}$)cycloalkyl-(C=O)—{((C$_1$-C$_{20}$)alkyl)N}—, (C$_1$-C$_{20}$)alkoxy-(C=O)—{((C$_1$-C$_{20}$)alkyl)N}—, (C$_3$-C$_{25}$)heteroaryl-(C=O)—{((C$_1$-C$_{20}$)alkyl)N}—, (C$_3$-C$_{25}$)heterocyclic-(C=O)—{((C$_1$-C$_{20}$)alkyl)N}—, (C$_2$-C$_{20}$)alkenyl-(C=O)—{((C$_1$-C$_{20}$)alkyl)N}—, (C$_3$-C$_{20}$) cycloalkenyl-(C=O)—{((C$_1$-C$_{20}$)alkyl)N}—, (C$_2$-C$_{20}$)alkynyl-(C=O)—{((C$_1$-C$_{20}$)alkyl)N}—, (C$_5$-C$_{20}$) cycloalkynyl-(C=O)—{((C$_1$-C$_{20}$)alkyl)N}—, (C$_5$-C$_{25}$) aryl-(C=O)—{((C$_1$-C$_{20}$)alkyl)N}—, perhalo(C$_1$-C$_{20}$)alkyl-(C=O)—{((C$_1$-C$_{20}$)alkyl)N}—, phenyl-(C=O)—NH—, phenyl-(C=O)-{(phenyl)N}—, (C$_1$-C$_{20}$)alkyl-(C=O)-{(phenyl)N}—, (C$_3$-C$_{20}$)cycloalkyl-(C=O)-{(phenyl)N}—, (C$_1$-C$_{20}$)alkoxy-(C=O)-{(phenyl)N}—, (C$_3$-C$_{25}$)heteroaryl-(C=O)-{(phenyl)N}—, (C$_3$-C$_{25}$)heterocyclic-(C=O)-{(phenyl)N}—, (C$_2$-C$_{20}$)alkenyl-(C=O)-{-(phenyl)N}—, (C$_3$-C$_{20}$)cycloalkenyl-(C=O)-{(phenyl)N}—, (C$_2$-C$_{20}$)alkynyl-(C=O)-{(phenyl)N}—, (C$_5$-C$_{20}$)cycloalkynyl-(C=O)-{(phenyl)N}—, (C$_5$-C$_{25}$) aryl-(C=O)-{(phenyl)N}—, perhalo(C$_1$-C$_{20}$)alkyl-(C=O)-{phenyl)N}—, H$_2$N(C=O)—, (C$_1$-C$_{20}$)alkyl-NH—(C=O)—, phenyl-NH—(C=O)—, (C$_3$-C$_{20}$) cycloalkyl-NH—(C=O)—, (C$_1$-C$_{20}$)alkoxy-NH—(C=O)—, (C$_3$-C$_{25}$)heteroaryl-NH—(C=O)—, (C$_3$-C$_{25}$) heterocyclic-NH—(C=O)—, (C$_2$-C$_{20}$)alkenyl-NH—(C=O)—, (C$_3$-C$_{20}$)cycloalkenyl-NH—(C=O)—, (C$_2$-C$_{20}$)alkynyl-NH—(C=O)—, (C$_5$-C$_{20}$)cycloalkynyl-NH—(C=O)—, (C$_5$-C$_{25}$)aryl-NH—(C=O)—, perhalo(C$_1$-C$_{20}$) alkyl-NH—(C=O)—, {(C$_1$-C$_{20}$)alkyl}$_2$N—(C=O)—, {phenyl}{(C$_1$-C$_{20}$)alkyl}N—(C=O)—, {(C$_3$-C$_{20}$)cycloalkyl}{(C$_1$-C$_{20}$)alkyl}N—(C=O)—, {(C$_1$-C$_{20}$)alkoxy}{(C$_1$-C$_{20}$)alkyl}N—(C=O)—, {(C$_3$-C$_{25}$)heteroaryl}{(C$_1$-C$_{20}$)alkyl}N—(C=O)—, {(C$_3$-C$_{25}$)heterocyclic}{(C$_1$-C$_{20}$)alkyl}N—(C=O)—, {(C$_2$-C$_{20}$)alkenyl}{(C$_1$-C$_{20}$)alkyl}N—(C=O)—, {(C$_3$-C$_{20}$)cycloalkenyl}{(C$_1$-C$_{20}$)alkyl}N—(C=O)—, {(C$_2$-C$_{20}$)alkynyl}{(C$_1$-C$_{20}$)alkyl}N—(C=O)—, {(C$_5$-C$_{20}$)cycloalkynyl}{(C$_1$-C$_{20}$)alkyl}N—(C=O)—, {(C$_5$-C$_{25}$)aryl}{(C$_1$-C$_{20}$)alkyl}N—(C=O)—, {perhalo(C$_1$-C$_{20}$)alkyl}{(C$_1$-C$_{20}$)alkyl}N—(C=O)—, {phenyl}$_2$N—(C=O)—, {(C$_3$-C$_{20}$)cycloalkyl}{phenyl}N—(C=O)—, {($C_1$-$C_{20}$)alkoxy}{phenyl}N—(C=O)—, {($C_3$-$C_{25}$)heteroaryl}{phenyl}N—(C=O)—, {($C_3$-$C_{25}$)heterocyclic}{phenyl}N—(C=O)—, {($C_2$-$C_{20}$)alkenyl}{phenyl}N—(C=O)—, {($C_3$-$C_{20}$)cycloalkenyl}{phenyl}N—(C=O)—, {($C_2$-$C_{20}$)alkynyl}{phenyl}N—(C=O)—, {($C_5$-$C_{25}$)cycloalkynyl}{phenyl}N—(C=O)—, {($C_5$-$C_{25}$)aryl}{phenyl}N—(C=O)—, {perhalo($C_1$-$C_{20}$)alkyl}{phenyl}N—(C=O)—, HO—(C=O)—, ($C_1$-$C_{20}$)alkyl-(C=O)—, ($C_3$-$C_{25}$)heteroaryl-(C=O)—, ($C_3$-$C_{25}$)heterocyclic-(C=O)—, ($C_2$-$C_{20}$)alkenyl-(C=O), ($C_3$-$C_{20}$)cycloalkenyl-(C=O)—, ($C_2$-$C_{20}$)alkynyl-(C=O)—, ($C_5$-$C_{25}$)aryl-(C=O)—, perhalo($C_1$-$C_{20}$)alkyl-(C=O)—, phenyl-(C=O)—, ($C_1$-$C_{20}$)alkyl-O—(C=O)—, ($C_3$-$C_{25}$)heteroaryl-O—(C=O)—, ($C_3$-$C_{25}$)heterocyclic-O—(C=O), ($C_2$-$C_{20}$)alkenyl-O—(C=O)—, ($C_3$-$C_{20}$) cycloalkenyl-O—(C=O)—, ($C_2$-$C_{20}$)alkynyl-O—(C=O)—, ($C_5$-$C_{25}$)aryl-O—(C=O)—, perhalo($C_1$-$C_{20}$)alkyl-O—(C=O)—, phenyl-O—(C=O)—, ($C_1$-$C_{20}$)alkyl-(C=O)—O—, ($C_3$-$C_{25}$)heteroaryl-(C=O)—O—, ($C_3$-$C_{25}$)heterocyclic-(C=O)—O—, ($C_2$-$C_{20}$)alkenyl-(C=O)—O—, ($C_3$-$C_{20}$)cycloalkenyl-(C=O)—O—, ($C_2$-$C_{20}$)alkynyl-(C=O)—O—, ($C_1$-$C_{25}$)aryl-(C=O)—O—, phenyl-(C=O)—O—, perhalo($C_1$-$C_{20}$)alkyl-(C=O)—O—, and salts thereof, and wherein two independently chosen $R^2$, $R^3$, $R^4$, $R^5$, $R^6$, $R^7$, $R^8$, $R^9$, $R^{10}$, and $R^{11}$ alkyl-containing groups may be taken together with any atom to which they are attached to form a three to forty membered cyclic, heterocyclic or heteroaryl ring.

In the present application, GhyCH— is $NH_2C(=NH)$—NH—N=CH—; and GhyCH$_3$— is $NH_2C(=NH)$—NH—N=CCH$_3$.

In one embodiment, Z is a $C_1$-$C_{20}$ alkylene, which may be branched or unbranched, saturated or unsaturated, substituted or unsubstituted, and which may have one or more carbon atoms replaced by one or more heteroatoms selected from the group consisting of oxygen, nitrogen, sulfur, and a combination thereof. This includes alkylenes having 1, 2, 3, 4, 5, 6, 7, 8, 9, 10, 11, 12, 13, 14, 15, 16, 17, 18, 19, and 20 carbons.

In another embodiment, Z is a branched $C_1$-$C_{20}$ alkylene.

In another embodiment, Z is an unbranched $C_1$-$C_{20}$ alkylene.

In another embodiment, Z is a saturated $C_1$-$C_{20}$ alkylene.

In another embodiment, Z is an unsaturated $C_1$-$C_{20}$ alkylene.

In another embodiment, Z is an unsubstituted $C_1$-$C_{20}$ alkylene.

In another embodiment, Z is a substituted $C_1$-$C_{20}$ alkylene.

In another embodiment, Z is a $C_1$-$C_{20}$ alkylene in which one or more carbons is replaced with one or more heteroatoms selected from the group including oxygen, nitrogen, sulfur and a combination thereof.

In one embodiment, Z is a saturated or unsaturated, substituted or unsubstituted $C_3$-$C_{20}$ cycloalkylene, and which may have one or more carbon atoms replaced by one or more heteroatoms selected from the group consisting of oxygen, nitrogen, sulfur, and a combination thereof. This includes cycloalkylenes having 3, 4, 5, 6, 7, 8, 9, 10, 11, 12, 13, 14, 15, 16, 17, 18, 19, and 20 carbons.

In another embodiment, Z is a saturated $C_3$-$C_{20}$ cycloalkylene.

In another embodiment, Z is an unsaturated $C_3$-$C_{20}$ cycloalkylene.

In another embodiment, Z is an unsubstituted $C_3$-$C_{20}$ cycloalkylene.

In another embodiment, Z is a substituted $C_3$-$C_{20}$ cycloalkylene.

In another embodiment, Z is a $C_3$-$C_{20}$ cycloalkylene in which one or more carbons is replaced with one or more heteroatoms selected from the group including oxygen, nitrogen, sulfur and a combination thereof.

In one embodiment, Z is a substituted or unsubstituted $C_5$-$C_{25}$ arylene, wherein one or more carbon atoms in the cycloalkylene and arylene may be replaced with one or more heteroatoms selected from the group consisting of nitrogen, oxygen, sulfur, and a combination thereof. This includes arylenes having 6, 7, 8, 9, 10, 11, 12, 13, 14, 15, 16, 17, 18, 19, 20, 21, 22, 23, 24, and 25 carbons.

In another embodiment, Z is a substituted $C_5$-$C_{25}$ arylene.

In another embodiment, Z is an unsubstituted $C_5$-$C_{25}$ arylene.

In another embodiment, Z is a $C_5$-$C_{25}$ arylene in which one or more carbons is replaced with one or more heteroatoms selected from the group including oxygen, nitrogen, sulfur and a combination thereof.

In one embodiment, Z is an —$NR^8(CO)NR^9$— group, optionally in the salt form, wherein the R groups are both hydrogen.

In another embodiment, Z is a —($C_6H_4$)— group.

In another embodiment, Z is a —$(CH_2)_p$— group, wherein p is 1, 2, 3, 4, 5, 6, 7, 8, 9, or 10.

In another embodiment, Z is a —($C_5H_3N$)— group.

In another embodiment, Z is a —O—$(CH_2)_p$—O— group, wherein p is 1, 2, 3, 4, 5, 6, 7, 8, 9, or 10.

In another embodiment, Z is a —A—$(CH_2)_p$—A— group, wherein p is 1, 2, 3, 4, 5, 6, 7, 8, 9, or 10, and wherein the A's are each independently —NH(CO)—, —(CO)NH—, or —NH(CO)NH— groups.

In another embodiment, Z is a —A—($C_6H_4$)—A— wherein the A's are each independently —CO—, —NH(CO)—, —(CO)NH—, or —NH(CO)NH— groups.

In another embodiment, Z is —O—($C_6H_4$)—O—, wherein the two "—O—" groups are para to each other about the phenylene ring.

In another embodiment, Z is —O—($C_6H_4$)—O—, wherein the two "—O—" groups are meta to each other about the phenylene ring.

In another embodiment, Z is —O—$CH_2$—$CH_2$—O—$CH_2$—$CH_2$—O—.

In another embodiment, Z is a group having the formula:

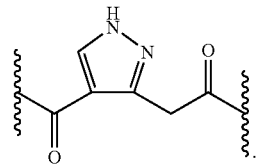

In another embodiment, Z is a group having the formula:

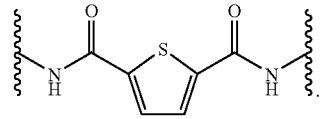

In another embodiment, Z is a group having the formula:

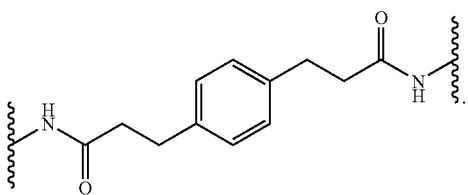

In another embodiment, Z is a group having the formula:

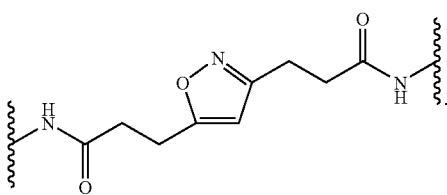

In another embodiment, Z is a group having the formula:

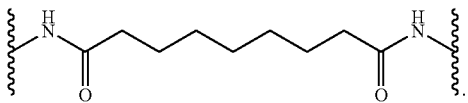

In another embodiment, Z is a group having the formula:

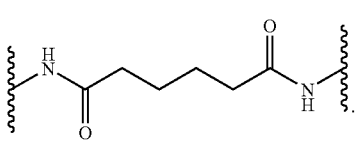

In another embodiment, Z is a group having the formula:

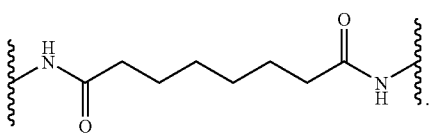

In another embodiment, Z is a group having the formula:

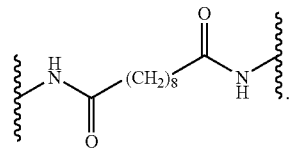

In one embodiment, the compound includes the structure:

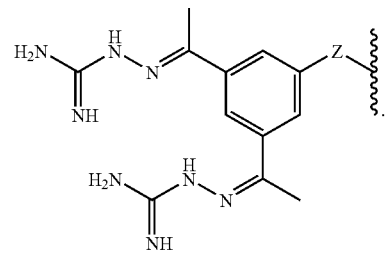

In one embodiment, the compound includes the structure:

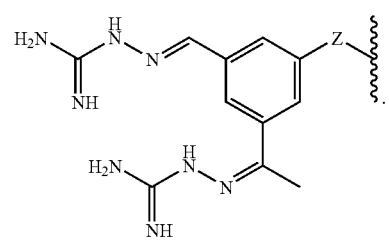

In one embodiment, the compound includes the structure:

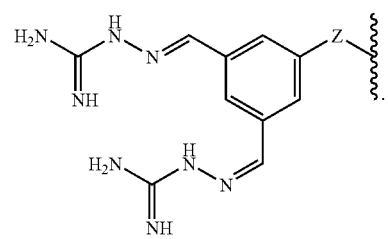

In one embodiment, the compound includes the structure:

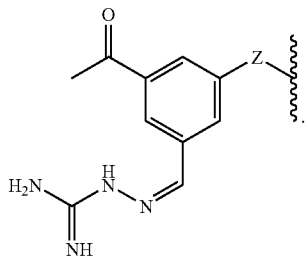

In one embodiment, the compound includes the structure:

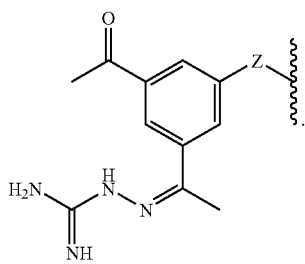

In one embodiment, the compound includes the structure:

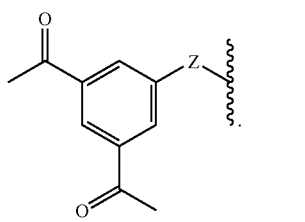

In one embodiment, the compound includes the structure:

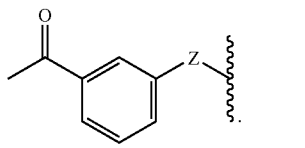

In one embodiment, the compound includes the structure:

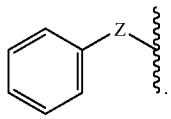

In one embodiment, the compound includes the structure:

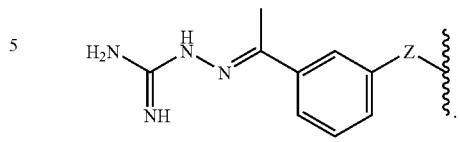

In one embodiment, the compound includes the structure:

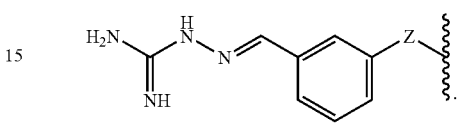

In the compound, $X^1$, $X^2$, $X^3$, and $X^4$ may each individually adopt the ortho, meta or para position on the phenylene ring relative to the Z group. In another embodiment, the $X^1$, $X^2$, $X^3$, and $X^4$ are meta or para to the Z group. In another embodiment, the non-H $X^1$, $X^2$, $X^3$, and $X^4$ groups are meta to both the Z group and to each other.

As used herein, the formula "—NH(CO)—" includes the "—(CO)NH—" isomer.

In one embodiment, at least one of $X^1$, $X^2$, $X^3$ and $X^4$ is GhyCH— or GhyCCH$_3$—, $X^1$ and $X^2$ are not simultaneously H, and $X^3$ and $X^4$ are not simultaneously H.

In another embodiment, $X^1$, $X^2$, $X^3$, and $X^4$ are selected from the group including GhyCH— or GhyCCH$_3$—.

In another embodiment, $X^1$, $X^2$, $X^3$, and $X^4$ are selected from the group including GhyCH—, GhyCCH$_3$—, or CH$_3$CO—.

In another embodiment, $X^1$, $X^2$, $X^3$, and $X^4$ are each GhyCH—.

In another embodiment, the $X^1$, $X^2$, $X^3$, and $X^4$ are each GhyCCH$_3$—.

In another embodiment, the $X^1$, $X^2$, $X^3$, and $X^4$ are each CH$_3$CO—.

In another embodiment, at least one of $X^1$, $X^2$, $X^3$, and $X^4$ is CH$_3$CO—.

In one embodiment, the compound is in the salt form.

In another embodiment, the compound is in the salt form having a compound:salt ratio of 1:1, 1:2, 1:3, 1:4 or 2:1.

In one embodiment, Z has the formula:

$$-(A^1)_a-(CR^2R^3)_x-Q_m-(CR^4R^5)_y-T_n-(CR^6R^7)_z-(A^2)_b-;$$

wherein each of the variables a, m, n, and b are equal to 1; and the sum of the variables x, y and z does not exceed 12;

and wherein Q, T, $A^1$, $R^2$, $R^3$, $R^4$, $R^5$, $R^6$, $R^7$, $A^2$, $R^{10}$, and $R^{11}$ are defined herein.

In one embodiment, Z has the formula:

$$-(A^1)_a-(CR^2R^3)_x-Q_m-(CR^4R^5)_y-T_n-(CR^6R^7)_z-(A^2)_b-;$$

wherein each of the variables a, m, n, and b are equal to 1; and the sum of the variables x, y and z does not exceed 12;

wherein Q and T are each independently selected from the group consisting $R^{10}$(CO)NR$^{11}$—, —(CO)NR$^{10}$—, —NR$^{10}$ (CO)—, —NR$^{10}$—, salts thereof, —O—, optionally substituted alkylene, optionally substituted arylene, optionally substituted heteroarylene, and combinations thereof;

and wherein A$^1$, R$^2$, R$^3$, R$^4$, R$^5$, R$^6$, R$^7$, A$^2$, R$^{10}$, and R$^{11}$ are defined herein.

In one embodiment, Z has the formula:

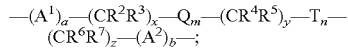

wherein each of the variables a, m, n, and b are equal to 1; and the sum of the variables x, y and z does not exceed 12;

wherein Q and T are each independently selected from the group consisting R$^{10}$(CO)NR$^{11}$—, —(CO)NR$^{10}$—, —NR$^{10}$(CO)—, —NR$^{10}$—, salts thereof, —O—, optionally substituted alkylene, optionally substituted arylene, optionally substituted heteroarylene, and combinations thereof;

and wherein A$^1$, R$^2$, R$^3$, R$^4$, R$^5$, R$^6$, R$^7$, A$^2$, R$^{10}$, and R$^{11}$ are defined herein;

with the proviso that if Q is —NR$^{10}$— or —O— and y is 1 then T is not —NR$^{10}$— or —O—.

In one embodiment, Z has the formula:

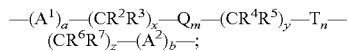

wherein each of the variables a, m, n, and b are equal to 1; and the sum of the variables x, y and z does not exceed 12;

wherein Q and T are each independently selected from the group consisting R$^{10}$(CO)NR$^{11}$—, —(CO)NR$^{10}$—, —NR$^{10}$(CO)—, —NR$^{10}$—, salts thereof, —O—, optionally substituted alkylene, optionally substituted arylene, optionally substituted heteroarylene, and combinations thereof;

and wherein A$^1$, R$^2$, R$^3$, R$^4$, R$^5$, R$^6$, R$^7$, A$^2$, R$^{10}$, and R$^{11}$ are defined herein;

with the proviso that if Q is —NR$^{10}$— or —O— and y is 1 then T is not —NR$^{10}$— or —O—;

and with the proviso that if Q is —(CO)NR$^{10}$—, —NR$^{10}$(CO)—, —NR$^{10}$—, or —O— and y is 1 then T is not —(CO)NR$^{10}$—, —NR$^{10}$(CO)—, —NR$^{10}$— or —O—.

In another embodiment, Z has the formula:

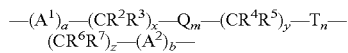

wherein Q and T are each independently selected from the group consisting R$^{10}$(CO)NR$^{11}$—, —(CO)NR$^{10}$—, —NR$^{10}$(CO)—, —NR$^{10}$—, salts thereof, —O—, optionally substituted alkylene, optionally substituted arylene, optionally substituted heteroarylene, and combinations thereof;

wherein A$^1$, R$^2$, R$^3$, R$^4$, R$^5$, R$^6$, R$^7$, A$^2$, R$^{10}$, and R$^{11}$ are defined herein;

wherein if substituted, the alkylene, arylene, and/or heteroarylene are each independently substituted with 0 to 4 groups selected from the group consisting of H, halogen, OR, NR$^1$R$^{1'}$, NR$^1$CO, CONR$^1$, COR$^1$, SR$^1$, SO$_2$R$^1$, SO$_2$NR$^1$, SOR$^1$, alkyl, aryl, heteroalkyl, and heteroaryl, salts thereof, and combinations thereof;

R$^1$ and R$^{1'}$ being each independently selected from the group including hydrogen, hydroxy, halo, bromo, chloro, iodo, fluoro, —N$_3$, —CN, —NC, —SH, —NO$_2$, —NH$_2$, (C$_1$-C$_{20}$)alkyl, phenyl, (C$_3$-C$_{20}$)cycloalkyl, (C$_1$-C$_{20}$)alkoxy, (C$_3$-C$_{25}$)heteroaryl, (C$_3$-C$_{25}$)heterocyclic, (C$_2$-C$_{20}$)alkenyl, (C$_3$-C$_{20}$)cycloalkenyl, (C$_2$-C$_{20}$)alkynyl, (C$_5$-C$_{20}$)cycloalkynyl, (C$_5$-C$_{25}$)aryl, perhalo(C$_1$-C$_{20}$)alkyl, (C$_1$-C$_{20}$)alkyl-O—, phenyl-O—, (C$_3$-C$_{20}$)cycloalkyl-O—, (C$_3$-C$_{25}$)heteroaryl-O—, (C$_3$-C$_{25}$)heterocyclic-O—, (C$_2$-C$_{20}$)alkenyl-O—, (C$_3$-C$_{20}$) cycloalkenyl-O—, (C$_2$-C$_{20}$)alkynyl-O—, (C$_5$-C$_{25}$)cycloalkynyl-O—, (C$_5$-C$_{25}$)aryl-O—, perhalo(C$_1$-C$_{20}$)alkyl-O—, (C$_1$-C$_{20}$)alkyl-S—, phenyl-S—, (C$_3$-C$_{20}$)cycloalkyl-S—, (C$_3$-C$_{25}$)heteroaryl-S—, (C$_3$-C$_{25}$)heterocyclic-S—, (C$_2$-C$_{20}$)alkenyl-S—, (C$_3$-C$_{20}$)cycloalkenyl-S—, (C$_2$-C$_{20}$)alkynyl-S—, (C$_5$-C$_{20}$)cycloalkynyl-S—, (C$_5$-C$_{25}$)aryl-S—, perhalo(C$_1$-C$_{20}$)alkyl-S—, (C$_1$-C$_{20}$)alkyl-SO$_2$—, phenyl-SO$_2$—, (C$_3$-C$_{20}$)cycloalkyl-SO$_2$—, (C$_1$-C$_{20}$)alkoxy-SO$_2$—, (C$_3$-C$_{25}$)heteroaryl-SO$_2$—, (C$_3$-C$_{25}$)heterocyclic-SO$_2$—, (C$_2$-C$_{20}$)alkenyl-SO$_2$—, (C$_3$-C$_{20}$)cycloalkenyl-SO$_2$—, (C$_2$-C$_{20}$)alkynyl-SO$_2$—, (C$_5$-C$_{20}$)cycloalkynyl-SO$_2$—, (C$_5$-C$_{25}$)aryl-SO$_2$—, perhalo(C$_1$-C$_{20}$)alkyl-SO$_2$—, H$_2$N—SO$_2$—, (C$_1$-C$_{20}$)alkyl-NH—SO$_2$—, phenyl-NH—SO$_2$—, (C$_3$-C$_{20}$)cycloalkyl-NH—SO$_2$—, (C$_1$-C$_{20}$)alkoxy-NH—SO$_2$—, (C$_3$-C$_{25}$)heteroaryl-NH—SO$_2$—, (C$_3$-C$_{25}$)heterocyclic-NH—SO$_2$—, (C$_2$-C$_{20}$)alkenyl-NH—SO$_2$—, (C$_3$-C$_{20}$)cycloalkenyl-NH—SO$_2$—, (C$_2$-C$_{20}$)alkynyl-NH—SO$_2$—, (C$_1$-C$_{20}$)cycloalkynyl-NH—SO$_2$—, (C$_5$-C$_{25}$)aryl-NH—SO$_2$—, perhalo(C$_1$-C$_{20}$)alkyl-NH—SO$_2$—, {(C$_1$-C$_{20}$)alkyl}$_2$N—SO$_2$—, {phenyl}$_2$N—SO$_2$—, {(C$_3$-C$_{20}$)cycloalkyl}$_2$N—SO$_2$—, {(C$_1$-C$_{20}$)alkoxy}$_2$N—SO$_2$—, {(C$_3$-C$_{25}$)heteroaryl}$_2$N—SO$_2$—, {(C$_3$-C$_{25}$)heterocyclic}$_2$N—SO$_2$—, {(C$_2$-C$_{20}$)alkenyl}$_2$N—SO$_2$—, {(C$_2$-C$_{20}$)alkynyl}$_2$N—SO$_2$—, {(C$_5$-C$_{20}$)cycloalkynyl}$_2$N—SO$_2$—, {(C$_5$-C$_{25}$)aryl}$_2$N—SO$_2$—, {perhalo(C$_1$-C$_{20}$)alkyl}$_2$N—SO$_2$—, (C$_1$-C$_{20}$)alkyl-SO$_2$—NH—, phenyl-SO$_2$—NH—, (C$_3$-C$_{20}$)cycloalkyl-SO$_2$—NH—, (C$_1$-C$_{20}$)alkoxy-SO$_2$—NH—, (C$_3$-C$_{25}$)heteroaryl-SO$_2$—NH—, (C$_3$-C$_{25}$)heterocyclic-SO$_2$—NH—, (C$_2$-C$_{20}$)alkenyl-SO$_2$—NH—, (C$_3$-C$_{20}$)cycloalkenyl-SO$_2$—NH—, (C$_2$-C$_{20}$)alkynyl-SO$_2$—NH—, (C$_5$-C$_{20}$)cycloalkynyl-SO$_2$—NH—, (C$_5$-C$_{25}$)aryl-SO$_2$—NH—, perhalo(C$_1$-C$_{20}$)alkyl-SO$_2$—NH—, (C$_1$-C$_{20}$)alkyl-NH—, phenyl-NH—, (C$_3$-C$_{20}$)cycloalkyl-NH—, (C$_1$-C$_{20}$)alkoxy-NH—, (C$_3$-C$_{25}$)heteroaryl-NH—, (C$_3$-C$_{25}$)heterocyclic-NH—, (C$_2$-C$_{20}$)alkenyl-NH—, (C$_3$-C$_{20}$)cycloalkenyl-NH—, (C$_2$-C$_{20}$)alkynyl-NH—, (C$_5$-C$_{20}$)cycloalkynyl-NH—, (C$_5$-C$_{25}$)aryl-NH—, perhalo(C$_1$-C$_{20}$)alkyl-NH—, {(C$_1$-C$_{20}$)alkyl}$_2$N—, {phenyl}$_2$N—, {(C$_3$-C$_{20}$)cycloalkyl}$_2$N—, {(C$_1$-C$_{20}$)alkoxy}$_2$N—, {(C$_3$-C$_{25}$)heteroaryl}$_2$N—, {(C$_3$-C$_{25}$)heterocyclic}$_2$N—, {(C$_2$-C$_{20}$)alkenyl}$_2$N—, {(C$_3$-C$_{20}$)cycloalkenyl}$_2$N—, {(C$_2$-C$_{20}$)alkynyl}$_2$N—, {(C$_5$-C$_{20}$)cycloalkynyl}$_2$N—, {(C$_5$-C$_{25}$)aryl}$_2$N—, {perhalo(C$_1$-C$_{20}$)alkyl}$_2$N—, (C$_1$-C$_{20}$)alkyl-(C=O)—NH—, phenyl-(C=O)—NH—, (C$_3$-C$_{20}$)cycloalkyl-(C=O)—NH—, (C$_1$-C$_{20}$)alkoxy-(C=O)—NH—, (C$_3$-C$_{25}$)heteroaryl-(C=O)—NH—, (C$_3$-C$_{25}$)heterocyclic-(C=O)—NH—, (C$_2$-C$_{20}$)alkenyl-(C=O)—NH—, (C$_3$-C$_{20}$)cycloalkenyl-(C=O)—NH—, (C$_2$-C$_{20}$)alkynyl-(C=O)—NH—, (C$_5$-C$_{20}$)cycloalkynyl-(C=O)—NH—, (C$_5$-C$_{25}$)aryl-(C=O)—NH—, perhalo(C$_1$-C$_{20}$)alkyl-(C=O)—NH—, (C$_1$-C$_{20}$)alkyl-(C=O)—{((C$_1$-C$_{20}$)alkyl)N}—, phenyl-(C=O)—{((C$_1$-C$_{20}$)alkyl)N}—, (C$_3$-C$_{20}$)cycloalkyl-(C=O)—{((C$_1$-C$_{20}$)alkyl)N}—, (C$_1$-C$_{20}$)alkoxy-(C=O)—{((C$_1$-C$_{20}$)alkyl)N}—, (C$_3$-C$_{25}$)heteroaryl-(C=O)—{((C$_1$-C$_{20}$)alkyl)N}—, (C$_3$-C$_{25}$)heterocyclic-(C=O)—{((C$_1$-C$_{20}$)alkyl)N}—, (C$_2$-C$_{20}$)alkenyl-(C=O)—{((C$_1$-C$_{20}$)alkyl)N}—, (C$_3$-C$_{20}$) cycloalkenyl-(C=O)—{((C$_1$-C$_{20}$)alkyl)N}—, (C$_2$-C$_{20}$)alkynyl-(C=O)—{((C$_1$-C$_{20}$)alkyl)N}—, (C$_5$-C$_{20}$)cycloalkynyl-(C=O)—{((C$_1$-C$_{20}$)alkyl)N}—, (C$_5$-C$_{25}$)aryl-(C=O)—{((C$_1$-C$_{20}$)alkyl)N}—, perhalo(C$_1$-C$_{20}$)alkyl-(C=O)—{((C$_1$-C$_{20}$)alkyl)N}—, phenyl-(C=O)—NH—, phenyl-(C=O)—{(phenyl)N}—, (C$_1$-C$_{20}$)alkyl-(C=O)-{(phenyl)N}—, (C$_3$-C$_{20}$)cycloalkyl-(C=O)-{(phenyl)N}—, (C$_1$-C$_{20}$)alkoxy-(C=O)-{(phenyl)N}—, (C$_3$-C$_{25}$)heteroaryl-(C=O)={(phenyl)N}—, (C$_3$-C$_{25}$)heterocyclic-(C=O)-{(phenyl)N}—, (C$_2$-C$_{20}$)alkenyl-(C=O)-{(phenyl)N}—, (C$_3$-C$_{20}$)cycloalkenyl-(C=O)-{(phenyl)N}—, (C$_2$-

C$_{20}$)alkynyl-(C=O)-{(phenyl)N}—, (C$_5$-C$_{20}$)cycloalkynyl-(C=O)-{(phenyl)N}—, (C$_5$-C$_{25}$)aryl-(C=O)—{(phenyl)N}—, perhalo(C$_1$-C$_{20}$)alkyl-(C=O)-{(phenyl)N}—, H$_2$N(C=O)—, (C$_1$-C$_{20}$)alkyl-NH—(C=O)—, phenyl-NH—(C=O)—, (C$_3$-C$_{20}$)cycloalkyl-NH—(C=O)—, (C$_1$-C$_{20}$)alkoxy-NH—(C=O)—, (C$_3$-C$_{25}$)heteroaryl-NH—(C=O)—, (C$_3$-C$_{25}$)heterocyclic-NH—(C=O)—, (C$_2$-C$_{20}$)alkenyl-NH—(C=O)—, (C$_3$-C$_{20}$)cycloalkenyl-NH—(C=O)—, (C$_2$-C$_{20}$)alkynyl-NH—(C=O)—, (C$_5$-C$_{20}$)cycloalkynyl-NH—(C=O)—, (C$_5$-C$_{25}$)aryl-NH—(C=O)—, perhalo(C$_1$-C$_{20}$)alkyl-NH—(C=O)—, {C$_1$-C$_{20}$)alkyl}$_2$N—(C=O)—, {phenyl}{(C$_1$-C$_{20}$)alkyl}N—(C=O)—, {(C$_3$-C$_{20}$)cycloalkyl}{(C$_1$-C$_{20}$)alkyl}N—(C=O)—, {(C$_1$-C$_{20}$)alkoxy}{(C$_1$-C$_{20}$)alkyl}N—(C=O)—, {(C$_3$-C$_{25}$)heteroaryl}{(C$_1$-C$_{20}$)alkyl}N—(C=O)—, {(C$_3$-C$_{25}$)heterocyclic}{(C$_1$-C$_{20}$)alkyl}N—(C=O)—, {(C$_2$-C$_{20}$)alkenyl}{(C$_1$-C$_{20}$)alkyl}N—(C=O)—, {(C$_3$-C$_{20}$)cycloalkenyl}{(C$_1$-C$_{20}$)alkyl}N—(C=O)—, {(C$_2$-C$_{20}$)alkynyl}{(C$_1$-C$_{20}$)alkyl}N—(C=O)—, {(C$_5$-C$_{20}$)cycloalkynyl}{(C$_1$-C$_{20}$)alkyl)}N—(C=O)—, {(C$_5$-C$_{25}$)aryl}{(C$_1$-C$_{20}$)alkyl}N—(C=O)—, {perhalo(C$_1$-C$_{20}$)alkyl}{(C$_1$-C$_{20}$)alkyl}N—(C=O)—, {phenyl}$_2$N—(C=O)—, {(C$_3$-C$_{20}$)cycloalkyl}{phenyl}N—(C=O)—, {(C$_1$-C$_{20}$)alkoxy}{phenyl}N—(C=O)—, {(C$_3$-C$_{25}$)heteroaryl}{phenyl}N—(C=O)—, {(C$_3$-C$_{25}$)heterocyclic}{phenyl}N—(C=O)—, {(C$_2$-C$_{20}$)alkenyl}{phenyl}N—(C=O)—, {(C$_3$-C$_{20}$)cycloalkenyl}{phenyl}N—(C=O)—, {(C$_2$-C$_{20}$)alkynyl}{phenyl}N—(C=O)—, {(C$_5$-C$_{20}$)cycloalkynyl}{phenyl}N—(C=O)—, {(C$_5$-C$_{25}$)aryl}{phenyl}N—(C=O)—, {perhalo(C$_1$-C$_{20}$)alkyl}{phenyl}N—(C=O)—, HO—(C=O)—, (C$_1$-C$_{20}$)alkyl-(C=O)—, (C$_3$-C$_{25}$)heteroaryl-(C=O)—, (C$_3$-C$_{25}$)heterocyclic-(C=O)—, (C$_2$-C$_{20}$)alkenyl-(C=O)—, (C$_3$-C$_{20}$)cycloalkenyl-(C=O)—, (C$_2$-C$_{20}$)alkynyl-(C=O)—, (C$_5$-C$_{25}$)aryl-(C=O)—, perhalo(C$_1$-C$_{20}$)alkyl-(C=O), phenyl-(C=O)—, (C$_1$-C$_{20}$)alkyl-O—(C=O)—, (C$_3$-C$_{25}$)heteroaryl-O—(C=O)—, (C$_3$-C$_{25}$)heterocyclic-O—(C=O)—, (C$_2$-C$_{20}$)alkenyl-O—(C=O)—, (C$_3$-C$_{20}$)cycloalkenyl-O—(C=O)—, (C$_2$-C$_{20}$)alkynyl-O—(C=O)—, (C$_5$-C$_{25}$)aryl-O—(C=O)—, perhalo(C$_1$-C$_{20}$)alkyl-O—(C=O)—, phenyl-O—(C=O)—, (C$_1$-C$_{20}$)alkyl-(C=O)—O—, (C$_3$-C$_{25}$)heteroaryl-(C=O)—O—, (C$_3$-C$_{25}$)heterocyclic-(C=O)—O—, (C$_2$-C$_{20}$)alkenyl-(C=O)—O—, (C$_3$-C$_{20}$)cycloalkenyl-(C=O)—O—, (C$_2$-C$_{20}$)alkynyl-(C=O)—O—, (C$_5$-C$_{25}$)aryl-(C=O)—O-1 phenyl-(C=O)—O—, perhalo(C$_1$-C$_{20}$)alkyl-(C=O)—O—, and salts thereof, wherein each of the aforesaid (C$_1$-C$_{20}$)alkyl, phenyl, (C$_3$-C$_{20}$)cycloalkyl, (C$_1$-C$_{20}$)alkoxy, (C$_3$-C$_{25}$)heteroaryl, (C$_3$-C$_{25}$)heterocyclic, (C$_2$-C$_{20}$)alkenyl, (C$_3$-C$_{20}$) cycloalkenyl, (C$_2$-C$_{20}$)alkynyl, (C$_5$-C$_{20}$)cycloalkynyl, and (C$_5$-C$_{25}$) aryl groups (of the R$^1$ and R$^{1'}$ groups) may be optionally and independently substituted by one to four moieties selected from the group consisting of hydroxy, halo, bromo, chloro, iodo, fluoro, —N$_3$, —CN, —NC, —SH, —NO$_2$, —NH$_2$, (C$_1$-C$_{20}$)alkyl, phenyl, (C$_3$-C$_{20}$)cycloalkyl, (C$_1$-C$_{20}$)alkoxy, (C$_3$-C$_{25}$)heteroaryl, (C$_3$-C$_{25}$)heterocyclic, (C$_2$-C$_{20}$)alkenyl, (C$_3$-C$_{20}$)cycloalkenyl, (C$_2$-C$_{20}$)alkynyl, (C$_5$-C$_{20}$)cycloalkynyl, (C$_5$-C$_{25}$)aryl, perhalo(C$_1$-C$_{20}$)alkyl, (C$_1$-C$_{20}$)alkyl-O—, phenyl-O—, (C$_3$-C$_{20}$)cycloalkyl-O—, (C$_3$-C$_{25}$)heteroaryl-O—, (C$_3$-C$_{25}$)heterocyclic-O—, (C$_2$-C$_{20}$)alkenyl-O—, (C$_3$-C$_{20}$)cycloalkenyl-O—, (C$_2$-C$_{20}$)alkynyl-O—, (C$_5$-C$_{20}$)cycloalkynyl-O—, (C$_5$-C$_{25}$)aryl-O—, perhalo(C$_1$-C$_{20}$)alkyl-O—, (C$_1$-C$_{20}$)alkyl-S—, phenyl-S—, (C$_3$-C$_{20}$)cycloalkyl-S—, (C$_3$-C$_{25}$)heteroaryl-S—, (C$_3$-C$_{25}$)heterocyclic-S—, (C$_2$-C$_{20}$)alkenyl-S—, (C$_3$-C$_{20}$)cycloalkenyl-S—, (C$_2$-C$_{20}$)alkynyl-S—, (C$_5$-C$_{20}$)cycloalkynyl-S—, (C$_5$-C$_{25}$)aryl-S—, perhalo(C$_1$-C$_{20}$)alkyl-S—, (C$_1$-C$_{20}$)alkyl-SO$_2$—, phenyl-SO$_2$—, (C$_3$-C$_{20}$)cycloalkyl-SO$_2$—, (C$_1$-C$_{20}$)alkoxy-SO$_2$—, (C$_3$-C$_{25}$)heteroaryl-SO$_2$—, (C$_3$-C$_{25}$)heterocyclic-SO$_2$—, (C$_2$-C$_{20}$)alkenyl-SO$_2$—, (C$_3$-C$_{20}$)cycloalkenyl-SO$_2$—, (C$_2$-C$_{20}$)alkynyl-SO$_2$—, (C$_5$-C$_{20}$)cycloalkynyl-SO$_2$—, (C$_5$-C$_{25}$)aryl-SO$_2$—, perhalo(C$_1$-C$_{20}$)alkyl-SO$_2$—, H$_2$N—SO$_2$—, (C$_1$-C$_{20}$)alkyl-NH—SO$_2$—, phenyl-NH—SO$_2$—, (C$_3$-C$_{20}$)cycloalkyl-NH—SO$_2$—, (C$_1$-C$_{20}$)alkoxy-NH—SO$_2$—, (C$_3$-C$_{25}$)heteroaryl-NH—SO$_2$—, (C$_3$-C$_{25}$)heterocyclic-NH—SO$_2$—, (C$_2$-C$_{20}$)alkenyl-NH—SO$_2$—, (C$_3$-C$_{20}$)cycloalkenyl-NH—SO$_2$—, (C$_2$-C$_{20}$)alkynyl-NH—SO$_2$—, (C$_5$-C$_{20}$)cycloalkynyl-NH—SO$_2$—, (C$_5$-C$_{25}$)aryl-NH—SO$_2$—, perhalo(C$_1$-C$_{20}$)alkyl-NH—SO$_2$—, {(C$_1$-C$_{20}$)alkyl}$_2$N—SO$_2$—, {phenyl}$_2$N—SO$_2$—, {(C$_3$-C$_{20}$)cycloalkyl}$_2$N—SO$_2$—, {(C$_1$-C$_{20}$)alkoxy}$_2$N—SO$_2$—, {(C$_3$-C$_{25}$)heteroaryl}$_2$N—SO$_2$—, {(C$_3$-C$_{25}$)heterocyclic}$_2$N—SO$_2$—, {(C$_2$-C$_{20}$)alkenyl}$_2$N—SO$_2$—, {(C$_2$-C$_{20}$)alkynyl}$_2$N—SO$_2$—, {(C$_5$-C$_{20}$)cycloalkynyl}$_2$N—SO$_2$—, {(C$_5$-C$_{25}$)aryl}$_2$N—SO$_2$—, {perhalo(C$_1$-C$_{20}$)alkyl}$_2$N—SO$_2$—, (C$_1$-C$_{20}$)alkyl-SO$_2$—NH—, phenyl-SO$_2$—NH—, (C$_3$-C$_{20}$)cycloalkyl-SO$_2$—NH—, (C$_1$-C$_{20}$)alkoxy-SO$_2$—NH—, (C$_3$-C$_{25}$)heteroaryl-SO$_2$—NH—, (C$_3$-C$_{25}$)heterocyclic-SO$_2$—NH—, (C$_2$-C$_{20}$)alkenyl-SO$_2$—NH—, (C$_3$-C$_{20}$)cycloalkenyl-SO$_2$—NH—, (C$_2$-C$_{20}$)alkynyl-SO$_2$—NH—, (C$_5$-C$_{20}$)cycloalkynyl-SO$_2$—NH—, (C$_5$-C$_{25}$)aryl-SO$_2$—NH—, perhalo(C$_1$-C$_{20}$)alkyl-SO$_2$—NH—, (C$_1$-C$_{20}$)alkyl-NH—, phenyl-NH—, (C$_3$-C$_{20}$)cycloalkyl-NH—, (C$_1$-C$_{20}$)alkoxy-NH—, (C$_3$-C$_{25}$)heteroaryl-NH—, (C$_3$-C$_{25}$)heterocyclic-NH—, (C$_2$-C$_{20}$)alkenyl-NH—, (C$_3$-C$_{20}$)cycloalkenyl-NH—, (C$_2$-C$_{20}$)alkynyl-NH—, (C$_5$-C$_{20}$)cycloalkynyl-NH—, (C$_5$-C$_{25}$)aryl-NH—, perhalo(C$_1$-C$_{20}$)alkyl-NH—, {(C$_1$-C$_{20}$)alkyl}$_2$N—, {phenyl}$_2$N—, {(C$_3$-C$_{20}$)cycloalkyl}$_2$N—, {(C$_1$-C$_{20}$)alkoxy}$_2$N—, {(C$_3$-C$_{25}$)heteroaryl}$_2$N—, {(C$_3$-C$_{25}$)heterocyclic}$_2$N—, {(C$_2$-C$_{20}$)alkenyl}$_2$N—, {(C$_3$-C$_{20}$)cycloalkenyl}$_2$N—, {(C$_2$-C$_{20}$)alkynyl}$_2$N—, {(C$_5$-C$_{20}$)cycloalkynyl}$_2$N—, {(C$_5$-C$_{25}$)aryl}$_2$N—, {perhalo(C$_1$-C$_{20}$)alkyl}$_2$N—, (C$_1$-C$_{20}$)alkyl-(C=O)—NH—, phenyl-(C=O)—NH—, (C$_3$-C$_{20}$)cycloalkyl-(C=O)—NH—, (C$_1$-C$_{20}$)alkoxy-(C=O)—NH—, (C$_3$-C$_{25}$)heteroaryl-(C=O)—NH—, (C$_3$-C$_{25}$)heterocyclic-(C=O)—NH—, (C$_2$-C$_{20}$)alkenyl-(C=O)—NH—, (C$_3$-C$_{20}$)cycloalkenyl-(C=O)—NH—, (C$_2$-C$_{20}$)alkynyl-(C=O)—NH—, (C$_5$-C$_{20}$)cycloalkynyl-(C=O)—NH—, (C$_5$-C$_{25}$)aryl-(C=O)—NH—, perhalo(C$_1$-C$_{20}$)alkyl-(C=O)—NH—, (C$_1$-C$_{20}$)alkyl-(C=O)—{((C$_1$-C$_{20}$)alkyl)N}—, phenyl-(C=O)—{((C$_1$-C$_{20}$)alkyl)N}—, (C$_3$-C$_{20}$)cycloalkyl-(C=O)—{((C$_1$-C$_{20}$)alkyl)N}—, (C$_1$-C$_{20}$)alkoxy-(C=O)—{((C$_1$-C$_{20}$)alkyl)N}—, (C$_3$-C$_{25}$)heteroaryl-(C=O)—{((C$_1$-C$_{20}$)alkyl)N}—, (C$_3$-C$_{25}$)heterocyclic-(C=O)—{((C$_1$-C$_{20}$)alkyl)N}—, (C$_2$-C$_{20}$)alkenyl-(C=O)—{((C$_1$-C$_{20}$)alkyl)N}—, (C$_3$-C$_{20}$) cycloalkenyl-(C=O)—{((C$_1$-C$_{20}$)alkyl)N}—, (C$_2$-C$_{20}$)alkynyl-(C=O)—{((C$_1$-C$_{20}$)alkyl)N}—, (C$_5$-C$_{20}$)cycloalkynyl-(C=O)—{((C$_1$-C$_{20}$)alkyl)N}—, (C$_5$-C$_{25}$)aryl-(C=O)—{((C$_1$-C$_{20}$)alkyl)N}—, perhalo(C$_1$-C$_{20}$)alkyl-(C=O)—{((C$_1$-C$_{20}$)alkyl)N}—, phenyl-(C=O)—NH—, phenyl-(C=O)-{(phenyl)N}—, (C$_1$-C$_{20}$)alkyl-(C=O)-{(phenyl)N}—, (C$_3$-C$_{20}$)cycloalkyl-(C=O)-{(phenyl)N}—, (C$_1$-C$_{20}$)alkoxy-(C=O)-{(phenyl)N}—, (C$_3$-C$_{25}$)heteroaryl-(C=O)-{(phenyl)N}—, (C$_3$-C$_{25}$)heterocyclic-(C=O)-{(phenyl)N}—, (C$_2$-C$_{20}$)alkenyl-(C=O)-{(phenyl)N}—, (C$_3$-C$_{20}$)cycloalkenyl-(C=O)-{(phenyl)N}—, (C$_2$-C$_{20}$)alkynyl-(C=O)-{(phenyl)N}—, (C$_5$-C$_{20}$)cycloalkynyl-(C=O)-{(phenyl)N}—, (C$_5$-C$_{25}$)aryl-(C=O)-{(phenyl)N}—, perhalo(C$_1$-C$_{20}$)alkyl- (C=O)-{(phenyl)N}—, $H_2N(C=O)$—, $(C_1-C_{20})$alkyl-NH—(C=O)—, phenyl-NH—(C=O)—, $(C_3-C_{20})$cycloalkyl-NH—(C=O)—, $(C_1-C_{20})$alkoxy-NH—(C=O)—, $(C_3-C_{25})$heteroaryl-NH—(C=O)—, $(C_3-C_{25})$heterocyclic-NH—(C=O)—, $(C_2-C_{20})$alkenyl-NH—(C=O)—, $(C_3-C_{20})$cycloalkenyl-NH—(C=O)—, $(C_2-C_{20})$alkynyl-NH—(C=O)—, $(C_5-C_{20})$cycloalkynyl-NH—(C=O)—, $(C_5-C_{25})$aryl-NH—(C=O)—, perhalo$(C_1-C_{20})$alkyl-NH—(C=O)—, $\{C_1-C_{20})$alkyl$\}_2N$—(C=O)—, {phenyl}{$(C_1-C_{20})$alkyl}N—(C=O)—, {$(C_3-C_{20})$cycloalkyl}{$(C_1-C_{20})$alkyl}N—(C=O)—, {$(C_1-C_{20})$alkoxy}{$(C_1-C_{20})$alkyl}N—(C=O)—, {$(C_3-C_{25})$heteroaryl}{$(C_1-C_{20})$alkyl}N—(C=O)—, {$(C_3-C_{25})$heterocyclic}{$(C_1-C_{20})$alkyl}N—(C=O)—, {$(C_2-C_{20})$alkenyl}{$(C_1-C_{20})$alkyl}N—(C=O), {$(C_3-C_{20})$cycloalkenyl}{$(C_1-C_{20})$alkyl}N—(C=O)—, {$(C_2-C_{20})$alkynyl}{$(C_1-C_{20})$alkyl}N—(C=O)—, {$(C_5-C_{20})$cycloalkynyl}{$(C_1-C_{20})$alkyl}N—(C=O)—, {$(C_5-C_{25})$aryl}{$(C_1-C_{20})$alkyl}N—(C=O)—, {perhalo$(C_1-C_{20})$alkyl}{$(C_1-C_{20})$alkyl}N—(C=O)—, {phenyl}$_2$N—(C=O)—, {$(C_3-C_{20})$cycloalkyl}{phenyl}N—(C=O)—, {$(C_1-C_{20})$alkoxy}{phenyl}N—(C=O)—, {$(C_3-C_{25})$heteroaryl}{phenyl}N—(C=O)—, {$(C_3-C_{25})$heterocyclic}{phenyl}N—(C=O)—, {$(C_2-C_{20})$alkenyl}{phenyl}N—(C=O)—, {$(C_3-C_{20})$cycloalkenyl}{phenyl}N—(C=O)—, {$(C_2-C_{20})$alkynyl}{phenyl}N—(C=O)—, {$(C_5-C_{20})$cycloalkynyl}{phenyl}N—(C=O)—, {$(C_5-C_{25})$aryl}{phenyl}N—(C=O)—, {perhalo$(C_1-C_{20})$alkyl}{phenyl}N—(C=O)—, HO—(C=O)—, $(C_1-C_{20})$alkyl-(C=O)—, $(C_3-C_{25})$heteroaryl-(C=O)—, $(C_3-C_{25})$heterocyclic-(C=O)—, $(C_2-C_{20})$alkenyl-(C=O)—, $(C_3-C_{20})$cycloalkenyl-(C=O)—, $(C_2-C_{20})$alkynyl-(C=O)—, $(C_5-C_{25})$aryl-(C=O)—, perhalo$(C_1-C_{20})$alkyl-(C=O)—, phenyl-(C=O)—, $(C_1-C_{20})$alkyl-O—(C=O)—, $(C_3-C_{25})$heteroaryl-O—(C=O)—, $(C_3-C_{25})$heterocyclic-O—(C=O)—, $(C_2-C_{20})$alkenyl-O—(C=O)—, $(C_3-C_{20})$cycloalkenyl-O—(C=O)—, $(C_2-C_{20})$alkynyl-O—(C=O)—, $(C_5-C_{25})$aryl-O—(C=O)—, perhalo$(C_1-C_{20})$alkyl-O—(C=O)—, phenyl-O—(C=O)—, $(C_1-C_{20})$alkyl-(C=O)—O—, $(C_3-C_{25})$heteroaryl-(C=O)—O—, $(C_3-C_{25})$heterocyclic-(C=O)—O—, $(C_2-C_{20})$alkenyl-(C=O)—O—, $(C_3-C_{20})$cycloalkenyl-(C=O)—O—, $(C_2-C_{20})$alkynyl-(C=O)—O—, $(C_5-C_{25})$aryl-(C=O)—O—, phenyl-(C=O)—O—, perhalo$(C_1-C_{20})$alkyl-(C=O)—O—, and salts thereof;

and wherein two independently chosen $R^1$ or $R^{1'}$ alkyl-containing groups may be taken together with any atom to which they are attached to form a three to forty membered cyclic, heterocyclic or heteroaryl ring.

In another embodiment, Z has the formula:

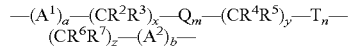

wherein Q and T are each independently selected from the group consisting $R^{10}(CO)NR^{11}$—, —$(CO)NR^{10}$—, —$NR^{10}$(CO)—, —$NR^{10}$—, salts thereof, —O—, optionally substituted alkylene, optionally substituted arylene, optionally substituted heteroarylene, and combinations thereof;

wherein $A^1$, $R^2$, $R^3$, $R^4$, $R^5$, $R^6$, $R^7$, $A^2$, $R^{10}$, and $R^{11}$ are defined herein;

wherein if substituted, the alkylene, arylene, and heteroarylene, are each independently substituted with 0 to 4 groups selected from the group consisting of H, halogen, OR, $NR^1R^{1'}$, $NR^1CO$, $CONR^1$, $COR^1$, $SR^1$, $SO_2R^1$, $SO_2NR^1$, $SOR^1$, alkyl, aryl, heteroalkyl, and heteroaryl, salts thereof, and combinations thereof;

and wherein $R^1$ and $R^{1'}$ being each independently selected from the group including alkyl, aryl, heteroalkyl, and heteroaryl.

In one embodiment, said alkylene, cycloalkylene or arylene in said Q and/or T are each independently substituted with one or more substituent groups selected from the group consisting of hydroxy, halo, bromo, chloro, iodo, fluoro, —$N_3$, —CN, —NC, —SH, —$NO_2$, —$NH_2$, salts thereof, and combinations thereof.

In another embodiment, said alkylene, cycloalkylene or arylene in said Q and/or T are each independently substituted with one or more substituent groups selected from the group consisting of $(C_1-C_{20})$alkyl, phenyl, $(C_3-C_{20})$cycloalkyl, $(C_1-C_{20})$alkoxy, $(C_3-C_{25})$heteroaryl, $(C_3-C_{25})$heterocyclic, $(C_2-C_{20})$alkenyl, $(C_3-C_{20})$cycloalkenyl, $(C_2-C_{20})$alkynyl, $(C_5-C_{20})$cycloalkynyl, $(C_5-C_{25})$aryl, perhalo$(C_1-C_{20})$alkyl, and a combination thereof.

In another embodiment, said alkylene, cycloalkylene or arylene in said Q and/or T are each independently substituted with one or more substituent groups selected from the group consisting of $(C_1-C_{20})$alkyl-O—, phenyl-O—, $(C_3-C_{20})$cycloalkyl-O—, $(C_3-C_{25})$heteroaryl-O—, $(C_3-C_{25})$heterocyclic-O—, $(C_2-C_{20})$alkenyl-O—, $(C_3-C_{20})$cycloalkenyl-O—, $(C_2-C_{20})$alkynyl-O—, $(C_5-C_{20})$cycloalkynyl-O—, $(C_5-C_{25})$aryl-O—, perhalo$(C_1-C_{20})$alkyl-O—, and a combination thereof.

In another embodiment, said alkylene, cycloalkylene or arylene in said Q and/or T are each independently substituted with one or more substituent groups selected from the group consisting of $(C_1-C_{20})$alkyl-S—, phenyl-S—, $(C_3-C_{20})$cycloalkyl-S—, $(C_3-C_{25})$heteroaryl-S—, $(C_3-C_{25})$heterocyclic-S—, $(C_2-C_{20})$alkenyl-S—, $(C_3-C_{20})$cycloalkenyl-S—, $(C_2-C_{20})$alkynyl-S—, $(C_5-C_{20})$cycloalkynyl-S—, $(C_5-C_{25})$aryl-S—, perhalo$(C_1-C_{20})$alkyl-S—, and a combination thereof.

In another embodiment, said alkylene, cycloalkylene or arylene in said Q and/or T are each independently substituted with one or more substituent groups selected from the group consisting of $(C_1-C_{20})$alkyl-$SO_2$—, phenyl-$SO_2$—, $(C_3-C_{20})$cycloalkyl-$SO_2$—, $(C_1-C_{20})$alkoxy-$SO_2$—, $(C_3-C_{25})$heteroaryl-$SO_2$—, $(C_3-C_{25})$heterocyclic-$SO_2$—, $(C_2-C_{20})$alkenyl-$SO_2$—, $(C_3-C_{20})$cycloalkenyl-$SO_2$—, $(C_2-C_{20})$alkynyl-$SO_2$—, $(C_5-C_{20})$cycloalkynyl-$SO_2$—, $(C_5-C_{25})$aryl-$SO_2$—, perhalo$(C_1-C_{20})$alkyl-$SO_2$—, and a combination thereof.

In another embodiment, said alkylene, cycloalkylene or arylene in said Q and/or T are each independently substituted with one or more substituent groups selected from the group consisting of $H_2N$—$SO_2$—, $(C_1-C_{20})$alkyl-NH—$SO_2$—, phenyl-NH—$SO_2$—, $(C_3-C_{20})$cycloalkyl-NH—$SO_2$—, $(C_1-C_{20})$alkoxy-NH—$SO_2$—, $(C_3-C_{25})$heteroaryl-NH—$SO_2$—, $(C_3-C_{25})$heterocyclic-NH—$SO_2$—, $(C_2-C_{20})$alkenyl-NH—$SO_2$—, $(C_3-C_{20})$cycloalkenyl-NH—$SO_2$—, $(C_2-C_{20})$alkynyl-NH—$SO_2$—, $(C_5-C_{20})$cycloalkynyl-NH—$SO_2$—, $(C_5-C_{25})$aryl-NH—$SO_2$—, perhalo$(C_1-C_{20})$alkyl-NH—$SO_2$—, salts thereof, and a combination thereof.

In another embodiment, said alkylene, cycloalkylene or arylene in said Q and/or T are each independently substituted with one or more substituent groups selected from the group consisting of {$(C_1-C_{20})$alkyl}$_2$N—$SO_2$—, {phenyl}$_2$N—$SO_2$—, {$(C_3-C_{20})$cycloalkyl}$_2$N—$SO_2$—, {$(C_1-C_{20})$alkoxy}$_2$N—$SO_2$—, {$(C_3-C_{25})$heteroaryl}$_2$N—$SO_2$—, {$(C_3-C_{25})$heterocyclic}$_2$N—$SO_2$—, {$(C_2-C_{20})$alkenyl}$_2$N—$SO_2$—, {$(C_2-C_{20})$alkynyl}$_2$N—$SO_2$—, {$(C_5-C_{20})$cycloalkynyl}$_2$N—$SO_2$—, {$(C_5-C_{25})$aryl}$_2$N—$SO_2$—, {perhalo$(C_1-C_{20})$alkyl}$_2$N—$SO_2$—, salts thereof, and a combination thereof.

In another embodiment, said alkylene, cycloalkylene or arylene in said Q and/or T are each independently substituted with one or more substituent groups selected from the group consisting of $(C_1-C_{20})$alkyl-$SO_2$—NH—, phenyl-$SO_2$—NH—, $(C_3-C_{20})$cycloalkyl-$SO_2$—NH—, $(C_1-C_{20})$alkoxy-$SO_2$—NH—, $(C_3-C_{25})$heteroaryl-$SO_2$—NH—, $(C_3-C_{25})$heterocyclic-$SO_2$—NH—, $(C_2-C_{20})$alkenyl-$SO_2$—NH—, $(C_3-C_{20})$cycloalkenyl-$SO_2$—NH—, $(C_2-C_2)$alkynyl-$SO_2$—NH—, $(C_5-C_{20})$cycloalkynyl-$SO_2$—NH—, $(C_5-C_{25})$aryl-$SO_2$—NH—, perhalo$(C_1-C_{20})$alkyl-$SO_2$—NH—, salts thereof, and a combination thereof.

In another embodiment, said alkylene, cycloalkylene or arylene in said Q and/or T are each independently substituted with one or more substituent groups selected from the group consisting of $(C_1-C_{20})$alkyl-NH—, phenyl-NH—, $(C_3-C_{20})$cycloalkyl-NH—, $(C_1-C_{20})$alkoxy-NH—, $(C_3-C_{25})$heteroaryl-NH—, $(C_3-C_{25})$heterocyclic-NH—, $(C_2-C_{20})$alkenyl-NH—, $(C_3-C_{20})$cycloalkenyl-NH—, $(C_2-C_{20})$alkynyl-NH—, $(C_5-C_{20})$cycloalkynyl-NH—, $(C_5-C_{25})$aryl-NH—, perhalo$(C_1-C_{20})$alkyl-NH—, salts thereof, and a combination thereof.

In another embodiment, said alkylene, cycloalkylene or arylene in said Q and/or T are each independently substituted with one or more substituent groups selected from the group consisting of $\{(C_1-C_{20})$alkyl$\}_2$N—, $\{$phenyl$\}_2$N—, $\{(C_3-C_{20})$cycloalkyl$\}_2$N—, $\{(C_1-C_{20})$alkoxy$\}_2$N—, $\{(C_3-C_{25})$heteroaryl$\}_2$N—, $\{(C_3-C_{25})$heterocyclic$\}_2$N—, $\{(C_2-C_{20})$alkenyl$\}_2$N—, $\{(C_3-C_{20})$cycloalkenyl$\}_2$N—, $\{(C_2-C_{20})$alkynyl$\}_2$N—, $\{(C_5-C_{20})$cycloalkynyl$\}_2$N—, $\{(C_5-C_{25})$aryl$\}_2$N—, $\{$perhalo$(C_1-C_{20})$alkyl$\}_2$N—, salts thereof, and a combination thereof.

In another embodiment, said alkylene, cycloalkylene or arylene in said Q and/or T are each independently substituted with one or more substituent groups selected from the group consisting of $(C_1-C_{20})$alkyl-(C=O)—NH—, phenyl-(C=O)—NH—, $(C_3-C_{20})$cycloalkyl-(C=O)—NH—, $(C_1-C_{20})$alkoxy-(C=O)—NH—, $(C_3-C_{25})$heteroaryl-(C=O)—NH—, $(C_3-C_{25})$heterocyclic-(C=O)—NH—, $(C_2-C_{20})$alkenyl-(C=O)—NH—, $(C_3-C_{20})$cycloalkenyl-(C=O)—NH—, $(C_2-C_{20})$alkynyl-(C=O)—NH—, $(C_5-C_{20})$cycloalkynyl-(C=O)—NH—, $(C_5-C_{25})$aryl-(C=O)—NH—, perhalo$(C_1-C_{20})$alkyl-(C=O)—NH—, salts thereof, and a combination thereof.

In another embodiment, said alkylene, cycloalkylene or arylene in said Q and/or T are each independently substituted with one or more substituent groups selected from the group consisting of $(C_1-C_{20})$alkyl-(C=O)—$\{((C_1-C_{20})$alkyl)N$\}$—, phenyl-(C=O)—$\{((C_1-C_{20})$alkyl)N$\}$—, $(C_3-C_{20})$cycloalkyl-(C=O)—$\{((C_1-C_{20})$alkyl)N$\}$—, $(C_1-C_{20})$alkoxy-(C=O)—$\{((C_1-C_{20})$alkyl)N$\}$—, $(C_3-C_{25})$heteroaryl-(C=O)—$\{((C_1-C_{20})$alkyl)N$\}$, $(C_3-C_{25})$heterocyclic-(C=O)—$\{((C_1-C_{20})$alkyl)N$\}$—, $(C_2-C_{20})$alkenyl-(C=O)—$\{((C_1-C_{20})$alkyl)N$\}$—, $(C_3-C_{20})$cycloalkenyl-(C=O)—$\{((C_1-C_{20})$alkyl)N$\}$—, $(C_2-C_{20})$alkynyl-(C=O)—$\{((C_1-C_{20})$alkyl)N$\}$—, $(C_5-C_{20})$cycloalkyl-(C=O)—$\{((C_1-C_{20})$alkyl)N$\}$—, $(C_5-C_{25})$aryl-(C=O)—$\{((C_1-C_{20})$alkyl)N$\}$—, perhalo$(C_1-C_{20})$alkyl-(C=O)—$\{((C_1-C_{20})$alkyl)N$\}$—, salts thereof, and a combination thereof.

In another embodiment, said alkylene, cycloalkylene or arylene in said Q and/or T are each independently substituted with one or more substituent groups selected from the group consisting of phenyl-(C=O)—NH—, phenyl-(C=O)-$\{$(phenyl)N$\}$—, $(C_1-C_{20})$alkyl-(C=O)-$\{$(phenyl)N$\}$—, $(C_3-C_{20})$cycloalkyl-(C=O)-$\{$(phenyl)N$\}$—, $(C_1-C_{20})$alkoxy-(C=O)-$\{$(phenyl)N$\}$—, $(C_3-C_{25})$heteroaryl-(C=O)-$\{$(phenyl)N$\}$—, $(C_3-C_{25})$heterocyclic-(C=O)-$\{$(phenyl)N$\}$—, $(C_2-C_{20})$alkenyl-(C=O)-$\{$(phenyl)N$\}$—, $(C_3-C_{20})$cycloalkenyl-(C=O)-$\{$(phenyl)N$\}$—, $(C_2-C_{20})$alkynyl-(C=O)-$\{$(phenyl)N$\}$—, $(C_5-C_{20})$cycloalkynyl-(C=O)-$\{$(phenyl)N$\}$—, $(C_5-C_{25})$aryl-(C=O)-$\{$(phenyl)N$\}$—, perhalo$(C_1-C_{20})$alkyl-(C=O)-$\{$(phenyl)N$\}$—, salts thereof, and a combination thereof.

In another embodiment, said alkylene, cycloalkylene or arylene in said Q and/or T are each independently substituted with one or more substituent groups selected from the group consisting of $H_2N$(C=O)—, $(C_1-C_{20})$alkyl-NH—(C=O)—, phenyl-NH—(C=O)—, $(C_3-C_{20})$cycloalkyl-NH—(C=O)—, $(C_1-C_{20})$alkoxy-NH—(C=O)—, $(C_3-C_{25})$heteroaryl-NH—(C=O)—, $(C_3-C_{25})$heterocyclic-NH—(C=O), $(C_2-C_{20})$alkenyl-NH—(C=O)—, $(C_3-C_{20})$cycloalkenyl-NH—(C=O)—, $(C_2-C_{20})$alkynyl-NH—(C=O)—, $(C_5-C_{20})$cycloalkynyl-NH—(C=O)—, $(C_5-C_{25})$aryl-NH—(C=O), perhalo$(C_1-C_{20})$alkyl-NH—(C=O)—, salts thereof, and a combination thereof.

In another embodiment, said alkylene, cycloalkylene or arylene in said Q and/or T are each independently substituted with one or more substituent groups selected from the group consisting of $\{C_1-C_{20}$alkyl$\}_2$N—(C=O)—, $\{$phenyl$\}\{(C_1-C_{20})$alkyl$\}$N—(C=O)—, $\{(C_3-C_{20})$cycloalkyl$\}\{(C_1-C_{20})$alkyl$\}$N—(C=O)—, $\{(C_1-C_{20})$alkoxy$\}\{(C_1-C_{20})$alkyl$\}$N—(C=O)—, $\{(C_3-C_{25})$heteroaryl$\}\{(C_1-C_{20})$alkyl$\}$N—(C=O)—, $\{(C_3-C_{25})$heterocyclic$\}\{(C_1-C_{20})$alkyl$\}$N—(C=O)—, $\{(C_2-C_{20})$alkenyl$\}\{(C_1-C_{20})$alkyl$\}$N—(C=O)—, $\{(C_3-C_{20})$cycloalkenyl$\}\{(C_1-C_{20})$alkyl$\}$N—(C=O)—, $\{(C_2-C_{20})$alkynyl$\}\{(C_1-C_{20})$alkyl$\}$N—(C=O), $\{(C_5-C_{20})$cycloalkynyl$\}\{(C_1-C_{20})$alkyl$\}$N—(C=O)—, $\{(C_5-C_{25})$aryl$\}\{(C_1-C_{20})$alkyl$\}$N—(C=O)—, $\{$perhalo$(C_1-C_{20})$alkyl$\}\{(C_1-C_{20})$alkyl$\}$N—(C=O)—, salts thereof, and a combination thereof.

In another embodiment, said alkylene, cycloalkylene or arylene in said Q and/or T are each independently substituted with one or more substituent groups selected from the group consisting of $\{$phenyl$\}_2$N—(C=O)—, $\{(C_3-C_{20})$cycloalkyl$\}\{$phenyl$\}$N—(C=O)—, $\{(C_1-C_{20})$alkoxy$\}\{$phenyl$\}$N—(C=O)—, $\{(C_3-C_{25})$heteroaryl$\}\{$phenyl$\}$N—(C=O)—, $\{(C_3-C_{25})$heterocyclic$\}\{$phenyl$\}$N—(C=O)—, $\{(C_2-C_{20})$alkenyl$\}\{$phenyl$\}$N—(C=O)—, $\{(C_3-C_{20})$cycloalkenyl$\}\{$phenyl$\}$N—(C=O)—, $\{(C_2-C_{20})$alkynyl$\}\{$phenyl$\}$N—(C=O)—, $\{(C_5-C_{20})$cycloalkynyl$\}\{$phenyl$\}$N—(C=O)—, $\{(C_1-C_{25})$aryl$\}\{$phenyl$\}$N—(C=O)—, $\{$perhalo$(C_1-C_{20})$alkyl$\}\{$phenyl$\}$N—(C=O)—, salts thereof, and a combination thereof.

In another embodiment, said alkylene, cycloalkylene or arylene in said Q and/or T are each independently substituted with one or more substituent groups selected from the group consisting of HO—(C=O)—, $(C_1-C_{20})$alkyl-(C=O)—, $(C_3-C_{25})$heteroaryl-(C=O)—, $(C_3-C_{25})$heterocyclic-(C=O), $(C_2-C_{20})$alkenyl-(C=O)—, $(C_3-C_{20})$cycloalkenyl-(C=O)—, $(C_2-C_{20})$alkynyl-(C=O)—, $(C_1-C_{25})$aryl-(C=O)—, perhalo$(C_1-C_{20})$alkyl-(C=O)—, phenyl-(C=O)—, and a combination thereof.

In another embodiment, said alkylene, cycloalkylene or arylene in said Q and/or T are each independently substituted with one or more substituent groups selected from the group consisting of $(C_1-C_{20})$alkyl-O—(C=O)—, $(C_3-C_{25})$heteroaryl-O—(C=O)—, $(C_3-C_{25})$heterocyclic-O—(C=O)—, $(C_2-C_{20})$alkenyl-O—(C=O)—, $(C_3-C_{20})$cycloalkenyl-O—(C=O)—, $(C_2-C_{20})$alkynyl-O—(C=O)—, $(C_5-C_{25})$aryl-O—(C=O)—, perhalo$(C_1-C_{20})$alkyl-O—(C=O)—, phenyl-O—(C=O)—, and a combination thereof.

In another embodiment, said alkylene, cycloalkylene or arylene in said Q and/or T are each independently substituted with one or more substituent groups selected from the group consisting of $(C_1-C_{20})$alkyl-(C=O)—O—, $(C_3-C_{25})$heteroaryl-(C=O)—O—, $(C_3-C_{25})$heterocyclic-(C=O)—O—, $(C_2-C_{20})$alkenyl-(C=O)—O—, $(C_3-C_{20})$cycloalkenyl-(C=O)—O—, $(C_2-C_{20})$alkynyl-(C=O)—O—, $(C_5-C_{25})$aryl-(C=O)—O—, phenyl-(C=O)—O—, perhalo($C_1$-$C_{20}$)alkyl-(C=O)—O—, and a combination thereof.

When the Z group or any of its constituent A, Q, T, or CRR groups are substituted, the substituent is preferably a pharmaceutically acceptable or suitable substituent. This type of substituent is intended to mean a chemically and pharmaceutically acceptable functional group (e.g., a moiety that does not negate the pharmaceutical activity of the active compound.)

In one embodiment, the suitable pharmaceutically acceptable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C=O)— groups, amino groups, alkyl- and dialkylamino groups, carbamoyl groups, alkylcarbonyl groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups and the like.

As used herein, the term, "alkylene" refers to a diradical alkane species that contains 1, 2, 3, 4, 5, 6, 7, 8, 9, 10, 11, 12, 13, 14, 15, 16, 17, 18, 19 and 20 carbons or any subrange of carbons therebetween. The alkylene may be branched or unbranched, saturated or unsaturated, and substituted or unsubstituted. In addition, any carbon atom therein may be optionally replaced with one or more heteroatoms such as nitrogen, oxygen or sulfur or any combination thereof.

As used herein, the term, "cycloalkylene" refers to a diradical cycloalkane species that contains 3, 4, 5, 6, 7, 8, 9, 10, 11, 12, 13, 14, 15, 16, 17, 18, 19 and 20 ring carbons or any subrange of carbons therebetween. The cycloalkylene may be branched or unbranched, saturated or unsaturated, and substituted or unsubstituted. In addition, any carbon atom therein may be optionally replaced with one or more heteroatom such as nitrogen, oxygen or sulfur or any combination thereof.

As used herein, the term "arylene" means an aromatic diradical species having 5, 6, 7, 8, 9, 10, 11, 12, 13, 14, 15, 16, 17, 18, 19, 20, 21, 22, 23, 24 and 25 carbons and any subrange of carbons thereof. These may be unsubstitued or substituted as indicated herein. In addition, any carbon atom therein may be optionally replaced with one or more heteroatom such as nitrogen, oxygen or sulfur or any combination thereof to form a heteroarylene.

As used herein, the term "alkyl" as well as the alkyl moieties of or within other groups referred to herein (e.g., $(C_1-C_{20})$alkyl, $(C_1-C_{20})$alkoxy, $(C_2-C_{20})$alkenyl, $(C_2-C_{20})$alkynyl, and perhalo($C_1-C_{20}$)alkyl) include alkyl moieties having 1, 2, 3, 4, 5, 6, 7, 8, 9, 10, 11, 12, 13, 14, 15, 16, 17, 18, 19 and 20 carbons or any subrange of carbons therebetween. They may be linear or branched (such as methyl, ethyl, n-propyl, isopropyl, n-butyl, iso-butyl, secondary-butyl, tertiary-butyl, etc.). They may be saturated or unsaturated as indicated by the "alkenyl" or "alkynyl" terminology. Other than the perhaloalkyl, which are completely substituted by one or more of the same or different halogens, the alkyl groups may be unsubstituted or substitued as indicated herein.

As used herein, the term "cycloalkyl" as well as the other moieties having cyclic groups referred to herein (for example $(C_3-C_{20})$cycloalkyl, $(C_3-C_{20})$ cycloalkenyl and $(C_5-C_{20})$cycloalkynyl) refers to mono carbocyclic moieties having 3, 4, 5, 6, 7, 8, 9, 10, 11, 12, 13, 14, 15, 16, 17, 18, 19 and 20 ring carbons or any subrange of carbons therebetween. They may be unsubstituted or substituted as indicated herein.

As used herein, the terms, "alkenyl," "alkynyl," "cycloalkynyl," and "cycloalkenyl" refer to unsaturated radical species having 1, 2, 3, 4, 5, 6, 7, 8, 9, 10, 11, 12, 13, 14, 15, 16, 17, 18, 19 and 20 carbons (or, for the cyclic species 3, 4, 5, 6, 7, 8, 9, 10, 11, 12, 13, 14, 15, 16, 17, 18, 19 and 20 ring carbons) or any subrange of carbons or ring carbons therebetween. They may be branched or unbranched, and they may be unsubstituted or substituted as indicated herein. These groups have one or more than one site of unsaturation, i.e., one or more double or triple bonds. For example, these moieties may have one, two, three, four or more sites of unsaturation. Some nonlimiting examples of these include ethenyl, 1-propenyl, 2-propenyl (allyl), iso-propenyl, 2-methyl-1-propenyl, 1-butenyl, 2-butenyl, ethynyl, 1-propynyl, 2-propynyl, 1-butynyl, and 2-butynyl.

As used herein, the term, "alkoxy" refers to alkyl-O— radical species having 1, 2, 3, 4, 5, 6, 7, 8, 9, 10, 11, 12, 13, 14, 15, 16, 17, 18, 19 and 20 carbons or any subrange of carbons therebetween. They may be unsubstituted or substituted as indicated herein.

As used herein, the term "halogen" or "halo" includes fluoro, chloro, bromo or iodo, and any combination thereof.

As used herein, the term "aryl" means aromatic radicals having 5, 6, 7, 8, 9, 10, 11, 12, 13, 14, 15, 16, 17, 18, 19, 20, 21, 22, 23, 24 and 25 carbons and any subrange of carbons thereof. These may be unsubstitued or substituted as indicated herein. Nonlimiting examples include phenyl, naphthyl, tetrahydronaphthyl, indanyl and the like.

As used herein, the term "heteroaryl" refers to an aromatic heterocyclic group with at least one heteroatom selected from O, S and N in the ring and having 3, 4, 5, 6, 7, 8, 9, 10, 11, 12, 13, 14, 15, 16, 17, 18, 19, 20, 21, 22, 23, 24 and 25 ring carbons and any subrange of carbons thereof. The heteroatoms may be present either alone or in any combination. The heteroaryl groups may be unsubstituted or substituted as indicated herein. One, two, three, four or more heteroatoms may be present. In addition to said heteroatom, the aromatic group may optionally have up to four N atoms in the ring. Nonlimiting examples of heteroaryl groups include pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like; which are optionally unsubstituted or substituted with one or more substituent groups as indicated herein.

The term "heterocyclic" as used herein refers to a cyclic group containing 3, 4, 5, 6, 7, 8, 9, 10, 11, 12, 13, 14, 15, 16, 17, 18, 19, 20, 21, 22, 23, 24 and 25 ring carbons and any subrange of carbons thereof carbon atoms and hetero atoms selected from N, O, S or $NR^1$. Nonlimiting examples include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl and the like. Examples of such monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, 1,4-oxazin-2-yl, 1,2,5-oxathiazin-4-yl and the like; which may be unsubstituted or optionally substituted with one or more substituents as indicated herein.

The compounds herein can be synthesized according to known methods by one of ordinary skill in the art.

The entire contents of the *CRC Handbook of Chemistry and Physics,* 66$^{th}$ edition (1985-86), are incorporated herein by reference for all purposes, the same as set forth at length.

The entire contents of G. P. Moss, P. A. S. Smith and D. Tavernier, *Pure and Applied Chemistry,* 67, 1307-1375 (1995) are incorporated herein by reference for all purposes.

The entire contents of the *International Union of Pure and Applied Chemistry Compendium of Chemical Terminology* ("The Gold Book") 2$^{nd}$ edition, (1997) Edited by A. D. McNaught and A. Wilkinson are incorporated herein by reference for all purposes.

The compounds herein are suitable for administration to subjects, preferably human, in need of the prevention and/or treatment of various indications for CNI-1493 known in the art and already incorporated herein by reference. These include those conditions set out in United States Patent Application Publication Nos. 2003/0134904 to Giordano et al.; 2003/0203969 to Bevec et al.; and 2002/0028851 to Bianchi et al.; and U.S. Pat. Nos. 6,673,777; 6,143,728; 6,319,894; 6,248,787; 6,180,676; 6,022,900; 6,008,255; 5,859,062; 5,854,289; 5,849,794; 5,753,684; 5,750,573; and 5,599,984.

The present inventor has carried out in vitro assays and have measured the activity of the present compounds on the inhibition of LPS-induced nitric oxide and TNFα secretion from murine macrophage cells. The inventors have found, surprisingly and unexpectedly that NO and TNFα activity can be resolved, and it is possible to dissect apart the NO and TNFα activity with compounds having potency in an NO assay which are relatively inactive for TNFα. The inventors have also found that it is possible to provide good "mixed" inhibitors and also more selective TNFα inhibitors. Both TNF activity as well as possible biological targets are contemplated herein.

In particular, the compounds herein are particularly useful for administration to a subject, preferably human, to prevent or reduce the generation of nitric oxide (NO) or in anti-TNF alpha therapy, or to treat or prevent any condition or disease mediated by either or both of NO and TNF alpha. In one embodiment, the compounds may be symmetrical, i.e., have the same groups on either side of the Z linker. In another embodiment, the compounds may be asymmetrical, i.e., have different groups on either side of the linker. In this regard, the linker Z itself is not included in the calculus of symmetry/asymmetry, e.g., a compound having an asymmetrical linker group Z connected to symmetrical end groups would be a symmetrical compound. In one embodiment, a mixture of symmetrical and asymmetrical compounds may be administered. In one embodiment, both asymmetrical and symmetrical compounds are suitable for administration to a subject, preferably human, to prevent or reduce the generation of nitric oxide (NO) or in anti-TNF alpha therapy, or to treat or prevent any condition or disease mediated by either or both of NO and TNF alpha. In another embodiment, asymmetrical compounds exhibit more pronounced anti-TNF alpha activity. In another embodiment, the symmetrical compounds exhibit more pronounced anti-NO activity.

The compounds herein are basic and may if desired form pharmaceutically acceptable salts with organic and inorganic acids. Nonlimiting examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphersulfonic acid, china acid, mandelic acid, o-methylmandelic acid, hydrogen-benzenesulfonic acid, picric acid, adipic acid, d-o-tolyltartraric acid, tartronic acid, α-toluic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

In one embodiment, the compound is in the form of mucate, isethionate, acetate, glutamate, L-lactate, L-tartrate, tosylate, mesylate, fumarate, maleate, citrate, sulfate and combinations thereof. Compositions containing mixtures of salts are possible.

The free base forms may be regenerated by treating the salt with a suitable dilute aqueous base solution such as dilute aqueous sodium hydroxide, potassium carbonate, ammonia and sodium bicarbonate. The free base forms differ from their corresponding salt forms somewhat in certain physical properties, such as solubility in polar solvents, but the salts are otherwise equivalent to their corresponding free base forms.

One embodiment relates to pharmaceutical compositions comprising at least one compound and/or pharmaceutically acceptable salt thereof as an active ingredient and a pharmaceutically acceptable carrier, excipient, adjuvant and/or diluent.

The compounds can also be administered in a form of their pharmaceutically active salts optionally using substantially nontoxic pharmaceutically acceptable carriers, excipients, adjuvants or diluents. The compositions may be prepared in any conventional solid or liquid carrier or diluent and optionally any conventional pharmaceutically-made adjuvant at suitable dosage level in a known way. The preferred preparations are in administrable form which is suitable for oral application. These administrable forms, for example, include pills, tablets, film tablets, coated tablets, capsules, powders and deposits.

Forms other than orally administrable forms are also possible. The compounds and/or pharmaceutical preparations containing said compounds may be administered by any appropriate means, including but not limited to injection (intravenous, intraperitoneal, intramuscular, subcutaneous) by absorption through epithelial or mucocutaneous linings (oral mucosa, rectal and vaginal epithelial linings, nasopharyngial mucosa, intestinal mucosa); orally, rectally, transdermally, topically, intradermally, intragastrally, intracutanly, intravaginally, intravasally, intranasally, intrabuccally, percutanly, sublingually, or any other means available within the pharmaceutical arts.

The pharmaceutical compositions, containing at least one compound and/or pharmaceutically acceptable salts thereof as an active ingredient, will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral nontoxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent by weight of the inventive compound, salt thereof, or a mixture of compound and salt, which range includes all values and subranges therebetween, including 10, 15, 20, 25, 30, 35, 40, 45, 50, 55, 60, 65, 70, 75, 80, 85, and 90% by weight.

Suitable binders include starch, gelatin, natural sugars, corn sweeteners, natural and synthetic gums such as acacia, sodium alginate, carboxymethyl-cellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compounds or compositions may be formulated in sustained release form to provide the rate controlled release of any one or more of the components or active ingredients to optimize the therapeutic effects, i.e. antihistaminic activity and the like. Suitable dosage forms for sustained release include layered tablets containing layers of various disintegration rates or controlled release polymeric matrices impregnated with the active components and shaped in tablet form or capsules containing such impregnated or encapsulated porous polymeric matrices.

Liquid form preparations include solutions, suspensions and emulsions. Nonlimiting examples include water, ethanol, ethanolic, water-ethanol or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds may also be deliverable transdermally. The transdermal compositions may take the form of creams, lotions, aerosols and/or emulsions and can be included in a transdermal patch of the matrix or reservoir type as are conventional in the art for this purpose.

The term capsule refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet means compressed or molded solid dosage form containing the active ingredients with suitable diluents. The tablet can be prepared by compression of mixtures or granulations obtained by wet granulation, dry granulation or by compaction well known to a person skilled in the art.

Oral gels refers to the active ingredients dispersed or solubilized in a hydrophillic semi-solid matrix.

Powders for constitution refers to powder blends containing the active ingredients and suitable diluents which can be suspended in water or juices.

Suitable diluents are substances that usually make up the major portion of the composition or dosage form.

Suitable diluents include sugars such as lactose, sucrose, mannitol and sorbitol, starches derived from wheat, corn rice and potato, and celluloses such as microcrystalline cellulose. The amount of diluent in the composition can range from about 5 to about 95% by weight of the total composition, preferably from about 25 to about 75%, more preferably from about 30 to about 60% by weight.

The term disintegrants refers to materials added to the composition to help it break apart (disintegrate) and release the medicaments. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses and cross-linked microcrystalline celluloses such as sodium croscarmellose, alginates such as alginic acid and sodium alginate, clays such as bentonites, and effervescent mixtures. The amount of disintegrant in the composition can range from about 2 to about 20% by weight of the composition, more preferably from about 5 to about 10% by weight.

Binders characterize substances that bind or "glue" powders together and make them cohesive by forming granules, thus serving as the "adhesive" in the formulation. Binders add cohesive strength already available in the diluent or bulking agent. Suitable binders include sugars such as sucrose, starches derived from wheat, corn rice and potato; natural gums such as acacia, gelatin and tragacanth; deriva tives of seaweed such as alginic acid, sodium alginate and ammonium calcium alginate; cellulosic materials such as methylcellulose and sodium carboxymethylcellulose and hydroxypropyl-methylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d,l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents are materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents are excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Techniques for the formulation and administration of the compounds may be found in "Remington's Pharmaceutical Sciences" Mack Publishing Co., Easton Pa., the entire contents of which are hereby incorporated by reference. A suitable composition comprising at least one compound of the invention may be a solution of the compound in a suitable liquid pharmaceutical carrier or any other formulation such as tablets, pills, film tablets, coated tablets, dragees, capsules, powders and deposits, gels, syrups, slurries, suspensions, emulsions, and the like.

The term "treating" as used herein refers to reversing, alleviating, inhibiting the progress of, or preventing the disorder or condition to which the term applies, or one or more symptoms of the disorder or condition. The term "treatment" as used herein refers to the act of treating as the term is defined above.

The compounds can exist in several tautomeric forms, and geometric isomers and mixtures thereof. All such tautomeric forms are included within the scope of the present invention. Tautomers exist as mixtures of tautomers in solution. In solid form, usually one tautomer predominates. Even though one tautomer may be described, the present invention includes all tautomers of the present compounds.

The present invention also includes atropisomers. Atropisomers refer to compounds that can be separated into rotationally restricted isomers. These compounds may contain olefin-like double bonds. When such bonds are present, the compounds exist as cis and trans configurations and as mixtures thereof.

The compound may exist in any convenient crystalline, semicrystalline, or amorphous form. These may be achieved via typical crystallization routes including vacuum crystallization or spray drying. Depending on the solublity desired, the amorphous form obtained by, e.g., spray-drying may be preferred. The spray drying may be carried out from aqueous, ethanolic, organic, or mixed aqueous ethanolic solutions of the compound or its salt or a mixture thereof. The compound may exist in a form comprising one or more waters of hydration.

The present invention also includes isotopically-labeled acid compounds, which are identical to those recited above, but for the fact that one or more atoms are replaced by an atom having an atomic mass or mass number different from the atomic mass or mass number usually found in nature. Examples of isotopes that can be incorporated into compounds include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{32}P$, $^{35}S$, $^{18}F$, and $^{36}Cl$, respectively. Compounds, prodrugs thereof, and pharmaceutically acceptable salts of said compounds or of said prodrugs which contain the aforementioned isotopes and/or other isotopes of other atoms are within the scope of this invention. Certain isotopically-labeled compounds, for example, those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, it would be preferred in some circumstances. Isotopically labeled compounds and/or prodrugs can generally be prepared by substituting a readily available isotopically labeled reagent for a non-isotopically labeled reagent.

EXAMPLES

The following experimental and tabular examples were prepared in accordance with methods available to one of ordinary skill in the art. Below, "MF" means molecular formula, and "MW" means molecular weight in grams/mole.

Analog 7

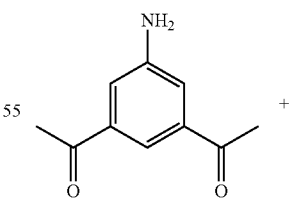

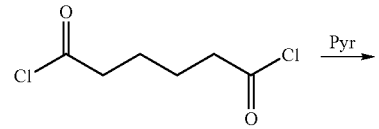

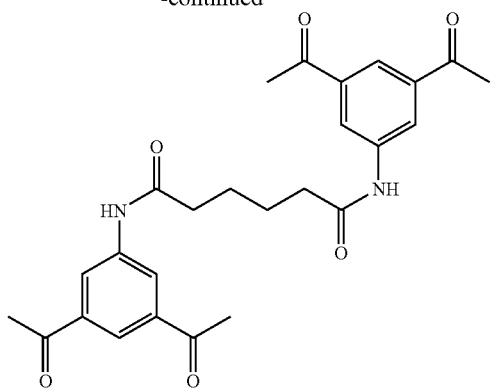

3,5-Diacetylaniline (150 mg, 0.847 mmol) and pyridine (0.16 mL, 1.7 mmol) were combined in 20 mL of methylene chloride and cooled to 0° C. Adipoyl chloride (0.17 mL, 0.91 mmol) was added. After stirring for 15 minutes, the ice bath was removed and the reaction mixture was stirred at room temperature for 15 hours. Water was then added and the mixture was filtered. The solid was collected and boiled in a 1/1 mixture of acetone/methanol (30 mL). After cooling the mixture to room temperature, the mixture was filtered again and the solid was collected. The off-white solid was very clean diamide product (142 mg, 0.305 mmol). LC/MS (EI) 465 (M+1), 487 (M+Na).

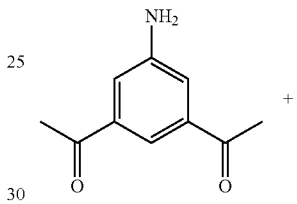

The diamide (142 mg, 0.306 mmol) was suspended in 4 mL of 2-methoxyethanol. Concentrated HCl (27 μL, 0.43 mmol) and 1.3 mL of water were added and the mixture was heated to 50° C. Aminoguanidine hydrochloride (68 mg, 0.62 mmol) was added and the mixture was stirred at 60° C. for four hours. Ethanol (2 mL) was added and the reaction was stirred at room temperature for two days. The mixture was filtered. LC/MS showed only a 50% conversion of starting material to product and the trisubstituted product. The mixture of solids was subjected to the reaction conditions again, except the water was omitted. After 10 hours, the reaction was cooled to room temperature and stirred for two days. Water (5 mL) was added to the reaction mixture. It was then filtered and washed with 10 mL of water. The solid was collected and dried to give 97 mg of pure material. The aqueous filtrate did contain more of the product but the purity was much less. $^{1}$H NMR (DMSOd$^{6}$) δ 11.03 (s, 4H), 10.19 (s, 2H), 8.12 (s, 4H), 8.05 (s, 2H), 7.73 (broad s, 12H), 2.36 (m, 16H), 1.66 (broad s, 4H); LC/MS (EI) 689 (M+1), 711 (M+Na).

Analog 8

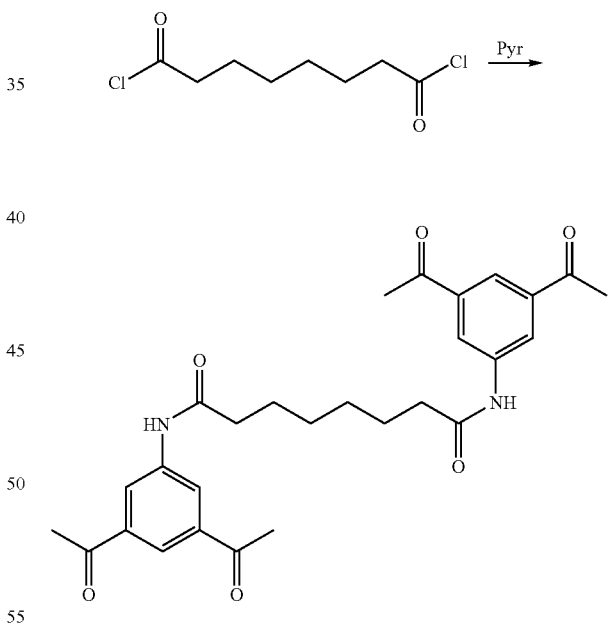

3,5-Diacetylaniline (200 mg, 1.13 mmol) and pyridine (0.18 mL, 1.7 mmol) were combined in 10 mL of methylene chloride. Suberoyl chloride (0.11 mL, 0.62 mmol) was added and the reaction mixture was stirred at room temperature for 5 hours. Water was then added and the mixture was filtered. The solid was collected and boiled in a 1/1 mixture of acetone/methanol. After cooling the mixture to room temperature, the mixture was filtered again and the solid was collected. The white solid was very clean diamide product (168 mg, 60%); LC/MS (EI) 493 (M+1), 515 (M+Na).

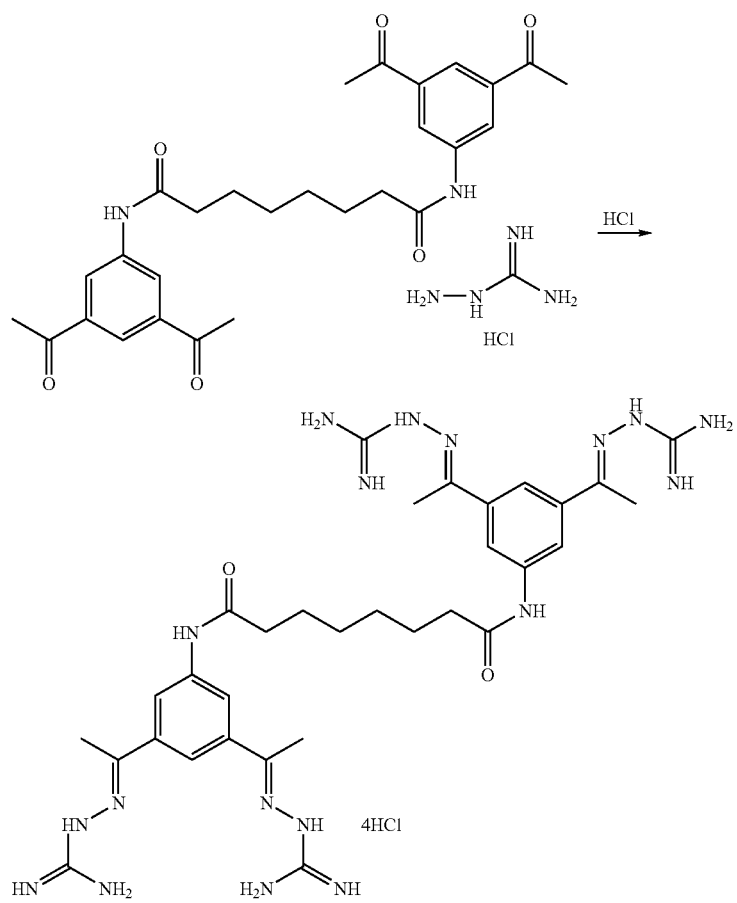

The diamide (166 mg, 0.337 mmol) was suspended in 10 mL of 2-methoxyethanol. Aminoguanidine hydrochloride (298 mg, 2.69 mmol) was added and the mixture was heated with stirring to 115° C. After eight hours, the reaction mixture became a clear solution. Another 289 mg of the aminoguanidine hydrochloride was added and the mixture stirred at 115° C. for 15 hours. A white precipitate was now visible. The reaction mixture was cooled to room temperature and filtered. The solids were washed with 20 mL of water, collected and dried. Recrystallization from 25 mL of methanol gave the product as a white solid (145 mg, 50%): $^1$H NMR (DMSOd$^6$) δ 11.04 (s, 4H), 10.14 (s, 2H), 8.10 (s, 4H), 8.05 (s, 2H), 7.75 (broad s, 12H), 2.36 (m, 16H), 1.62 (broad s, 4H), 1.35 (broad s, 4H); LC/MS (EI) 717 (M+1), 739 (M+Na).

Analog 9

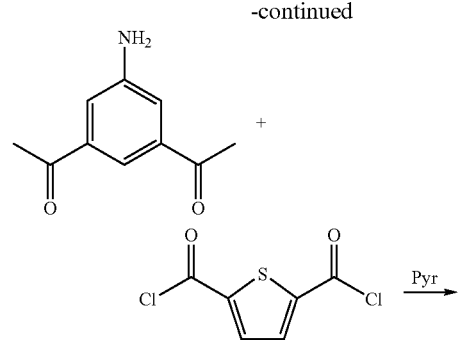

-continued

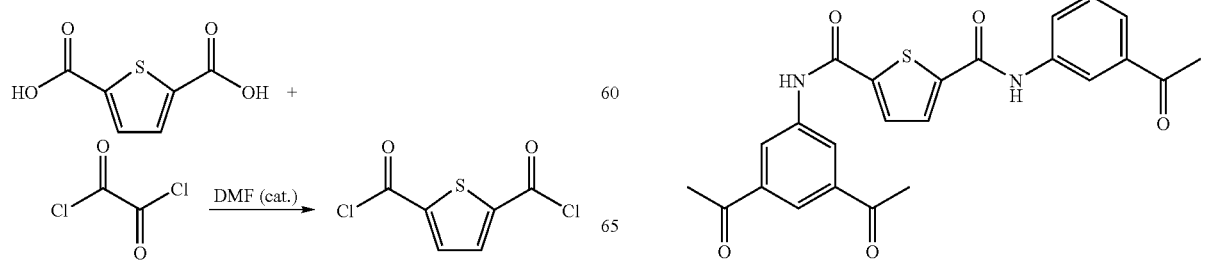

2,5-Thiophenedicarboxylic acid (200 mg, 1.16 mmol) was suspended in 4 mL of methylene chloride. Oxalyl chloride (0.25 mL, 2.9 mmol) was added. One drop of dimethylformamide was then added. The evolution of gas was observed. After 20 minutes, it had stopped and another drop of dimethylformamide was added. This was repeated for one hour. The solvent was removed from the reaction mixture and the yellow solid was dried by a vacuum pump. The diacid chloride was used without further purification.

3,5-Diacetylaniline (150 mg, 0.847 mmol) and pyridine (0.14 mL, 1.2 mmol) were combined in 4 mL of methylene chloride. The crude 2,5-thiophenedicarboxylic acid chloride (89 mg, 0.42 mmol) in 3 mL of methylene chloride was slowly added to the solution. The reaction mixture was stirred at room temperature for 1 day. A lot of starting aniline was still present by LC/MS. More of the diacid chloride (89 mg, 0.42 mmol) in 2 mL of methylene chloride was added to the reaction mixture. The mixture was stirred for 36 hours. Water was added and the mixture was filtered. The solids product (164 mg, 79%) were collected and used without further purification: LC/MS (EI) 491 (M+1), 513 (M+Na).

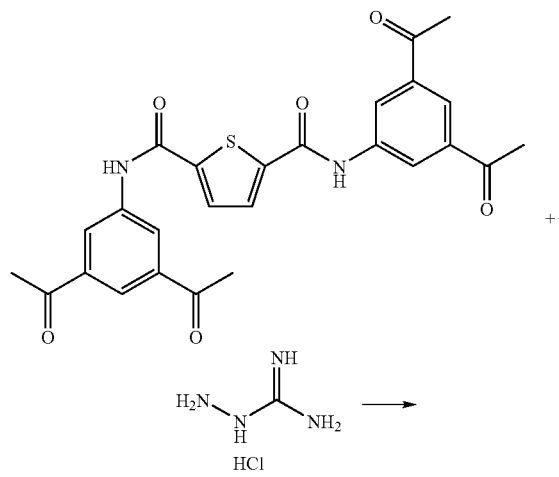

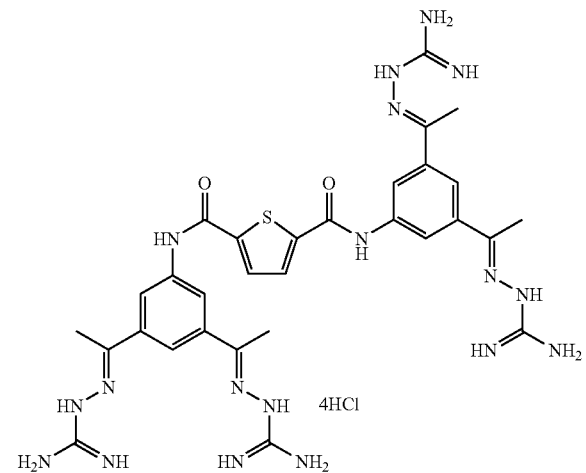

-continued

The diamide (164 mg, 0.334 mmol) was suspended in 10 mL of 2-methoxyethanol. The aminoguandine hydrochloride (296 mg, 2.67 mmol) was added and the mixture was heated to 85° C. with stirring for 1 day. Aminoguanidine hydrochloride (296, 2.67 mmol) was added again and the reaction temperature was raised to 115° C. and stirred 8 hours. The addition was repeated and the stirring was continued for 18 hours. The reaction mixture was cooled to room temperature. The mixture was filtered and the solids were washed with 20 mL of water. The solid was collected and titurated with methylene chloride. Further purification was accomplished by recrystallization from 25 mL of boiling ethanol and gave the product as a beige solid (179 mg, 63%): $^1$H NMR (DMSOd$^6$) δ 11.05 (s, 4H), 10.79 (s, 2H), 8.37 (s, 4H), 8.28 (s, 2H), 8.12 (s, 2H), 2.41 (s, 12H); LC/MS (EI) 715 (M+1); 737 (M+Na).

Analog 10

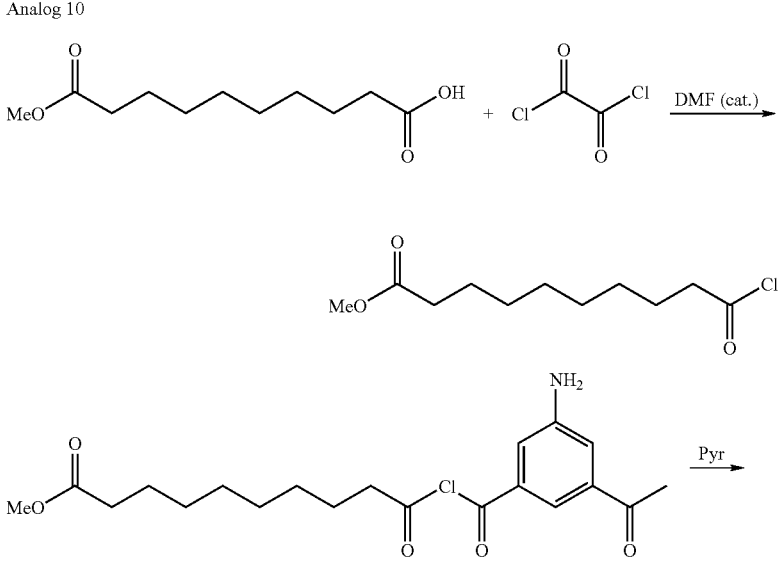

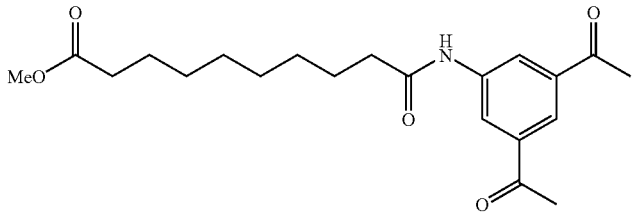

Sebacic acid monomethyl ester (238 mg, 1.10 mmol) was suspended in 4 mL of methylene chloride. Oxalyl chloride (0.12 mL, 1.3 mmol) was added. One drop of dimethylformamide was then added. The evolution of gas was observed. After 20 minutes, it had stopped and another drop of dimethylformamide was added. This was repeated for one hour. The solvent was removed from the reaction mixture and the yellow solid was dried by a vacuum pump. The acid chloride was used without further purification.

3,5-Diacetylaniline (133 mg, 0.750 mmol) and pyridine (0.21 mL, 1.5 mmol) were combined in 5 mL of methylene chloride. The acid chloride (194 mg, 0.825 mmol) in 3 mL of methylene chloride was slowly added. The reaction mixture was stirred at room temperature for 5 hours. An aqueous, saturated solution of sodium bicarbonate was added and the mixture continued stirring for 30 minutes. The two phases were separated and the aqueous solution was extracted with methylene chloride. The organics were combined and dried over sodium sulfate. The product was purified by column chromatography using 3:1 methylene chloride:ethyl acetate as the eluent. This gave 210 mg (75%) of the desired product as an off-white solid: LC/MS (EI) 376 (M+1).

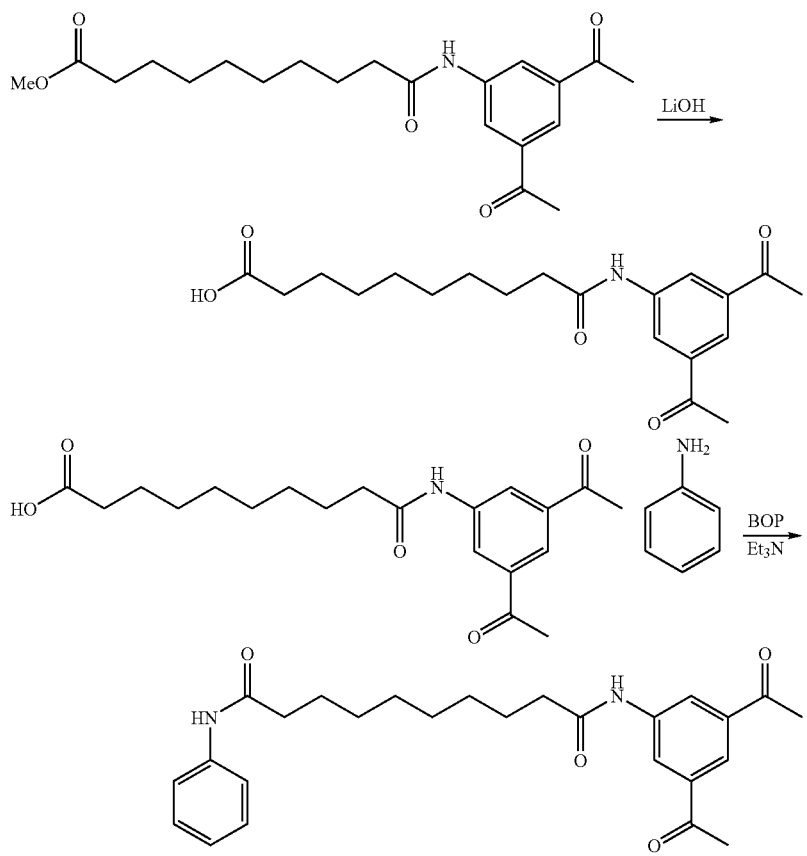

The monomethyl ester amide (210 mg, 0.559 mmol) was dissolved in a 3:1 mixture of methanol:water. Lithium hydroxide monohydrate (47 mg, 1.1 mmol) was added and the reaction mixture was stirred for one day. The methanol was removed by rotary evaporation. The residue was diluted with 30 mL of water and was extracted three times with 20 mL of ethyl acetate. The aqueous layer was acidified to a pH~2 using 1 mL of 6N hydrochloric acid solution. The aqueous layer was then extracted again three times with 20 mL of ethyl acetate. The organics from this last extraction were combined and dried over sodium sulfate. The mixture was then filtered and the solvent removed by rotary evaporation. The residue was purified by trituration with methylene chloride to give the pure product as a white solid (121 mg, 61%): $^1$H NMR (DMSOd$^6$) δ 10.28 (s, 1H), 8.42 (s, 2H), 8.14 (s, 1H), 2.63 (s, 6H), 2.34 (t, J=7.6 Hz, 2H), 2.18 (t, J=7.3 Hz, 2H), 1.60 (m, 2H), 1.49 (m, 2H), 1.28 (m, 8H); LC/MS (EI) 715 (M+1); 737 (M+Na).

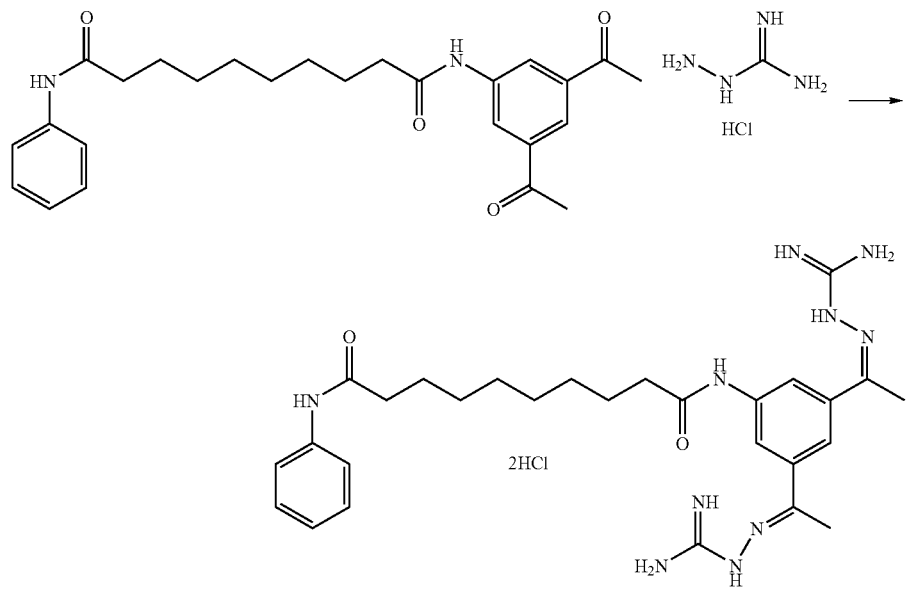

The diamide (149 mg, 0.341 mmol) was suspended in 10 mL of 2-methoxyethanol. The aminoguanidine hydrochloride (113 mg, 1.02 mmol) was added and the mixture was heated to 95° C. for 8 hours. More aminoguanidine hydrochloride (113 mg, 1.02 mmol) was added and the reaction mixture continued to be stirred at 95° to 100° C. for another 15 hours. Conversion was still not complete and aminoguanidine hydrochloride (226 mg, 2.04 mmol) was added again and the temperature was raised to 120° C. and heated for 8 hours. The addition was repeated the mixture was stirred another 15 hours at that temperature. The mixture was then cooled to room temperature and the solvent was removed by rotary evaporation. The residue was heated with 25 mL of methanol until it dissolved completely. A small amount of water (1 mL) was added and the mixture was cooled to room temperature. The crystals that formed were collected to give pure product (60 mg, 28%): $^1$H NMR (DMSOd$^6$) δ 11.29 (s, 2H), 10.16 (s, 1H), 9.91 (s, 1H), 8.72 (s, 1H), 8.12 (s, 2H), 8.04 (s, 1H), 7.84 (broad s, 6H), 7.59 (d, J=7.7 Hz, 2H), 7.27 (t, J=8.0 Hz, 2H), 7.00 (t, J=7.4 Hz, 1H), 4.69 (s, 1H), 2.38 (s, 6H), 2.31 (m, 4H), 1.59 (m, 4H), 1.30 (broad s, 8H); LC/MS (EI) 549 (M+1), 571 (M+Na).

Analog 11

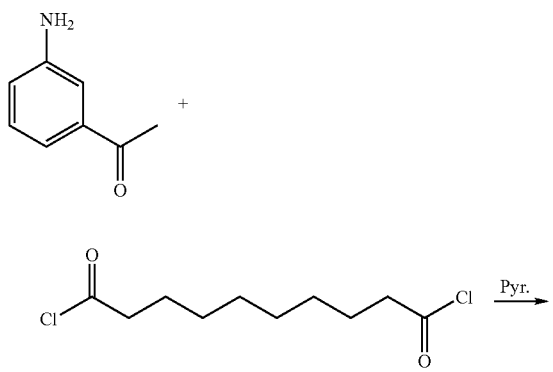

-continued

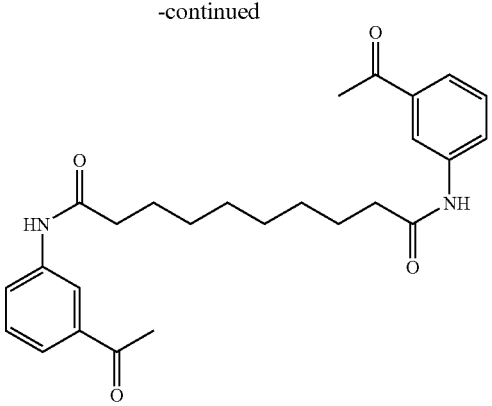

3-Acetylaniline (201 mg, 1.49 mmol) and pyridine (0.18 mL, 1.7 mmol) were combined in 10 mL methylene chloride. Sebacoyl chloride (0.18 mL, 0.85 mmol) was slowly added and the reaction mixture was stirred at room temperature for 16 hours. A saturated aqueous solution of sodium bicarbonate (5 mL) was added and the mixture was stirred for 30 minutes. The mixture was filtered and the solids collected. This gave 310 mg (95%) of the product as a white solid: LC/MS (EI) 437 (M+1), 459 (M+Na).

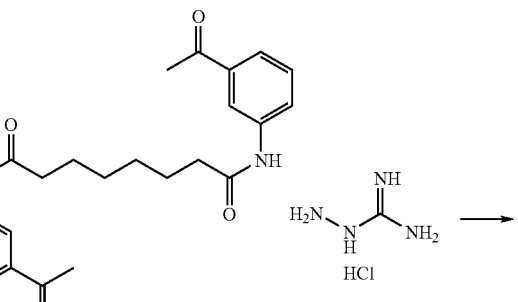

-continued

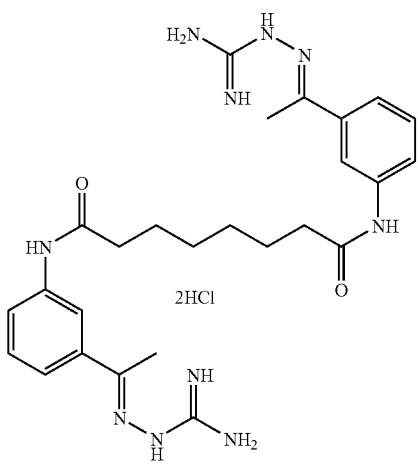

The diamide (272 mg, 0.623 mmol) was suspended in 10 mL of 2-methoxyethanol, The aminoguanidine hydrochloride (207 mg, 1.87 mmol) was added and the mixture was heated to 115° C. and was stirred for 8 hours. More aminoguanidine hydrochloride (207 mg, 1.87 mmol) was added and the mixture continued to stir at 115° C. for one day. The mixture was then cooled to room temperature and the solvent was removed by rotary evaporation. The residue was dissolved in 8 mL of hot methanol and 1 mL of water was added. The mixture was allowed to slow cool to room temperature and set for 2 days. The mixture was filtered and the crystals were collected to give pure product (248 mg, 64%): $^1$H NMR (DMSOd$^6$) δ 10.98 (s, 2H), 10.00 (s, 2H), 7.98 (s, 2H), 7.72 (m, 8H), 7.33 (t, J=8.0 Hz, 2H), 3.30 (s, 2H), 2.30 (m, 10H), 1.59 (m, 4H), 1.30 (s, 8H); LC/MS (EI) 549 (M+1); 571 (M+Na).

Other compounds:

30 mg of mono-aminoguanidine were prepared. From the method of synthesis and purification, this was probably the free base. The material was very high quality, on the order of 97-98% by HPLC. The NMR data was also clean.

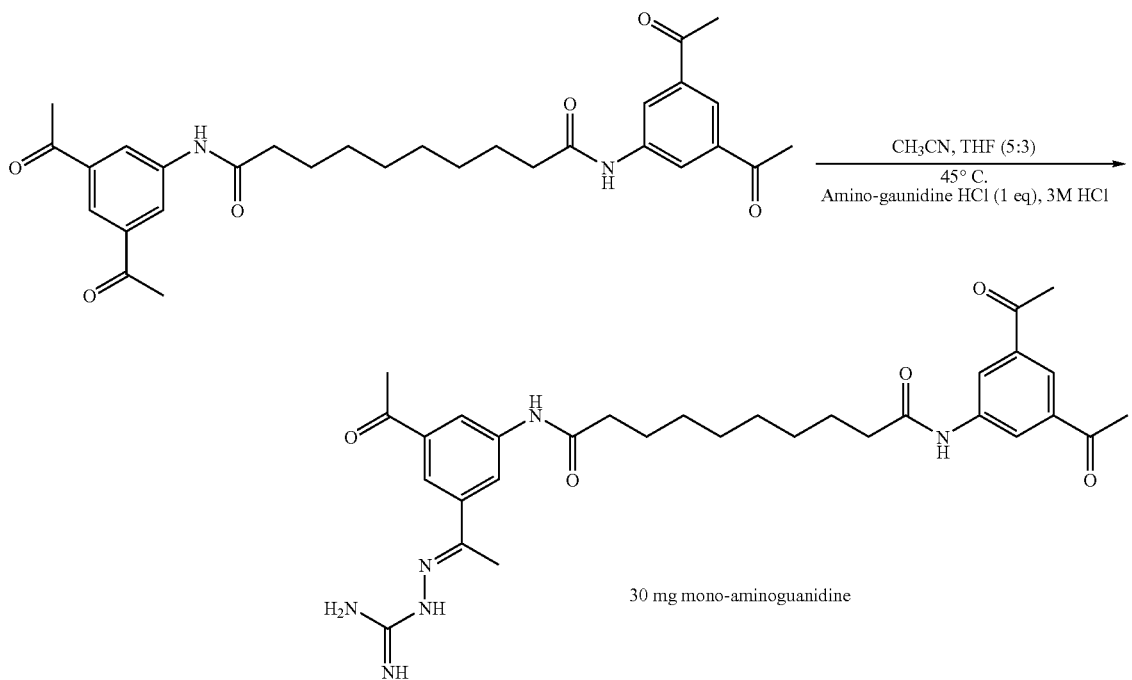

Tetra-aminoguanidine compound:
The acid chloride route was chosen for these compounds, since there was less contamination with DCC by-products.

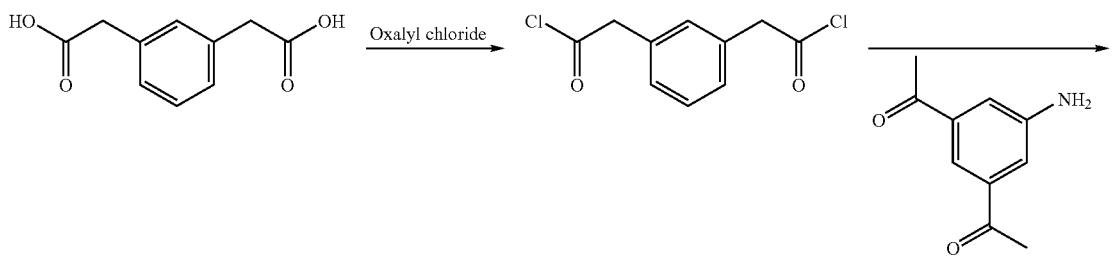

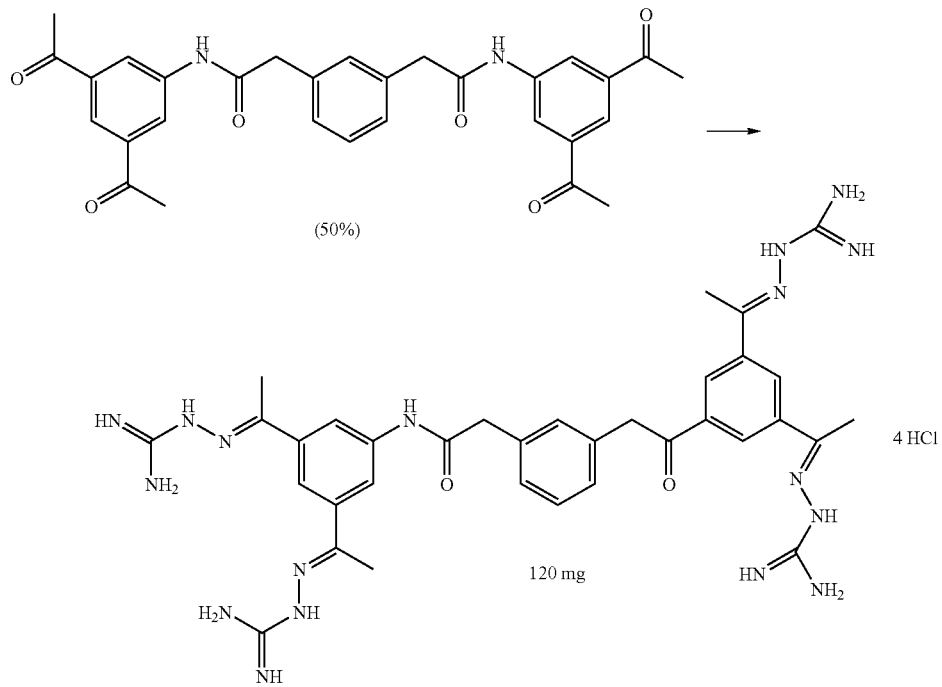

Tetra-acetyl compound:

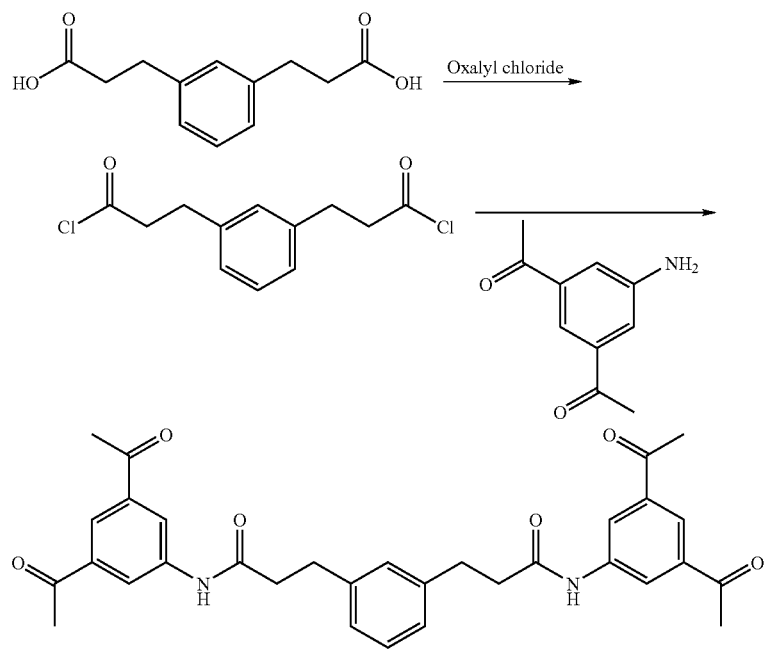

Tris-aminoguanidine compound:

Using conditions similar to the mono-aminoguanidine synthesis, the tetra-acetyl compound was dissolved completely in CH₃CN:THF and a solution of amino-guanidinine hydrochloride in methanol was added. Only two equivalents of amino-guanidine were used, since the object was to make the bis-amino guanidine impurity. However, this reaction produced mono and tris amino-guanidine, with very little bis. The tris amino-guanidine precipitated from the reaction mixture along with some mono, resulting in a 3:1 mixture. Attempts to purify this by chromatography were not successful, but chromatography will be tried again. However, it may turn out that each compound behaves differently, and each will require a different purification scheme.

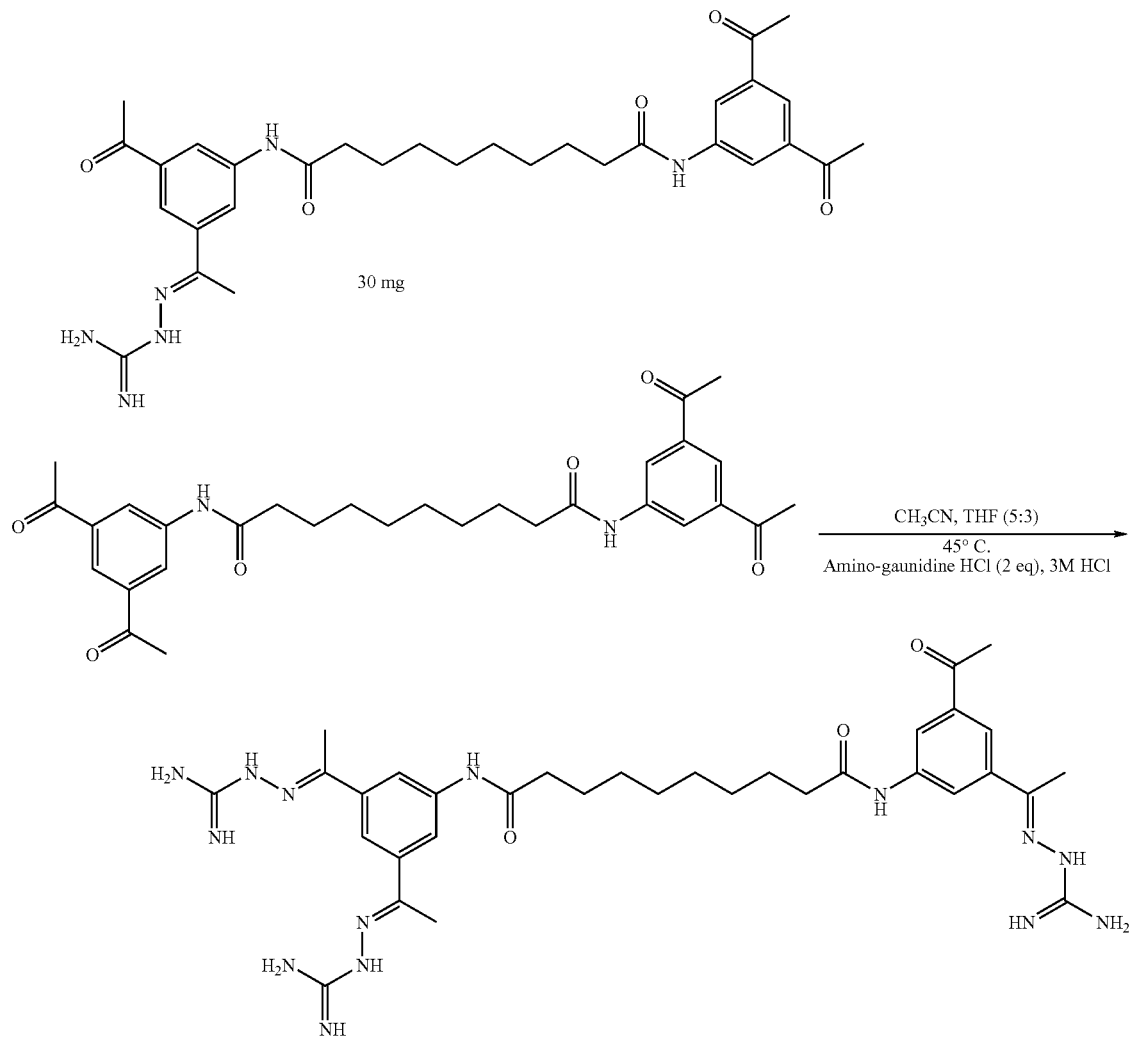
The following compounds were prepared.
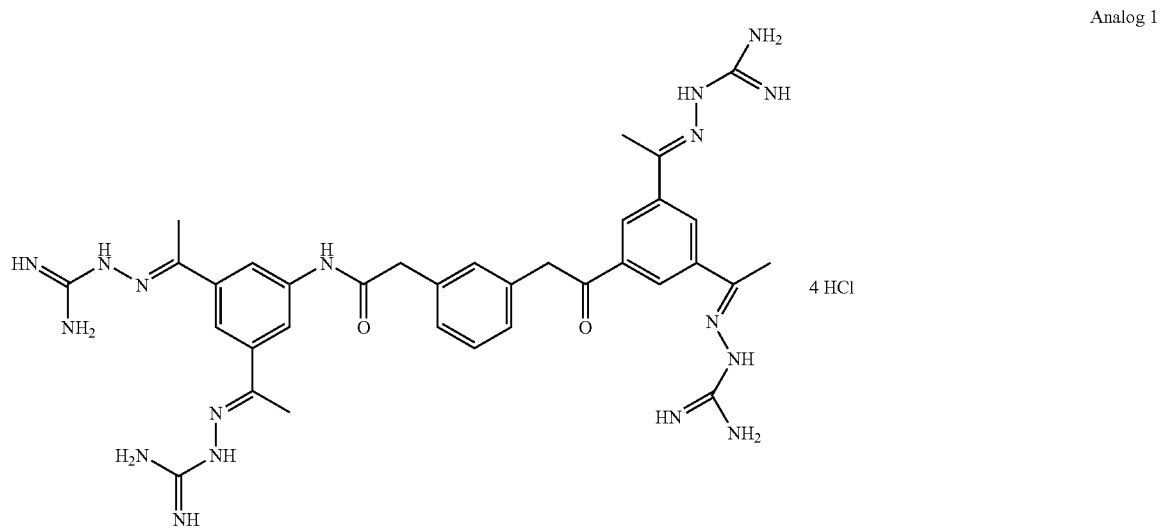
Analog 1
4 HCl

-continued

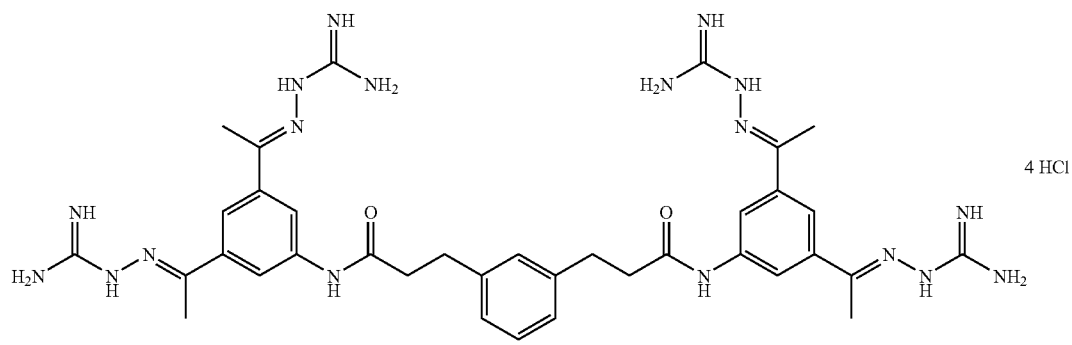

Analog 2

4 HCl

Reaction scheme to Analog 12 intermediate:

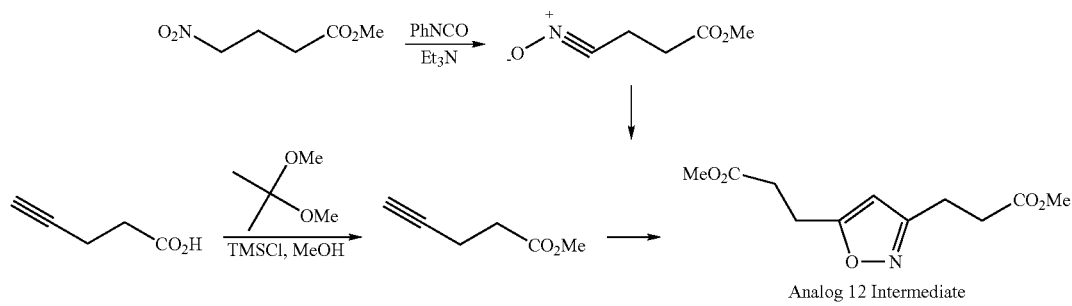

Analog 12 Intermediate

Anti-Inflammatory Activity in RAW 264.7 Cells:

The present inventors measured the ability of eight test articles to inhibit LPS-induced nitric oxide and TNFα secretion from murine macrophage cells.

This study was performed according to the protocol, testing facility standard operating procedures and to the principles of the US FDA Good Laboratory Practice Regulations.

Compounds:

Analog 5

Analog 6

Analog 7

Analog 9

Analog 10

Analog 11

Analog 12

Analog 13

CNI-1493

Methods:

The studies were conducted in RAW 264.7 cultures.

Culture of RAW 264.7 Cells:

RAW 264.7 murine macrophage cells (ATCC, TIB-71) were maintained at 5% $CO_2$, 37° C. in RPMI media (Fisher 15-040-CV, 1 mg/L glutathione) with 10% fetal bovine serum (fbs, Fisher, lot 05069F) plus 2 mM L-glutamine and penicillin/streptomycin. The cells were subcultured every two to three days. Cells were plated in tissue culture treated 96 well plates at a density of $1\times10^5$ cells/well and incubated at 5% $CO_2$, 37° C. for at least one hour prior to initiation of the assay. The cells were washed with RPMI with 10% fbs prior to the initiation of the assay.

Anti-Inflammatory Activity:

The compounds were weighed, dissolved in DMSO for stock solutions of 10 mg/mL and serially diluted in RPMI. The plated RAW 264.7 cells were pretreated in duplicate with the test compounds, control (CNI-1493) or vehicle for 1 hour at final concentrations of 0, 0.1, 1.0, 10, and 100 μg/mL. The cells were stimulated with 100 ng/mL LPS (*E. coli* 0111:B4) and incubated at 5% $CO_2$, 37° C. for 24 hours. The media was collected and stored at −20° C.

TNFα Quantitation:

Murine TNFα was measured by ELISA (BioSource or comparable commercial source) following the suppliers instructions. The stored media was diluted 1:30.

Nitric Oxide (Nitrite) Measurement:

To 50 μL of cell-free media, 50 μL of Griess Reagent (1 part 0.1% naphthylethylenediamine diHCl, 1 part 1.32% sulfanilimide in 60% acetic acid) was added and incubated for no more than 5 minutes at ambient temperature. The samples were read on a microtiter plate reader at 540 nm and compared to a 0.1-5 mmol nitrite standard curve.

The entirety of each of the following references is hereby incorporated by reference:

Bianchi, M et al., Mol Med, 1995, 1:254-266.

Bianchi, M et al., J Exp Med, 1996, 183: 927-936.

Results and Discussion:

Four compounds, Analog 10, Analog 12, Analog 5 and Analog 11 inhibit release of TNFα from LPS-induced RAW 264.7 cells with $IC_{50}$ values of 8.8, 26.7, 27.7 and 47.6 μg/mL, respectively (FIG. 1). CNI-1493 inhibits release of TNFα at an $IC_{50}$ of approximately 8 μg/mL. The remaining compounds have little ($IC_{50}$>50 μg/mL) or no ($IC_{50}$>100 μg/mL) effect on TNFα release.

Nitric oxide release is inhibited by CNI-1493 (FIG. 2) with an $IC_{50}$ of approximately 5.5 μg/mL. Nitric oxide release is inhibited with $IC_{50}$ values of <1 μg/mL by Analog 5, Analog 12 and Analog 7 and to a lesser extent by the remaining compounds (FIG. 2).

FIGS. 3 and 4 show the combined results for inhibition of nitric oxide and TNFα release. No absolute correlation appears to exist between activity for nitric oxide inhibition and inhibition of TNFα release.

Figure 5:
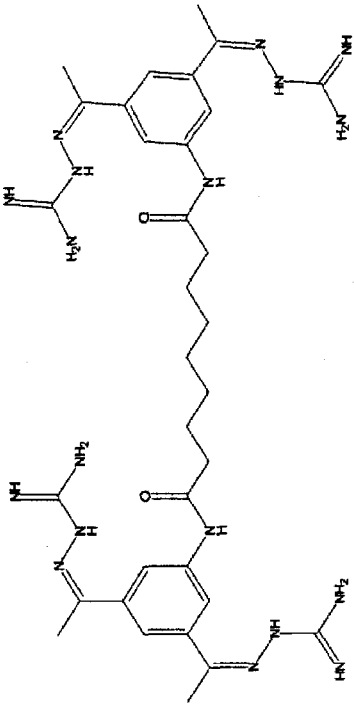
FIG. 5A-I shows structures and results of exemplified compounds, and others.
Figure 5:
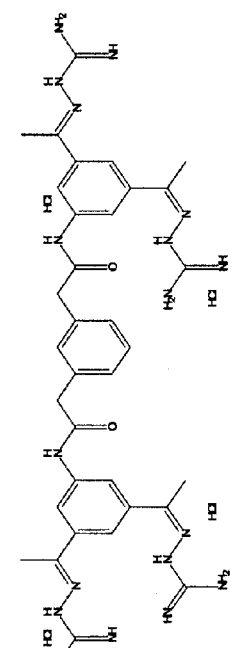
Figure 5:
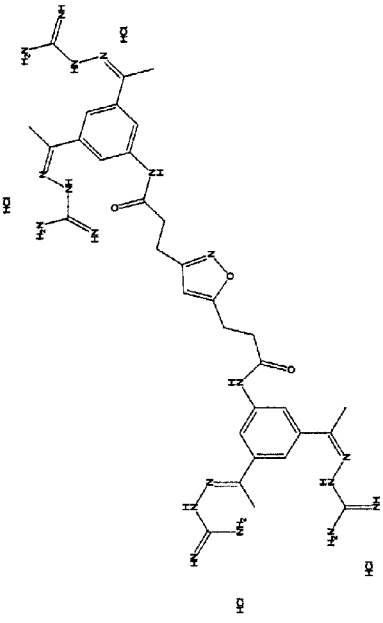
Figure 5:
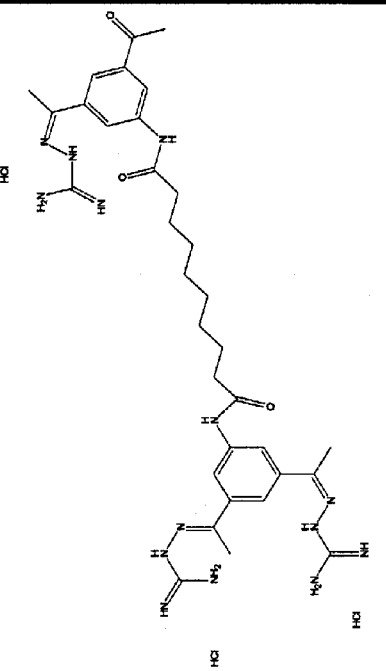

FIG. 5 shows structures and results of these and other compounds.

Conclusions:

Analog 10, Analog 12, Analog 5 and Analog 11 inhibit release of TNFα from LPS-induced RAW 264.7 cells with $IC_{50}$ values of 8.8, 26.7, 27.7 and 47.6 μg/mL, respectively.

Analog 5, Analog 12 and Analog 7 inhibit nitric oxide release with $IC_{50}$ values of <1 μg/mL.

No absolute correlation appears to exist between activity for nitric oxide inhibition and inhibition of TNFα release.

It will be understood that various changes in the details, materials and arrangements of the parts which have been described and illustrated in order to explain the nature of this invention may be made by those skilled in the art without departing from the principle and scope of the invention as expressed in the following claims.

The invention claimed is:

1. A compound, having the formula:

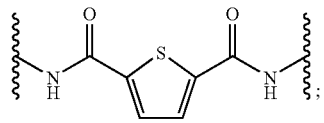

or a salt thereof;

wherein $X^3$ and $X^4$ each independently represent GhyCH— or GhyCCH$_3$—;

wherein Z is a group having the formula —A—(CH$_2$)$_p$—A—, wherein p is 1, 2, 3, 4, 5, 6, 7, 8, 9, or 10, and wherein the A's are each independently —NH(CO)—, —(CO)NH—, or —NH(CO)NH— groups;

or wherein Z is a group having the formula —A—(C$_6$H$_4$)—A—, wherein the A's are each independently —CO—, —NH(CO)—, —(CO)NH—, or —NH(CO)NH— groups;

or wherein Z is a group having the formula:

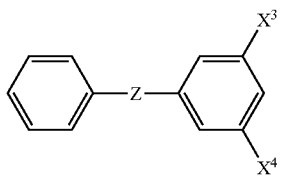

or wherein Z is a group having the formula:

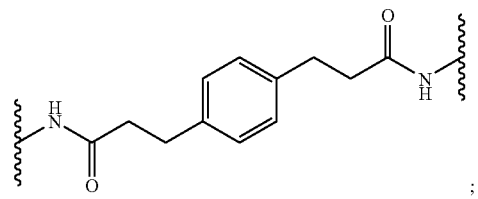

or wherein Z is a group having the formula:

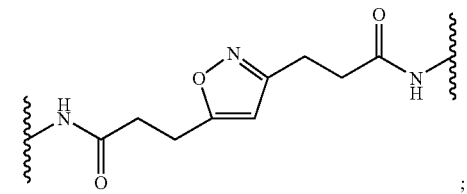

or wherein Z is a group having the formula:

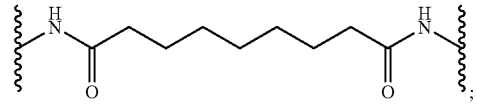

or wherein Z is a group having the formula:

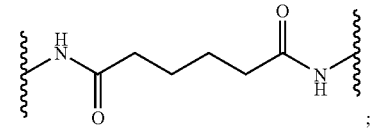

or wherein Z is a group having the formula:

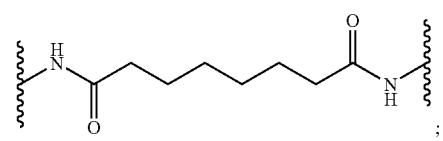

or wherein Z is a group having the formula:

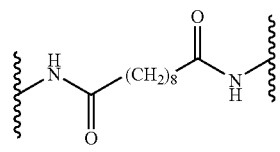

or wherein Z is a group having the formula:

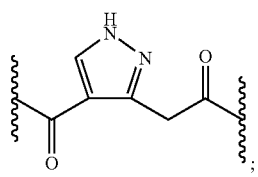

2. The compound of claim 1, wherein $X^3$, and $X^4$ are each GhyCH—.

3. The compound of claim 1, wherein $X^3$, and $X^4$ are each GhyCCH$_3$—.

4. The compound of claim 1, wherein Z is an —A—(CH$_2$)$_p$—A— group, wherein p is 1, 2, 3, 4, 5, 6, 7, 8, 9, or 10, and wherein the A's are each independently —NH(CO)—, —(CO)NH—, or —NH(CO)NH— groups.

5. The compound of claim 1, wherein Z is an —A—(C$_6$H$_4$)—A— group, wherein the A's are each independently —CO—, —NH(CO)—, —(CO)NH—, or —NH(CO)NH— groups.

6. The compound of claim 1, wherein Z is a group having the formula:

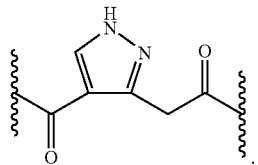

7. The compound of claim 1, wherein Z is a group having the formula:

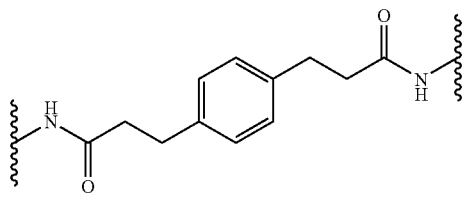

8. The compound of claim 1, wherein Z is a group having the formula:

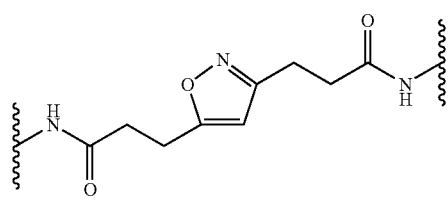

9. The compound of claim 1, wherein Z is a group having the formula:

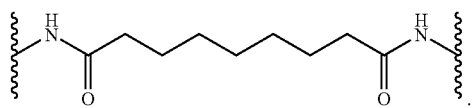

10. The compound of claim 1, wherein Z is a group having the formula:

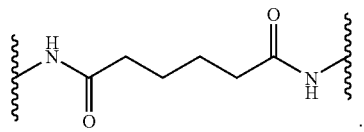

11. The compound of claim 1, wherein Z is a group having the formula:

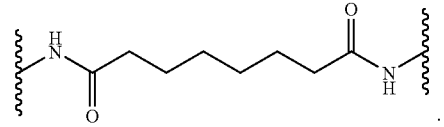

12. The compound of claim 1, wherein Z is a group having the formula:

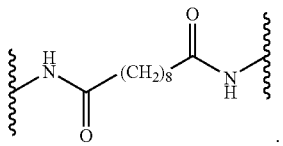

13. The compound of claim 1, having the formula:

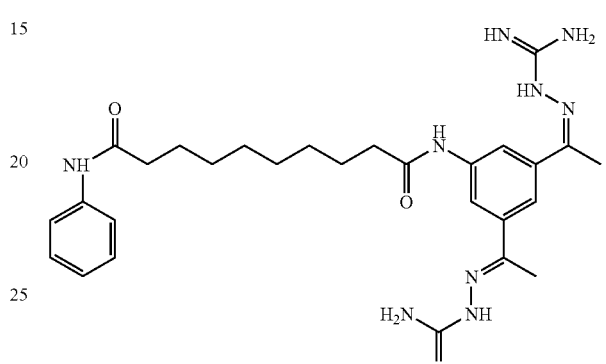

14. The compound of claim 1, having the formula:

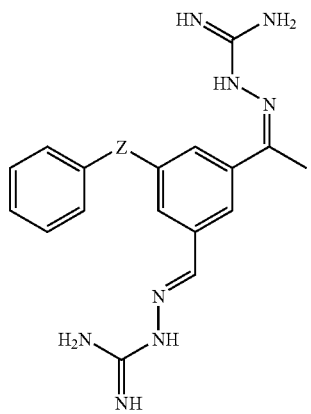

15. The compound of claim 1, which is in the salt form.

16. A composition, comprising the compound of claim 1, or salt thereof, and at least one pharmaceutically acceptable carrier, excipient, adjuvant or diluent.

17. A method of treating inflammation, comprising administering the compound of claim 1 or salt thereof to a human.

18. The method of claim 17, wherein said human is in need of inhibition of the release of TNFα, NO, or both.

19. The method of claim 17, wherein said human is in need of inhibition of the release of TNFα.

20. The method of claim 17, wherein said human is in need of inhibition of the release of NO.

* * * * *